United States Patent
Stojanovic et al.

(10) Patent No.: US 10,338,068 B2
(45) Date of Patent: Jul. 2, 2019

(54) SELECTION OF BIOLOGICAL OBJECTS

(71) Applicant: The Trustees of Columbia University in the City of New York, New York, NY (US)

(72) Inventors: Milan N. Stojanovic, Fort Lee, NJ (US); Sergei Rudchenko, Bronx, NY (US); Maria Rudchenko, Bronx, NY (US); Steven Taylor, Jersey City, NJ (US)

(73) Assignee: The Trustees of Columbia University in the City of New York, New York, NY (US)

(*) Notice: Subject to any disclaimer, the term of this patent is extended or adjusted under 35 U.S.C. 154(b) by 672 days.

(21) Appl. No.: 14/931,941

(22) Filed: Nov. 4, 2015

(65) Prior Publication Data

US 2016/0153989 A1    Jun. 2, 2016

Related U.S. Application Data

(63) Continuation-in-part of application No. PCT/US2014/045832, filed on Jul. 8, 2014.

(60) Provisional application No. 61/843,892, filed on Jul. 8, 2013, provisional application No. 62/074,796, filed on Nov. 4, 2014.

(51) Int. Cl.
    *G01N 33/569* (2006.01)

(52) U.S. Cl.
    CPC . *G01N 33/56966* (2013.01); *G01N 2333/705* (2013.01)

(58) Field of Classification Search
    None
    See application file for complete search history.

(56) References Cited

U.S. PATENT DOCUMENTS

| 7,122,319 | B2* | 10/2006 | Liu | C12Q 1/6823 435/6.1 |
|---|---|---|---|---|
| 2004/0235043 | A1 | 11/2004 | Schneider et al. | |
| 2007/0299645 | A1 | 12/2007 | Shapiro et al. | |
| 2013/0023436 | A1 | 1/2013 | Jones et al. | |

FOREIGN PATENT DOCUMENTS

| EP | 1154376 | 5/2000 |
|---|---|---|
| WO | WO2012/071428 | 5/2012 |
| WO | WO2014066984 | 10/2013 |

OTHER PUBLICATIONS

Bendall, et al., Single-cell mass cytometry of differential immune and drug responses across a human hematopoietic continuum, Science, 2011, vol. 332, No. 6030, pp. 687-696.

(Continued)

*Primary Examiner* — Robert T. Crow
(74) *Attorney, Agent, or Firm* — Dentons US LLP

(57) ABSTRACT

Provided herein are molecular automaton systems for identification, isolation, or elimination of a target biological object. Some embodiments include modules specific for a target biological object having a first biological object surface marker and a second biological object surface marker. Some embodiments include modules specific for a target biological object having a first biological object surface marker but not a second biological object surface marker.

39 Claims, 33 Drawing Sheets

Specification includes a Sequence Listing.

(56) References Cited

OTHER PUBLICATIONS

Benenson et al., Programmable and autonomous computing machine made of biomolecules, Nature, 2001, vol. 414, pp. 430-434.
Benenson et al., An autonomous molecular computer for logical control of gene express, Nature, 2004, vol. 429, pp. 423-429.
Boltz et al., Bi-specific aptamers mediating tumor cell lysis, The Journal of Biological Chemistry, 2011, vol. 286, No. 24, pp. 21896-21905.
Brandt et al., Type 1 diabetes in biobreeding rats is critically linked to an imbalance between Th17 and regulatory T cells and an altered TCR repertoire, The Journal of Immunology, 2010, vol. 185, pp. 2285-2294.
Carter, Potent antibody therapeutics by design, Nature Reviews Immnology, 2006, vol. 6, No. 5, pp. 343-357.
Desilva et al., Molecular logic and computing, Nature Nanotechnology, 2007, vol. 2, pp. 399-410.
Dillon et al., RNAi as an experimental and therapeutic tool to study and regulate physiological and disease process, Annual Rev of Physiology, 2005, vol. 67, pp. 147-173.
Distributed Autonomous Robotic Systems: The 11th International Symposium (Springer Tracts in Advanced Robotics) 2014, 452 pages.
Douglas et al., A logic-gated nanorobot for targeted transport of molecular payloads, Science, 2012, vol. 335, No. 6070, pp. 831-834.
Dykxhoorn et al., The silent revolution: RNA interference as basic biology, research tool, and therapeutic, Annual Review of Medicine, 2005, vol. 56, pp. 401-423.
Elhai et al., Conjugal transfer of DNA to cyanobacteria, Methods in Enzymology, 1988 vol. 167, pp. 747-754.
Fanning et al., Gene-expressed RNA as a therapeutic: issues to consider, using ribozymes and small hairpin RNA as specific examples, HEP, 2006, vol. 173, pp. 289-303.
Ghadessy et al., Directed evolution of polymerase function by compartmentalized self-replication, Proc Natl Acad Sci USA, 2001, vol. 98, No. 8, pp. 4552-4557.
Gu et al., A proximity-based programmable DNA nanoscale assembly line, Nature, 2010, vol. 465, pp. 202-205.
Helene et al., Control of gene expression by triple helix-forming oligonucleotides, Annals New York Academy of Sciences, 1992, vol. 660, pp. 27-36.
Holmes, Buy buy bispecific antibodies, Nature Reviews Drug Discovery, 2011, vol. 10, pp. 798-800.
Ichise et al., Imaging of β-cell mass and function, The Journal of Nuclear Medicine, 2010, vol. 51, pp. 1001-1004.
International Search Report and Written Opinion dated Nov. 13, 2014 in related Application No. PCT/US14/45832 filed Jul. 8, 2014 (11 pages).
Irwin et al., Zinc—A free database of commercially available compounds for virtual screening, J. Chem Inf Model, 2005, vol. 45, No. 1, pp. 177-182.
Katz et al., Enzyme-based logic systems for information processing, The Royal Soceity of Chemistry, 2010, vol. 39, No. 5, pp. 1835-1857.
Koren et al., Characterization of a monoclonal antibody that binds equally to all apolipoprotein and lipoprotein forms of human plasma apolipoprotein B.I. specificity and binding studies, Biochimica et Biophysica Acta, 1986, vol. 876, No. 1, pp. 91-100.
Lee et al., Biomarker discovery from the plasma proteome using multidimensional fractionation proteomics, Current Opinion in Chemical Biology, 2006, vol. 10, pp. 42-49.
Link et al., Beyond toothpicks: new methods for isolating mutant bacteria, Nature Reviews, 2007, vol. 5, No. 9, pp. 680-688.
Lipinski, Drug-like properties and the causes of poor solubility and poor permeability, Journal of Pharmacological and Toxicological Methods, 2000, vol. 44, pp. 235-249.
Liu et al., Ranking the susceptibility of disulfide bonds in human IgG1 antibodies by reduction, differential alkylation, and LC-MS analysis, Analytical Chemistry, 2010, vol. 82, No. 12, pp. 5219-5226 and 3 supplemental pages.
Lund et al., Molecular robots guided by prescriptive landscapes, Nature, 2010, vol. 465, pp. 206-210.
Maher, DNA triple-helix formation: an approach to artificial gene repressors?, BioEssays, 1992, vol. 14, No. 12, pp. 807-815.
Nelson et al., A multicolored set of in vivo organelle markers for co-localization studies in *Arabidopsis* and other plants, The Plant Journal, 2007, vol. 51, No. 6, pp. 1126-1136.
Nutiu, Structure-switching signaling aptamers: transducing molecular recognition into fluorescence signaling, Chemistry, 2004, vol. 10, No. 8, pp. 1868-1876.
Pei et al., Training a molecular automaton to play a game, Nature Nanotechnology, 2010, vol. 5, No. 11, pp. 773-777 and 142 supplemental pages.
Pushparaj et al., Short interfering RNA (siRNA) as a novel therapeutic, Clinical and Experimental Pharmacology and Physiology, 2006, vol. 33, pp. 504-501.
Qian et al., Neural network computation with DNA strand displacement cascades, Nature, 2011, vol. 475, pp. 368-372.
Reynolds et al., Rational siRNA design for RNA interference, Nature Biotechnology, 2004, vol. 22, No. 3, pp. 326-330.
Rinaudo et al., A universal RNAi-based logic evaluator that operates in mammalian cells, Nature Biotechnology, 2007, vol. 25, No. 7, pp. 795-801.
Rothemund, A DNA and restriction enzyme implementation of Turing Machines. DIMACS Series in Discrete Mathematics and Theo Comp Sci, 1996, vol. 27, pp. 75-119.
Rudchenko et al., Autonomous molecular cascades for evaluation of cell surfaces, Nature Nanotechnology, 2013, vol. 8, pp. 580-586.
Sagner et al., Rapid filter assay for the detection of DNA polymerase activity: direct identification of the gene for the DNA polymerase from Thermus acquaticus, Gene, 1991, Vo. 97, pp. 119-123.
Seelig et al., Enzyme-free nucleic acid logic circuits, Science, 2006, vol. 314, pp. 1585-1588.
Singelis et al., Horizontal and vertical dimensions of individualism and collectivism: a theoretical and measurement refinement, Cross-Cultural Research, 1995, vol. 29, No. 3, pp. 240-275.
Söderberg et al., Direct observation of individual endogenous protein complexes in situ by proximity ligation, Nature Methods, 2006, vol. 3, No. 12, pp. 995-1000.
Stojanovic et al., A deoxyribozyme-based molecular automation, Nature Biotechnology, 2003, vol. 21, pp. 1069-1074.
Stojanovic, et al., Exercises in molecular computing, Accounts of Chemical Research, 2014, vol. 47, No. 6, pp. 1845-1852.
Studier, Protein production by auto-induction in high-density shaking cultures, Protein Expression & Purification, 2005, vol. 41, No. 1, pp. 207-234.
Teillaud, Engineering of monoclonal antibodies and antibody-based fusion proteins: successes and challenges, Expert Opinion Biol Ther., 2005, vol. 5, No. 1, pp. S15-S27.
Tomizuka et al., Double trans-chromosomic mice: maintenance of two individual human chromosome fragments containing Ig heavy and $_k$loci and expression of fully human antibodies, Proceedings of the National Academy of Sciences, 2000, vol. 97, pp. 722-727.
Vlassov et al., Exosomes: Current knowledge of their composition, biological functions, and diagnostic and therapeutic potentials, Biochimica et Biophysica Acta., 2012, vol. 1820, No. 7, pp. 940-948.
Wang et al., All DNA finite-state automata with finite memory, Proceedings of the National Academy of Sciences, 2010, vol. 107, pp. 21996-22001.
Weiner et al., Monocolonal antibodies: versatile platforms for cancer immunotherapy, Nature Reviews Immunology, 2010, vol. 10, pp. 317-327.
Welte et al., Cancer stem cells in solid tumors, elusive or illusive?, Cell Communication and Signaling, 2010, vol. 8, No. 6, 10 pages.
Xie et al., Multi-input RNAi-based logic circuit for identification of specific cancer cells, Science, 2011, vol. 333, No. 6047, pp. 1307-1311.

(56) References Cited

OTHER PUBLICATIONS

Yurke et al., A DNA-fuelled molecular machine made of DNA, Nature, 2000, vol. 406, No. 6796, pp. 605-608.
Zhang et al., Dynamic DNA nanotechnology using strand-displacement reactions, Nature Chemistry, 2011, vol. 3, pp. 103-113.

* cited by examiner

YES-YES

GCAACTAGACTTCAGTATTCATATCCTTTCACAAT5'(0)
(1)5'CGTTGATCTGAAGTGCATAAGTATAGGAAAGTGTTA
  TTCACGTATTCATATCCTTTCACAATTCTTTCTCTATCTTCATTTCGG5'(2)--ab
  (3)5'GAAAGTGTTAAAGAAAGAGATTGAAGTAAATGCCTC
     TCTTTCTAACTTCATTTACGGAGCTATGCATTGGTTAGCATTC5'(4)--ab
     (5)5'AGTAAATGCCTCGATACGTAACCAAATCGTTAAGCC
        AGCTATGCATTGGTTTAGCAATTCGG5'(6)

YES-YES-YES

TAAGACCGATGCAACTAGACTTCAGTATTCATT5'(0)
(1)5'ATTCTGGCTACGTTGATCTGAAGTCATAAGTAA
  GCAACTAGACTTCAGTATTCATTCCTTTCACAAT5'(2)--ab
  (3)5'GTTGATCTGAAGTGCATAAGTAAGGAAAGTGTTA
     TTCACGTATTCATATCCTTTCACAATTCTTTCTCTATCTTCATTTCGG5'(4)--ab
     (5)5'GAAAGTGTAAAGAAAGAGATAGAAGTAAATGCCTC
        TCTTTCTCTAACTTCATTTACGGAGCTATGCATTGGTTAGCATTC5'(6)--ab
        (7)5'AGTAAATGCCTCGATACGTAACCAAATCGTTAAGCC
           AGCTATGCATTGGTTTAGCAATTCGG5'(8)

YES-NOT

TTCACGTATTCATATCCTTTCACAATTCTTTCTCTATCTTCATTTCGG5'(2)
(3)5'GAAAGTGTTAAAGAAAGAGATTGAAGTAAATGCCTC
   TCTTTCTCTAACTTCATTTACGGAGCTATGCATTGGTTTAGCATTTC5'(4)--ab
   (5*)5'AGTAAATGCCTGATACGTAACCAAATCGTTAAG
      AGCTATGCATTGGTTTAGCAATTCGG5'(6*)--ab
      (5)5'AGTAAATGCCTCGATACGTAACCAAATCGTTAAGCC
         AGCTATGCATTGGTTTAGCAATTCGG5'(6)

FIG. 4A

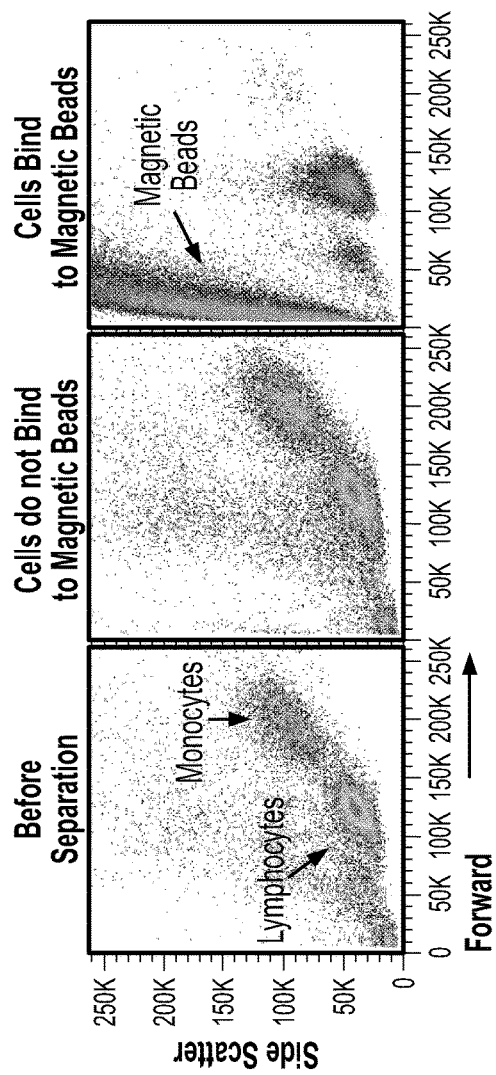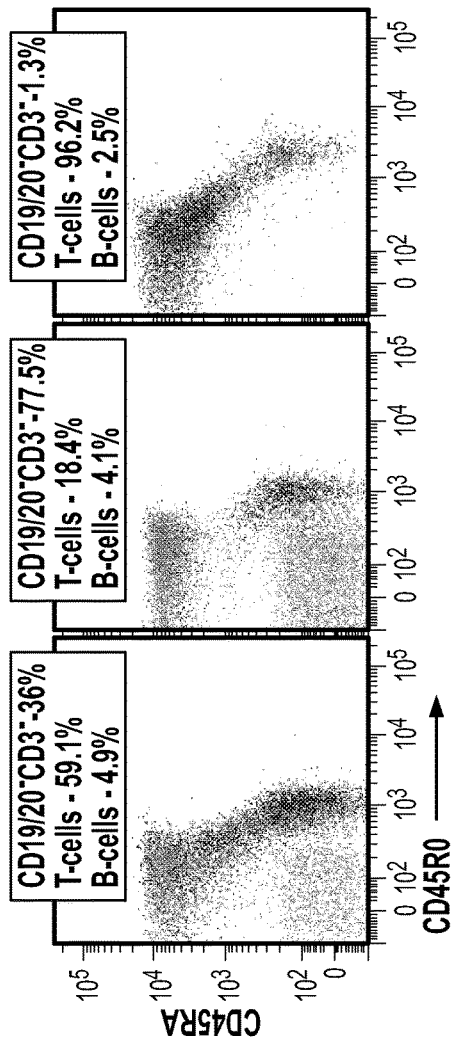

SEQUENCE LISTING

```
<160> NUMBER OF SEQ ID NOS: 24

<210> SEQ ID NO 1
<211> LENGTH: 36
<212> TYPE: DNA
<213> ORGANISM: Artificial Sequence
<220> FEATURE:
<223> OTHER INFORMATION: Synthetic nucleotide

<400> SEQUENCE: 1
ctaatgtgaa aggaagacag agttgtatgg gatgga                            36

<210> SEQ ID NO 2
<211> LENGTH: 36
<212> TYPE: DNA
<213> ORGANISM: Artificial Sequence
<220> FEATURE:
<223> OTHER INFORMATION: Synthetic nucleotide

<400> SEQUENCE: 2
gattacactt tccttctgtc tcaacatacc ctacct                            36

<210> SEQ ID NO 3
<211> LENGTH: 50
<212> TYPE: DNA
<213> ORGANISM: Artificial Sequence
<220> FEATURE:
<223> OTHER INFORMATION: Synthetic nucleotide

<400> SEQUENCE: 3
aggaagacag agttgtatgg gatggacata ttacgaatca cctatattga             50

<210> SEQ ID NO 4
<211> LENGTH: 36
<212> TYPE: DNA
<213> ORGANISM: Artificial Sequence
<220> FEATURE:
<223> OTHER INFORMATION: Synthetic nucleotide

<400> SEQUENCE: 4
taccctacct gtataatgct ttgtggatat tactga                            36

<210> SEQ ID NO 5
<211> LENGTH: 48
<212> TYPE: DNA
<213> ORGANISM: Artificial Sequence
<220> FEATURE:
<223> OTHER INFORMATION: Synthetic nucleotide

<400> SEQUENCE: 5
catattacga aacacctata atgactggac tgaatgggac aacatgat               48

<210> SEQ ID NO 6
<211> LENGTH: 36
<212> TYPE: DNA
<213> ORGANISM: Artificial Sequence
<220> FEATURE:
<223> OTHER INFORMATION: Synthetic nucleotide
```

<400> SEQUENCE: 6
ggatattact gacctgactt accctgttgt tctacc                                    36

<210> SEQ ID NO 7
<211> LENGTH: 26
<212> TYPE: DNA
<213> ORGANISM: Artificial Sequence
<220> FEATURE:
<223> OTHER INFORMATION: Synthetic nucleotide

<400> SEQUENCE: 7
ctggactgaa tgggacaaca agatgg                                              26

<210> SEQ ID NO 8
<211> LENGTH: 36
<212> TYPE: DNA
<213> ORGANISM: Artificial Sequence
<220> FEATURE:
<223> OTHER INFORMATION: Synthetic nucleotide

<400> SEQUENCE: 8
cgttgatctg aagtgcataa gtataggaaa gtgtta                                   36

<210> SEQ ID NO 9
<211> LENGTH: 50
<212> TYPE: DNA
<213> ORGANISM: Artificial Sequence
<220> FEATURE:
<223> OTHER INFORMATION: Synthetic nucleotide

<400> SEQUENCE: 9
ttcacgtatt catatccttt cacaatttct ttctctatct tcattttcgg                    50

<210> SEQ ID NO 10
<211> LENGTH: 36
<212> TYPE: DNA
<213> ORGANISM: Artificial Sequence
<220> FEATURE:
<223> OTHER INFORMATION: Synthetic nucleotide

<400> SEQUENCE: 10
gaaagtgtta aagaaagaga ttgaagtaaa tgcctc                                   36

<210> SEQ ID NO 11
<211> LENGTH: 48
<212> TYPE: DNA
<213> ORGANISM: Artificial Sequence
<220> FEATURE:
<223> OTHER INFORMATION: Synthetic nucleotide

<400> SEQUENCE: 11
ttctttctct aacttcattt acggagctat gcattggttt agcatttc                      48

<210> SEQ ID NO 12
<211> LENGTH: 36
<212> TYPE: DNA
<213> ORGANISM: Artificial Sequence
<220> FEATURE:
<223> OTHER INFORMATION: Synthetic nucleotide

<400> SEQUENCE: 12
gcaactagac ttcacgtatt catatccttt cacaat                                   36

```
<210> SEQ ID NO 13
<211> LENGTH: 51
<212> TYPE: DNA
<213> ORGANISM: Artificial Sequence
<220> FEATURE:
<223> OTHER INFORMATION: Synthetic nucleotide

<400> SEQUENCE: 13
ttcacgtatt catatccttt cacaatttct ctttctctat cttcatttcg g          51

<210> SEQ ID NO 14
<211> LENGTH: 36
<212> TYPE: DNA
<213> ORGANISM: Artificial Sequence
<220> FEATURE:
<223> OTHER INFORMATION: Synthetic nucleotide

<400> SEQUENCE: 14
agtaaatgcc tcgatacgta accaaatcgt taagcc                           36

<210> SEQ ID NO 15
<211> LENGTH: 26
<212> TYPE: DNA
<213> ORGANISM: Artificial Sequence
<220> FEATURE:
<223> OTHER INFORMATION: Synthetic nucleotide

<400> SEQUENCE: 15
agctatgcat tggtttagca attcgg                                      26

<210> SEQ ID NO 16
<211> LENGTH: 34
<212> TYPE: DNA
<213> ORGANISM: Artificial Sequence
<220> FEATURE:
<223> OTHER INFORMATION: Synthetic nucleotide

<400> SEQUENCE: 16
taagaccgat gcaactagac ttcacgtatt catt                             34

<210> SEQ ID NO 17
<211> LENGTH: 34
<212> TYPE: DNA
<213> ORGANISM: Artificial Sequence
<220> FEATURE:
<223> OTHER INFORMATION: Synthetic nucleotide

<400> SEQUENCE: 17
attctggcta cgttgatctg aagtgcataa gtaa                             34

<210> SEQ ID NO 18
<211> LENGTH: 36
<212> TYPE: DNA
<213> ORGANISM: Artificial Sequence
<220> FEATURE:
<223> OTHER INFORMATION: Synthetic nucleotide

<400> SEQUENCE: 18
gcaactagac ttcacgtatt catttccttt cagaat                           36

<210> SEQ ID NO 19
<211> LENGTH: 34
<212> TYPE: DNA
<213> ORGANISM: Artificial Sequence
<220> FEATURE:
<223> OTHER INFORMATION: Synthetic nucleotide
```

-continued

```
<400> SEQUENCE: 19
agtaaatgcc tcgatacgta accaaatcgt taag                        34

<210> SEQ ID NO 20
<211> LENGTH: 24
<212> TYPE: DNA
<213> ORGANISM: Artificial Sequence
<220> FEATURE:
<223> OTHER INFORMATION: Synthetic nucleotide

<400> SEQUENCE: 20
agctatgcat tggtttagca attc                                   24

<210> SEQ ID NO 21
<211> LENGTH: 50
<212> TYPE: DNA
<213> ORGANISM: Artificial Sequence
<220> FEATURE:
<223> OTHER INFORMATION: Synthetic nucleotide

<400> SEQUENCE: 21
ggcttttact tctatctctt tctttaacac tttcctatac ttatgcactt       50

<210> SEQ ID NO 22
<211> LENGTH: 24
<212> TYPE: DNA
<213> ORGANISM: Artificial Sequence
<220> FEATURE:
<223> OTHER INFORMATION: Synthetic nucleotide

<400> SEQUENCE: 22
cagtgcaagg ttaggtattg ctta                                   24

<210> SEQ ID NO 23
<211> LENGTH: 24
<212> TYPE: DNA
<213> ORGANISM: Artificial Sequence
<220> FEATURE:
<223> OTHER INFORMATION: Synthetic nucleotide

<400> SEQUENCE: 23
gtcacgttcc aatccataac gaat                                   24

<210> SEQ ID NO 24
<211> LENGTH: 21
<212> TYPE: DNA
<213> ORGANISM: Artificial Sequence
<220> FEATURE:
<223> OTHER INFORMATION: Synthetic nucleotide

<400> SEQUENCE: 24
aaggttaggt attgcttaga a                                      21
```

SELECTION OF BIOLOGICAL OBJECTS

CROSS-REFERENCE TO RELATED APPLICATIONS

The present application (1) is a continuation in part of International Application No. PCT/US14/45832 filed 8 Jul. 2014; which claims the benefit of U.S. Provisional Application Ser. No. 61/843,892 filed 8 Jul. 2013; and (2) claims the benefit of U.S. Provisional Application Ser. No. 62/074,796 filed 4 Nov. 2014; each of which is incorporated herein by reference in its entirety.

STATEMENT REGARDING FEDERALLY SPONSORED RESEARCH OR DEVELOPMENT

Not Applicable.

MATERIAL INCORPORATED-BY-REFERENCE

The Sequence Listing, which is a part of the present disclosure, includes a computer readable form comprising nucleotide and/or amino acid sequences of the present invention. The subject matter of the Sequence Listing is incorporated herein by reference in its entirety.

BACKGROUND OF THE INVENTION

Molecular automata are mixtures of molecules that undergo precisely defined structural changes in response to sequential interactions with inputs. Previously studied nucleic acid based automata include game-playing molecular devices (MAYA automata) and finite-state automata for analysis of nucleic acids with the latter inspiring circuits for the analysis of RNA species inside cells.

SUMMARY OF THE INVENTION

One aspect of the present disclosure provides a molecular automaton system for marking, isolation, selection, imaging, analysis, elimination, or treatment of a target biological object, such as a cell, subcellular organelle, subcellular vesicle, or extracellular vesicle. Some embodiments include modules specific for a target biological object having a first cell surface marker and a second cell surface marker. Some embodiments include modules specific for a target biological object having a first cell surface marker but not a second cell surface marker.

In some embodiments, target biological comprises a first object surface marker and a second surface marker. In such embodiments, the system (e.g., a yes/yes system) can include (a) a first target marker having (i) a first target-specific agent specific for the first object surface marker and (ii) a first double strand complex comprising a first oligonucleotide and a second oligonucleotide, the second oligonucleotide linked to the first target-specific agent. In such embodiments, the system can also include (b) a second target marker having (i) a second target-specific agent specific for the second object surface marker and (ii) a second double strand complex comprising a third oligonucleotide and a fourth oligonucleotide, the fourth oligonucleotide linked to the second target-specific agent. Such system embodiments can include (c) a single stranded fifth oligonucleotide; and (d) a single stranded sixth oligonucleotide linked to an isolation agent, a cytotoxic agent, or a therapeutic agent.

In the above embodiments (e.g., a yes/yes system), the first oligonucleotide has more complementarity for the fifth oligonucleotide than for the second oligonucleotide, such that when in proximity, the fifth oligonucleotide will disrupt the first double strand complex to form a single stranded second oligonucleotide and a third double strand complex comprising the first oligonucleotide and the fifth oligonucleotide; the third oligonucleotide has more complementarity for the second oligonucleotide than for the fourth oligonucleotide, such that when in proximity, the single stranded second oligonucleotide will disrupt the second double strand complex to form a single stranded fourth oligonucleotide and a fourth double strand complex comprising the second oligonucleotide and the third oligonucleotide, the fourth double strand complex linked to the first target-specific agent via the second oligonucleotide, and the single stranded fourth oligonucleotide linked to the second target-specific agent; and the sixth oligonucleotide has sufficient complementarity to the single stranded fourth oligonucleotide to form a fifth double strand complex therewith, but has insufficient complementarity for the fourth oligonucleotide to disrupt the second double strand complex.

In some embodiments, target biological comprises a first object surface marker but not a second surface marker. In such embodiments, the system (e.g., a yes/no system) can include (a) a first target marker having (i) a first target-specific agent specific for the first surface marker and (ii) a first double strand complex comprising a first oligonucleotide and a second oligonucleotide, the second oligonucleotide linked to the first target-specific agent. In such embodiments, the system can also include (b) a second target marker having (i) a second target-specific agentspecific for the second surface marker and (ii) a second double strand complex comprising a third oligonucleotide and a fourth oligonucleotide, the fourth oligonucleotide linked to the second target-specific agent. Such system embodiments can include (c) a single stranded fifth oligonucleotide; (d) a sixth double strand complex comprising a sixth oligonucleotide and a seventh oligonucleotide, the sixth oligonucleotide linked to an isolation agent, a cytotoxic agent, or a therapeutic agent.

In the above embodiments (e.g., a yes/no system), the first oligonucleotide has more complementarity for the fifth oligonucleotide than for the second oligonucleotide, such that when in proximity, the fifth oligonucleotide will disrupt the first double strand complex to form a single stranded second oligonucleotide and a third double strand complex comprising the first oligonucleotide and the fifth oligonucleotide; the third oligonucleotide has more complementarity for the second oligonucleotide than for the fourth oligonucleotide, such that when in proximity, the single stranded second oligonucleotide will disrupt the second double strand complex to form a single stranded fourth oligonucleotide and a fourth double strand complex comprising the second oligonucleotide and the third oligonucleotide, the fourth double strand complex linked to the first target-specific agentvia the second oligonucleotide, and the single stranded fourth oligonucleotide linked to the second target-specific agent; the sixth oligonucleotide has more complementarity for the second oligonucleotide than for the seventh oligonucleotide, such that when in proximity, the single stranded second oligonucleotide will disrupt the sixth double strand complex to form a single stranded seventh oligonucleotide and a seventh double strand complex comprising the second oligonucleotide and the sixth oligonucleotide, the seventh double strand complex linked to the first target-specific agentvia the second oligonucleotide, and the single stranded fourth oligonucleotide linked to the second target-specific agent; and the third oligonucleotide has more complementarity for the second oligonucleotide than the sixth oligonucleotide has for the second oligonucleotide, such that when in proximity, the sixth oligonucleotide cannot displace the third oligonucleotide from the fourth double strand complex comprising the second oligonucleotide and the third oligonucleotide.

Another aspect provides a method for isolating, eliminating, imaging, or treating a target biological object with the molecular automaton system of the present disclosure.

In some embodiments (e.g., a yes/yes system) the method includes (a) contacting the first target marker, the second target marker, and a population of biological objects optionally comprising the target biological object, the target biological comprising the first surface marker and the second surface marker, to form a marked target biological object; and (b) contacting the single stranded fifth oligonucleotide and the single stranded sixth oligonucleotide linked to the isolation agent, the cytotoxic agent, or the therapeutic agent with the marked target biological object.

In some embodiments (e.g., a yes/no system) the method includes (a) contacting the first target marker, the second target marker, and a population of biological objects optionally comprising the target biological object, the target biological object comprising the first surface marker but not second surface marker, to form a marked target biological object; and (b) contacting the single stranded fifth oligonucleotide and the sixth double strand complex linked to the isolation agent, the cytotoxic agent, or the therapeutic agent with the marked target biological object.

Various features are included in some embodiments of the system or method.

In some embodiments, the target biological object includes a cell, an organelle, or a vesicle.

In some embodiments, the target biological object includes a cell. In some embodiments, the target biological object comprises a stem cell, a leukocyte group, a granulocytes, a monocyte, a T lymphocyte, a T helper cell, a T regulatory cell, a cytotoxic T cell, a naïve T cell, a lymphocyte, a thrombocyte, or a natural killer (NK) cell. In some embodiments, the target biological object comprises an NK cell, a T-cell, or a B-cell.

In some embodiments, the target biological object is selected from the group consisting of an exosome, apoptotic bleb, shedding vesicle, microparticle, prostasome, tolerosome, prominosome, unilamellar liposome vesicle, or multilamellar liposome vesicle, vacuole, plant vacuole, contractile vacuole, lysosome, peroxisome, transport vesicle, secretory vesicle, synaptic vesicle, hormonal secretory vesicle, cell wall-associated vesicle, toxic membrane vesicle, signal molecule vesicle, gas vesicle, membrane vesicle, matrix vesicle, multivesicular body, outer membrane vesicle, mitochondria, plastic, flagellum, endoplasmic reticulum, Golgi apparatus, vacuole, nucleus, acrosome, autophagosome, centriole, cilium, eyespot apparatus, glycosome, glyoxosome, hydrogenosome, lysosome, melanosome, mitosome, myofibril, nematocyst, nucleolus, parenthesome, peroxisome, proteasome, ribosome, 80s ribosome, vesicle, nucleosome, microtubule, large RNA AND protein complex, ribosome, spliceosome, vault, proteasome, DNA polymerase III holoenzyme, RNA polymerase II holoenzyme, symmetric viral capsid, complex of GroEL and GroES, membrane protein complex, photosystem I, ATP synthase, large DNA and protein complex, nucleosome, centriole and microtubule-organizing center (MTOC), cytoskeleton, nucleolus, carboxysome, chlorosome, magnetosome, nucleoid, plasmid, ribosome, 70s ribosome, thylakoid, and mesasome.

In some embodiments, the target biological object is produced by or associated with a stem cell, a leukocyte group, a granulocytes, a monocyte, a T lymphocyte, a T helper cell, a T regulatory cell, a cytotoxic T cell, a naïve T cell, a lymphocyte, a thrombocyte, or a natural killer cell. In some embodiments, the target biological object is produced by or associated with an NK cell, a T-cell, or a B-cell.

In some embodiments, the target biological object is a stem cell and the first cell surface marker or the second cell surface marker is selected from the group consisting of CD34+, CD31−, and CD117. In some embodiments, the target biological object is a leukocyte group and the first cell surface marker or the second cell surface marker is CD45+. In some embodiments, the target biological object is a granulocyte and the first cell surface marker or the second cell surface marker is selected from the group consisting of CD45+, CD11b, CD15+, CD24+, CD114+, and CD182+. In some embodiments, the target biological object is a monocyte and the first cell surface marker or the second cell surface marker is selected from the group consisting of CD45+, CD14+, CD114+, CD11a, CD11b, CD91+, CD16+. In some embodiments, the target biological object is a T lymphocyte and the first cell surface marker or the second cell surface marker is selected from the group consisting of CD45+ and CD3+. In some embodiments, the target biological object is a T helper cell and the first cell surface marker or the second cell surface marker is selected from the group consisting of CD45+, CD3+, and CD4+. In some embodiments, the target biological object is a T regulatory cell and the first cell surface marker or the second cell surface marker is selected from the group consisting of CD4, CD25, and Foxp3. In some embodiments, the target biological object is a Cytotoxic T cell and the first cell surface marker or the second cell surface marker is selected from the group consisting of CD45+, CD3+, and CD8+. In some embodiments, the target biological object is a naïve T-cell and the first cell surface marker or the second cell surface marker is selected from the group consisting of CD45RA+ and CD3+. In some embodiments, the target biological object is a B lymphocyte and the first cell surface marker or the second cell surface marker is selected from the group consisting of CD45+, CD19+ or CD45+, CD20+, CD24+, CD38, and CD22. In some embodiments, the target biological object is a Thrombocyte and the first cell surface marker or the second cell surface marker is selected from the group consisting of CD45+ and CD61+. In some embodiments, the target biological object is a Natural killer cell and the first cell surface marker or the second cell surface marker is selected from the group consisting of CD16+, CD56+, CD3−, CD31, CD30, and CD38.

In some embodiments, the first target-specific agent comprises a first antibody specific for the first object surface marker; and the second target-specific agent comprises a second antibody specific for the second object surface marker. In some embodiments, the first target-specific agent comprises a first monoclonal antibody specific for the first object surface marker; and the second target-specific agent comprises a second monoclonal antibody specific for the second object surface marker.

In some embodiments, the first object surface marker or the second object surface marker is selected from the group consisting of a Type 1 receptor, Type 2 G protein-coupled receptor, Type 3 kinase linked receptor, and Type 4 nuclear receptor. In some embodiments, the first object surface marker or the second object surface marker is selected from the group consisting of an immune receptor, pattern recognition receptor (PRR), Toll-like receptor (TLR), killer activated and killer inhibitor receptor (KAR and KIR), complement receptor, Fc receptor, B cell receptor, T cell receptor, cytokine receptor, ion channel linked receptor, nicotinic acetylcholine receptor, glycine receptor, GABA receptor, GABA-A receptor, GABA-C receptor, glutamate receptor, NMDA receptor, AMPA receptor, Kainate receptor, 5-HT3 receptor, P2× receptor, cyclic nucleotide-gated ion channel, IP3 receptor, intracellular ATP receptor, and ryanodine receptor.

In some embodiments, the first object surface marker or the second object surface marker is selected from the group consisting of a clathrin coat-associated marker, COPI coat-associated marker, COPII coat-associated marker, coatomer coat-associated marker, SNARE marker, v-SNARE, t-SNARE, Qa SNARE, Qb SNARE, Qc SNARE, and R SNARE.

In some embodiments, the first object surface marker or the second object surface marker is a small molecule selected from the group consisting of a steroid or nitrophenol compound.

In some embodiments, the first oligonucleotide, the second oligonucleotide, the third oligonucleotide, the fourth oligonucleotide, the fifth oligonucleotide, the sixth oligonucleotide, or the seventh oligonucleotide comprise about 10 to about 100 nucleotides. In some embodiments, the first oligonucleotide, the second oligonucleotide, the third oligonucleotide, the fourth oligonucleotide, the fifth oligonucleotide, the sixth oligonucleotide, or the seventh oligonucleotide comprise about 10, about 15, about 20, about 25, about 30, about 35, about 40, about 45, about 50, about 55, about 60, about 65, about 70, about 75, about 80, about 85, about 90, about 95, or about 100 nucleotides.

In some embodiments, oligonucleotide complementarity comprises about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45%, about 50%, about 55%, or about 60%.

In embodiments, a double strand complex comprises a pair of oligonucleotides having a difference in nucleotide number selected from the group consisting of about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, and about 25 nucleotides; and the difference in nucleotide number creates a toe hold sufficient to drive a strand-displacement reaction.

In some embodiments, the target biological object is isolated according to flow cytometry, fluorescence-activated cell sorting (FACS), magnetic-activated cell sorting (MACS), Cytometric Bead Array (CBA), magnetic-activated cell sorting (MACS), a magnetic nanoparticle coated with an anti-fluorochrome antibody, superparamagnetic spherical polymer particles, polymer beads coated with an anti-fluorochrome antibody, avidin, or streptavidin, or plasmapheresis.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 1A shows magnetic separation of PBMCs based on results of a YESCD45YESCD3 automaton. Before the cascade (left panel), the mixture of cells is observed with different CD3+ status. After the cascade, cells were incubated with magnetic microbeads conjugated with anti-FITC antibodies (MiltenyiBiotec) and applied on a MACS Column (MiltenyiBiotec; isolated purity of preparation was >95%). The "pass through" fraction (blue line in middle panel) and magnetically labeled cells (red line in middle panel) were re-analyzed with different clones of αCD3 antibodies to confirm purity (right panel). FIG. 1B shows YESCD3YESCD8 automaton was demonstrated in whole blood: Flow cytometry analysis with gating strategy shown (left and middle left panels); nucleated cells were gated based on staining their DNA with 7-AAD, with lymphocytes selected based on forward and side scatter; The histograms show two steps of the cascade as performed in blood, Cy5 fluorescence is used to show that first step was accomplished, while fluorescein is used to demonstrate that the second step was accomplished, as in FIG. 10A-FIG. 10C). Lines on histograms: yellow—unlabeled blood sample; green—blood sample incubated for 15 min with αCD3 conjugated with duplex 1•2-Cy5 and αCD8 conjugated with duplex 3.4; blue—same, but with F–5•6-Q added and also incubated for 15 min; red—subsequent addition of 0-Q.

FIG. 3A depicts unwanted double helix formation between oligonucleotide 2 (SEQ ID NO: 9) and oligonucleotide 3 (SEQ ID NO: 10). FIG. 3B depicts the addition of a mismatch to make the steps in formation of a double helix between oligonucleotide 2 (SEQ ID NO: 9) and oligonucleotide 3 (SEQ ID NO: 10) less energetically favorable, and hence reduce the amount of unwanted double helix formation. When no mismatches were present in full cascade experiments, unwanted leakage of fluorescence signal was more pronounced. When a mismatch(es) was strategically introduced, unwanted leakage was significantly diminished, see e.g., FIG. 2, for an example of experiment results. (1) is SEQ ID NO: 8, (2) is SEQ ID NO: 9, (3) is SEQ ID NO: 10, and (4) is SEQ ID NO: 11.

FIG. 4A-FIG. 4E is a series of DNA sequences and drawings showing oligonucleotide sequences. FIG. 4A shows oligonucleotide sequences where NB strand labels do not coincide with one another across different cascades. For example, strand (2) (SEQ ID NO: 13) in the YES-YES cascade is not the same as strand (2) (SEQ ID NO: 18) in the YES-YES-YES cascade. Also, color-coding does not coincide across different cascades. For example, strand (0) (SEQ ID NO: 12) in the YES-YES cascade is not the same as strand (2) (SEQ ID NO: 18) in the YES-YES-YES cascade. Hashed lines indicate mismatches. Letters "ab" represent an antibody conjugate to oligonucleotide. YES-YES: (0) is SEQ ID NO: 12; (1) is SEQ ID NO: 8; (2) is SEQ ID NO: 13; (3) is SEQ ID NO: 10, (4) is SEQ ID NO: 11; (5) is SEQ ID NO: 14; and (6) is SEQ ID NO: 15. YES-YES-YES: (0) is SEQ ID NO: 16; (1) is SEQ ID NO: 17; (2) is SEQ ID NO: 18; (3) is SEQ ID NO: 8, (4) is SEQ ID NO: 9; (5) is SEQ ID NO: 10; (6) is SEQ ID NO: 11; (7) is SEQ ID NO: 14; and (8) is SEQ ID NO: 15. YES-NOT: (2) is SEQ ID NO: 9; (3) is SEQ ID NO: 10; (4) is SEQ ID NO: 11; (5*) is SEQ ID NO: 19, (6*) is SEQ ID NO: 20; (5) is SEQ ID NO: 14; and (6) is SEQ ID NO: 15. FIG. 4B-FIG. 4E show various forms of cascades considered in the initial design phase. FIG. 4B is the basis for current cascades. It was taken into consideration that oligonucleotide 3 should be transferred in-between markers on the same cell, i.e., without diffusion. FIG. 4C shows a design using a long oligonucleotide complex that gets slowly degraded (sequential strip-off) by sequential interactions with oligonucleotides on the surface of the cell. The design can possibly diffuse away from the cell and hit non-target cells (bystander effect). FIG. 4D shows a similar design as FIG. 4C, but the oligonucleotide may not leave the surface. This design would also involve a very long linear DNA complex, which could be less favored in later in vivo studies and sequence optimization. FIG. 4E shows a variant of FIG. 4A. But the variant was not pursued due to the possibility of diffusion of 2 from cell and strong bystander effect.

FIG. 6A is a schematic showing automata operating on a targeted, e.g., B cell with C45$^+$CD20$^+$ phenotype, and non-targeted, e.g., T cells with CD45$^+$CD20$^-$ phenotype. Oligonucleotide components (colored horizontal lines) attached to antibodies (Y-shaped structures) are brought together on some cells and not others (for example, αCD45-1•2 and αCD20-3•4 are together only on B cells), leading to a cascade of oligonucleotide transfers driven by an increase in complementarity. The transfers result in a unique oligonucleotide (4) being displayed only on targeted cells. FIG. 6B is a schematic showing a typical strand displacement reaction used in the automata: 0+1•2+3•4→0•1+2•3+4, controlled via a sequential exposure of toeholds (T1 then T3): single-stranded oligonucleotide 0 displaces oligonucleotide 2 from its complex with 1 via toehold interactions (T$_1$). This generates a new toehold T$_3$ in strand 2 that can extend the reaction cascade by displacing oligonucleotide 4 from 3•4 to generate the next toehold T$_5$ on 4. T$_5$ can be used to extend the cascade to 5•6 (not shown) and so on (as indicated by double dotted arrows) or label the cell with 4. Without T$_3$, the cascade stops. FIG. 6C shows an example of oligonucleotide sequences used in the automata (0 is SEQ ID NO: 12; 1 is SEQ ID NO: 8; and 2 is SEQ ID NO: 21).

FIG. 10A shows a schematic representation of YESCD45YESCD20 automata with the reaction: 0+1•2$_{αCD45}$+3•4$_{αCD20}$+5•6→0•1+$_{αCD45}$2•3+$_{αCD20}$4•5+6 occurring on the cell surface: 1 is labeled with Cy5 and 0 labeled with a quencher (Q) for Cy5; 5 is labeled with fluorescein (F), and 6 labeled with a quencher (Q) for fluorescein. FIG. 10B shows flow cytometry monitoring of the YESCD45YESCD20 cascade (each dot represents the fluorescence signal level from a single cell at the time of measurement, with the dot density representing number of cells, shown as increasing from blue-through-red): time course of the cascade reaction on CD20$^+$ B-cells. The left panel shows removal of Cy5-1 after the triggering reaction with 0 monitors the removal of 1 occurring on CD45$^+$ cells. The right panel shows fluorescein-labeled 5 is taken up from solution by CD20$^+$ B-cells—this is used for monitoring the acquisition of F–5 by 4 enabled by prior removal of 3 from 4. The addition of 5•6 (indicated by first red arrow) produces an immediate fluorescence increase on all cells due to non-complete quenching of fluorescein; the addition of 0 (indicated by the second red arrow) triggers the cascade and separation of the subpopulations of cells. FIG. 10C shows the monitoring of a cascade on individual subpopulations within PBMCs by using fluorescently labeled monoclonal antibodies with non-overlapping epitopes for identification of cell subpopulations (PerCP-CD45 antibody, clone 2D1 and Pacific Blue-CD20 antibody (clone 2H7). These results confirm that all CD45$^+$CD20$^+$ cells (right gate, i.e., right box on bottom left panel) are labeled by automata (i.e., an increase was observed in fluorescein uptake from solution, cf. bottom middle and right panels) and that cells that are CD45$^+$CD20$^-$ (left gate, i.e., left box on bottom left panel) are not (upper left and central panels). It was observed that ~0.5% of cells that are gated (box at the central up panel) as CD45+CD20− may react with a delay (upper right panel). Arrows have the same meaning as under FIG. 10B.

FIG. 11A shows a schematic representation of YESCD45YESCD3. The reaction is $0+1\cdot2_{\alpha CD45}+3\cdot4_{\alpha CD3}+5\cdot6 \rightarrow 0\cdot1_{\alpha CD45}2\cdot3+_{\alpha CD3}4\cdot5+6$, where 1 is labeled with Cy5 and 0 labeled with a quencher for Cy5, and 5 is labeled with fluorescein and 6 labeled with a quencher for fluorescein. FIG. 11B shows flow cytometry results for the cascade depicted in FIG. 11A, i.e., monitoring the kinetics of the cascade reaction on CD3+T-cells—left panel—removal of Cy5-labeled 1 after triggering reaction with 0; and right panel—picking up of fluorescein-labeled 5 from solution by CD3+T-cells (events are arrowed, that is, addition of 5•6 is followed by addition of 0). FIG. 11C shows flow cytometry results for YESCD3YESCD20 demonstrating no labeling of cells that do not have both markers, i.e. negative control (cf., FIG. 13). FIG. 11D shows flow cytometry results for YESCD3YESCD8: positive control for panel FIG. 11C. FIG. 11E shows flow cytometry results for YESCD45(YESCD20ORYESCD3) selectively labeling two cell populations (B- and T-cells) (upper right-hand side) using an OR function.

FIG. 15A shows a schematic representation of a YESCD8NOTCD45RA cascade protecting naïve CD8+CD45RA+ T-cells in which the CD45RA isoform prevents the targeting of CD8. This automaton works by If cell is CD8 positive and If cell is CD45RA positive (and CD45RO$^{neg}$) then reaction is $2+3\cdot4_{\alpha CD8}+5\cdot\cdot6*_{\alpha CD45RA}+5\cdot6 \rightarrow 2\cdot3+5\cdot\cdot4_{\alpha CD8}+6*_{\alpha CD45RA}+5\cdot6$, resulting in no labeling (red trace on right panel of FIG. 15B), else, when cell is CD45RA− (CD45RO isoform), the reaction is: $2+3\cdot4_{\alpha CD8}+5\cdot6 \rightarrow 2\cdot3+5\cdot4_{\alpha CD8}+6$. As a result, fluorescein is taken up from the solution in a simple YESCD8 response (blue trace on right panel of FIG. 15B). FIG. 15B shows the monitoring of the YESCD8NOTCD45RA cascade. The left panel shows time-course of cascade reaction on the surface of CD8+ T-cells from peripheral blood: Right panel, histograms (or frequency distributions) of memory CD8+T-cells responding to automata (upper gate/box on left panel; blue trace on right panel, CD8+CD45RO+ or CD45RA−) while naïve CD8+ T-cells are being protected from automata (lower gate/box on left panel; red trace, CD8+CD45RO−/CD45RA+). For gating strategy, see e.g., FIG. 16A-FIG. 16B.

FIG. 16A shows the gating strategy during the analysis of a YESCD8NOTCD45RA cascade protecting naïve CD8+CD45RA+ T-cells. Anti-CD19 antibody was used to focus observation on CD19− cells (B-cells are CD19+, while non-B cells, that is, largely T-cells in this sample, are CD19−); then anti CD4 antibody was used to focus on CD4− cells within CD19− subpopulation, that means that population that was observed was mostly CD8+ (some NK cells were present as well) because CD8 and CD4 are mutually exclusive (on over >95% of cells) T-cells. FIG. 16B shows the distribution of CD45RA and CD45RO on human lymphocytes.

FIG. 17A shows individual antibodies are conjugated to components of the cascade (e.g., $\alpha_{CD45}$− with 1•2 complex, $\alpha_{CD3}$ with 3•4, and $\alpha_{CD8}$ with 5•6), while oligonucleotides are labeled with fluorescent dyes and quenchers to facilitate monitoring of multiple events in parallel (1 with Pacific Blue or PB, 3 with Cy5, 7 with fluorescein or F; 0, 2, and 8 with quenchers). FIG. 17B shows flow-cytometry monitoring in three colors of the state transition (y-axis: fluorescence intensity, x-axis: time, with arrows showing events, i.e., the additions of oligonucleotides 7•8 and 0. In the final step (right panel—fluorescein), the separation of CD45+CD3+CD8+ from all other lymphocytes is clearly shown. Arrows have the same meaning as under FIG. 10B, except herein F−7•8-Q was added.

In FIG. 21A showing strand exchange reaction cascades 1+2*3→1*2+3 (1 is SEQ ID NO: 22; 2 is SEQ ID NO: 23; and 3 is SEQ ID NO: 24), red toehold initiates the exchange, also leading to an irreversible (thermodynamically favorable) reaction. FIG. 21B shows schematics of a typical basic strand displacement reaction in solution as in A. Single-stranded oligonucleotide 1 displaces oligonucleotide 3 from its complex with 2, based on a stronger complementarity of 1*2 over 2*3. The reaction proceeds rapidly by toehold interactions (red To). The resulting single-stranded 3 can again react, extending the reaction cascade, e.g., with 4*5 complex (as shown in FIG. 21C displacing the next oligonucleotide 5, in analogy to 1 displacing 3. Light blue To' is a new toehold being formed—without it there will be no further reaction in this embodiment. FIG. 21C shows the principle of NOT cascades, also used for thresholding (NOT is equivalent to a very high threshold): NOT and thresholding are based on having two competitive displacement reactions, one with high, the other with low reaction rates. The one with higher reaction rates (or higher local concentration) would prevail, and stop the other one from happening (NOT). Different reaction rates can be based on different lengths (number of bases) of toeholds ($T_6$ vs. $T_8$ in $4_6$ vs. $4_8$, that are in $4_8*5$ and $4_6*5-R$, with R as a tag). Reaction rates can be controlled based on toehold sizes over several orders of magnitude.

FIG. 22A shows individual antibodies are conjugated to components of the cascade (e.g., αCD45– with 2*3 complex, αCD3 with 4*5, and αCD8– with 6*7), while oligonucleotides are labeled with fluorescent dyes (2 with Pacific Blue or PB, 4 with Cy5, 8 with fluorescein or F; 1, 3, and 9 with quenchers) and quenchers to facilitate monitoring. FIG. 22B, shows flow-cytometry monitoring in three colors of the cascades on cell surfaces (y: intensity of fluorescence, x—time, with arrows showing events, i.e., the addition of oligonucleotides 8*9 and then 1. With fluorescein the separation of CD8+ from other lymphocytes is seen.

FIG. 23A shows YESCD8YESCD45RO cascade (I) targets memory T-cells. Toxin-6 is also coupled to fluorescein, in order to monitor the reaction. FIG. 23B shows YESCD8NOTCD45RO cascade (II) protecting memory T-cells; the competition between elements on the surface of the cell and in solution leads to the suppression of the signal.

FIG. 25A-FIG. 25F is a series of flow cytometry graphs showing separation of naïve T-cells with a Y ESCD45RAYESCD3 module. FIG. 25A shows flow-cytometry prior to separation. FIG. 25B shows that cells not exposed to module do not bind to magnetic beads. FIG. 25C shows cells exposed to the module bind to magnetic beads. FIG. 25D shows flow-cytometry of a sample of control cells not exposed to module and not exposed to magnetic beads prior to separation, where 36% are CD19/20⁻CD3⁻, 59.1% are T-cells, and 4.9% are B-cells. FIG. 25E shows flow-cytometry of a sample of control cells not exposed to module and exposed to magnetic beads, where 77.5% are CD19/20⁻CD3⁻, 18.4% are T-cells, and 4.1% are B-cells. FIG. 25F shows flow-cytometry of a sample of cells exposed to module and exposed to magnetic beads, where 1.3% are CD19/20⁻CD3⁻, 96.2% are T-cells, and 2.5% are B-cells.

DETAILED DESCRIPTION OF THE INVENTION

Figure 1A:
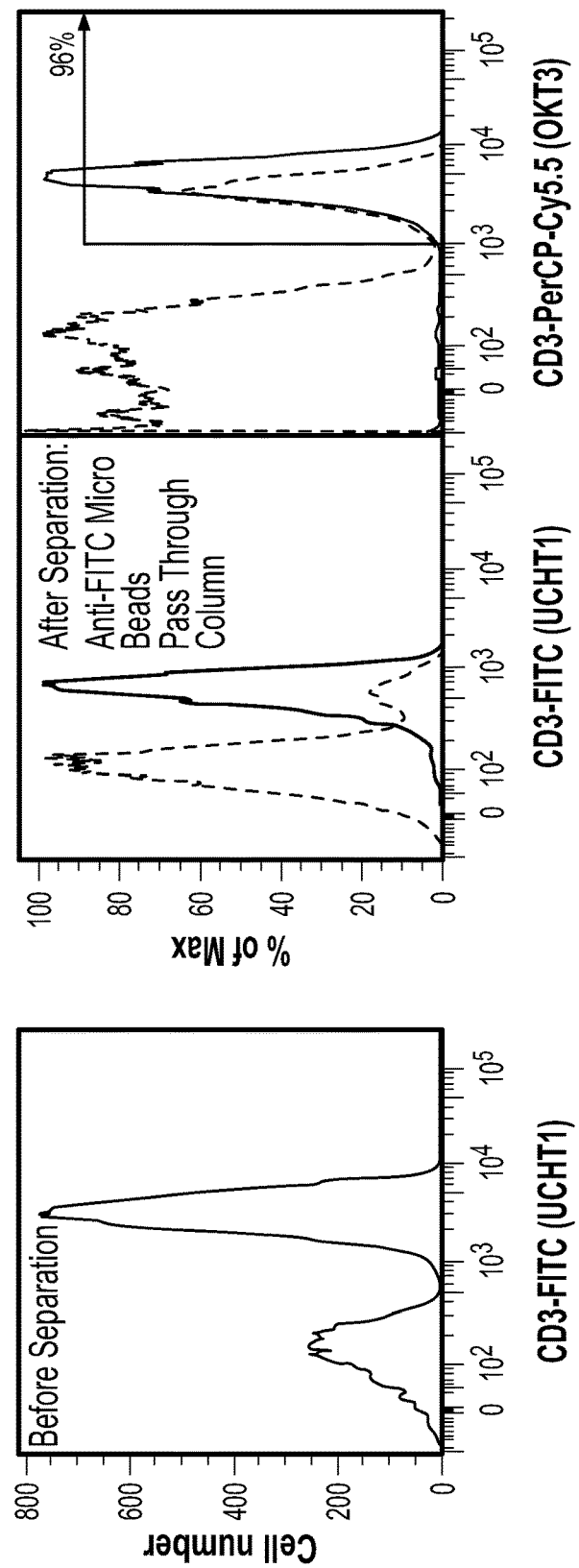
FIG. 1A-FIG. 1B is a series of spectra showing demonstrations of potential for practical applications.

The present disclosure is based, at least in part, on the discovery that molecular automata based on oligonucleotide strand-displacement cascades directed by chemical agents (e.g., an antibody) specific for surface markers can analyze a target biological object (e.g., a cell or an intracellular, extracellular, or subcellular biological component, such as an organelle, an intracellular vesicle, or an extracellular vesicle) by using surface markers as inputs. In short, a cascade of oligonucleotide transfers driven by an increase in complementarity is exploited between a series components (e.g., a first single stranded oligonucleotide; a first target specific agent (e.g., an antibody) coupled to second oligonucleotide and third oligonucleotide). Such an approach can be accomplished while minimizing or avoiding diffusion or cross-linking.

While strand displacement reactions are known (see e.g., Yurke et al. 2000 Nature 406, 605-608; Seelig et al. 2006 Science 314, 1585-1588; Qiau et al. 2011 Nature 475, 368-372; Rinaudo et al. 2007 Nature Biotechnology 25, 795-801; Xie et al. 2011 Science 333, 1307-1311), each of these approaches are directed to solution-phase analysis and regulation of protein expression. Various embodiments of the present disclosure use logical operations unrelated to the logic gates of prior approaches or cascades can follow a different algorithm (e.g., avoid diffusion away from cells or an intracellular, extracellular, or subcellular component or cross-linking).

While a nanobox that opens as a result of interactions between aptamers open up DNA nano-objects are known (e.g., Brand et al 2010 J Immunol 185, 2285-2294), such an approach relies on an equilibrium process within structure switching aptamers (see Nutiu 2004 Chemistry 10, 1868-1876) and therefore a significant proportion of the nano-objects would open even in the absence of targeted cells. Furthermore, embodiments described herein provide for longer cascades, thresholds, protective "NOT" elements, or an intermediate resembling a proximity ligation process.

An output (e.g., a final output) of a molecular automaton that successfully completes its analysis can be the presence of a unique molecular tag on the target biological object surface. As shown herein, an output (e.g., a final output) of a molecular automaton that successfully completes its analysis can be the presence of a unique molecular tag on the cell surface of a specific subpopulation of lymphocytes within human blood cells. Such an approach can be used for a variety of markers and biological object types. Various approaches described herein can overcome problems associated with proximity principles, such as bi-specific antibodies or proximity ligation reactions.

Labeling a narrow subpopulation within a much larger population of related biological objects can be problematic because of the need to specifically tag a particular object type for the purpose of marking, isolation, selection, imaging, analysis, or elimination. The problem can be addressed in a direct manner for a targeted subpopulation of biological objects having a unique surface marker against which antibodies can be raised. But, as best illustrated through an example of labeling cancer cells or vesicles (e.g., extracellular vesicles) produced by cancer cells with a surface marker (e.g., an antibody or antibody-drug conjugates (ADCs)), markers can be shared with non-targeted objects (e.g., cells or vesicles) and can lead to cross contamination or dose-limiting toxicities. To uniquely target biological objects that may not have a distinctive marker on their surfaces, a plurality of markers for a subpopulation of biological objects can be used in a Boolean (i.e., a logical combinatorial system that represents relationships between entities) manner. Molecular automata with structural changes (e.g., state transitions) can be coupled to the sequential recognition of a selected set of biological object surface markers and can contract the set into a single tag and thus can provide a unique handle for the targeted biological objects. In other words, various molecular devices described herein can autonomously evaluate Boolean functions on a biological object surface with a plurality of surface markers as inputs and a tag as an output.

In some embodiments, a molecular automata described herein can be used by transfecting oligonucleotides into cell lines, which can permit new operations on native cells.

Molecular automata in conventional cell analysis approaches using molecular robotics, complexity of individual nanoparticles is increased using self-assembly of DNA nanoobjects displaying multiple aptameric locks. Described herein is a potentially simpler alternative. Molecular automata described herein can interact with a biological object surface to execute more complex programmable (automata) functions, an approach that is conceptually similar to that of distributed robotics paradigms.

Target Markers

As described herein, a molecular automaton system for marking, isolation, selection, imaging, analysis, or elimination of a target biological object will generally include a plurality of target markers. A target marker can include a oligonucleotide specific for a strand-displacement cascade optionally coupled to a target specific agent (e.g., an antibody) specific for a surface marker of a target biological object or optionally coupled to a therapeutic agent. In some target markers, an oligonucleotide specific for a strand-displacement cascade is not coupled to another molecule.

A cascade of oligonucleotide transfers driven by an increase in complementarity is exploited between a series of target markers (e.g., a first single stranded oligonucleotide; a first target specific agent, such as an antibody, coupled to second oligonucleotide and third oligonucleotide). Various combinations of target markers operating in various logical operations are described throughout the present disclosure.

In some embodiments, an elementary unit of a strand displacement reaction (oligonucleotides 1 and 2*3 and reaction: $1+2*3 \rightarrow 1*2+3$) can be extended, leading to a cascade, i.e., reactions of a type: $1+2*3+4*5+6*7+8*9+ \ldots \rightarrow 1*2+3*4+5*6+7*8+9+$. Structures of oligonucleotides can be optimized and targeted mismatches introduced so as to, for example, minimize background reaction rates (i.e., interactions without introducing 1 to initiate reactions) or off-target effects.

Target Biological Objects

As described herein, molecular automata based on oligonucleotide strand-displacement cascades directed by a target specific agent (e.g., an antibody) can analyze biological objects by using their surface markers as inputs. As such, a target biological object can be any biological object having some unique combination (or absence) of surface markers not generally possessed by other objects (e.g., a cell or cell type or an intracellular, extracellular, or subcellular biological component, such as an organelle, an intracellular vesicle, or an extracellular vesicle). A target biological object can be a cell or cell type. A target biological object can be an intracellular, extracellular, or subcellular biological component, including but not limited to an organelle or a vesicle. A target biological object can be an intracellular biological component. A target biological object can be an extracellular biological component. A target biological object can be a subcellular biological component. A target biological object can be an organelle. A target biological object can be a vesicle.

Target Cells.

As described herein, molecular automata based on oligonucleotide strand-displacement cascades directed by antibodies can analyze cells by using their cell-surface markers as inputs. As such, a target cell can be any cell having some unique combination (or absence) of cell surface markers not generally possessed by other cells, e.g., cells in the same or similar tissues.

Exemplary target cells include stem cells, leukocyte groups, granulocytes, monocytes, T lymphocytes, T helper cells, T regulatory cells, Cytotoxic T cells, lymphocytes, thrombocytes, and natural killer cells.

Figure 19:
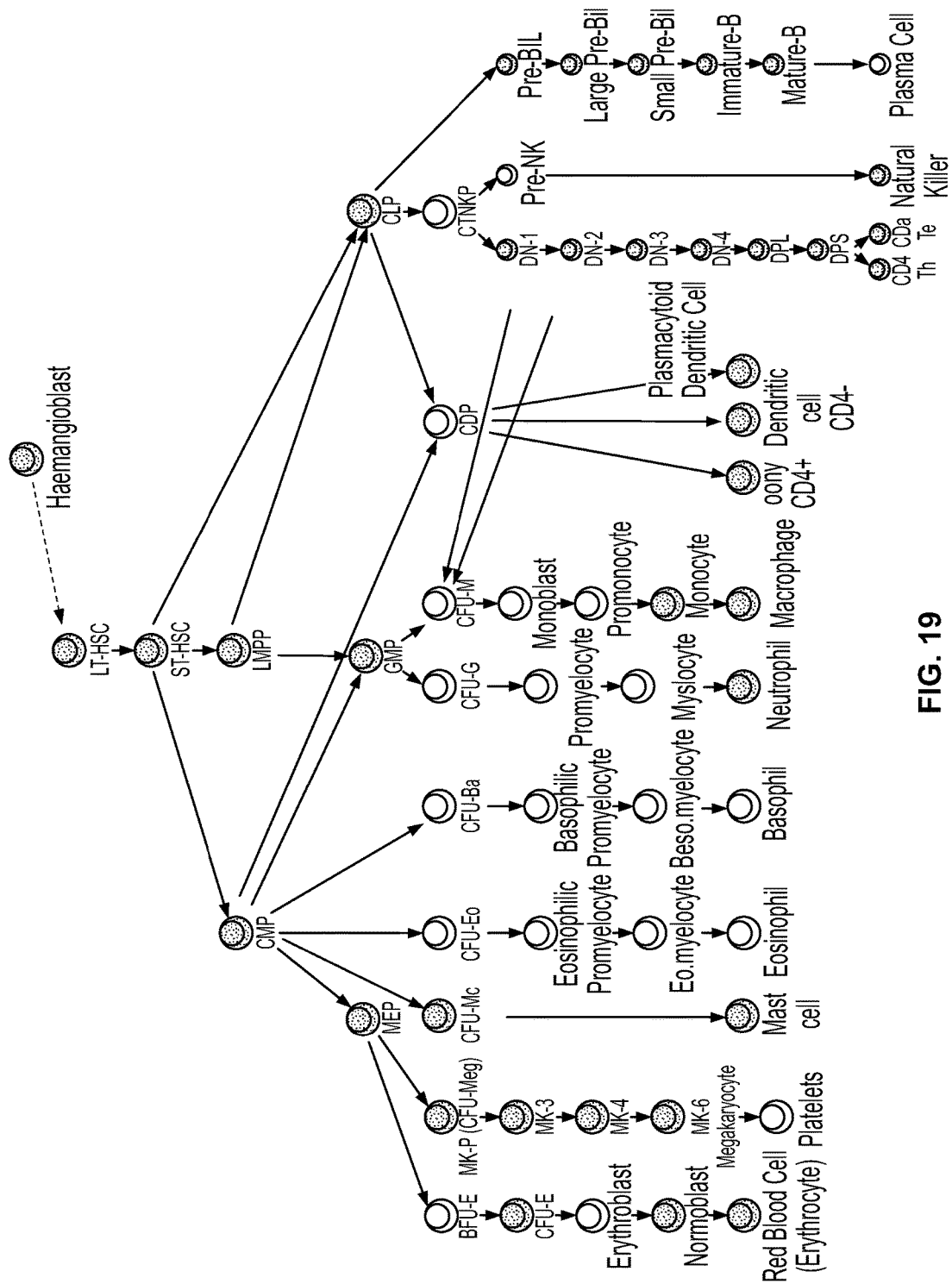
FIG. 19 is an illustration of lineages from hemangioblast precursor cells that include lymphocytes.
Figures 20, 21A:
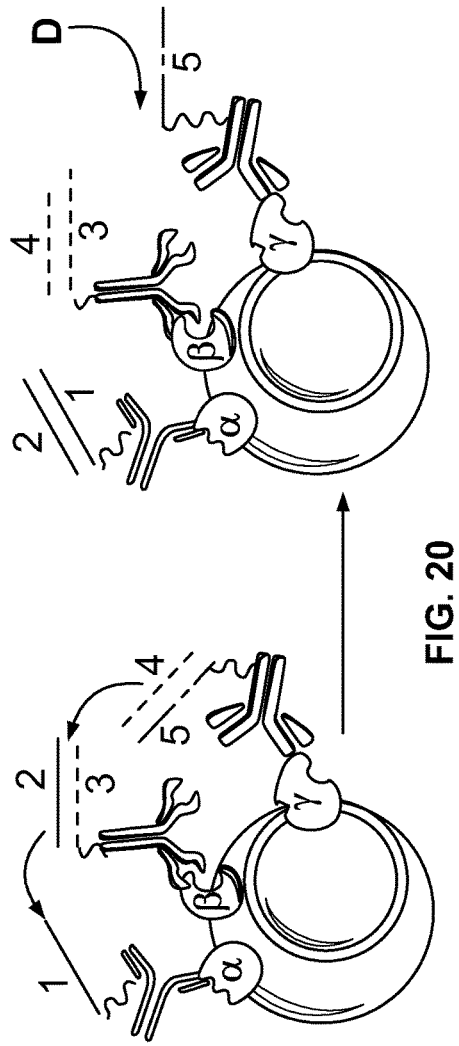
FIG. 20 is an illustration of cascades on cell surfaces connected with "action modules". Three surface markers ($\alpha$, $\beta$, $\gamma$) interact with targeting moieties (antibodies, their fragments, aptamers or peptide ligands). Oligonucleotides coupled to these moieties participate in reaction cascades on the cell surface ($\alpha1+\beta2*3+\gamma5*4 \rightarrow \alpha1*2+\beta3*4+\gamma5$), leading to a display of a new oligonucleotide (5) on the surface. This oligonucleotide can interact with drug delivery or imaging modules (D) leading to the elimination or labeling of targeted cells.
FIG. 21A-FIG. 21C is an illustration of oligonucleotide sequences used in strand exchange reaction cascades.
Figure 21B:
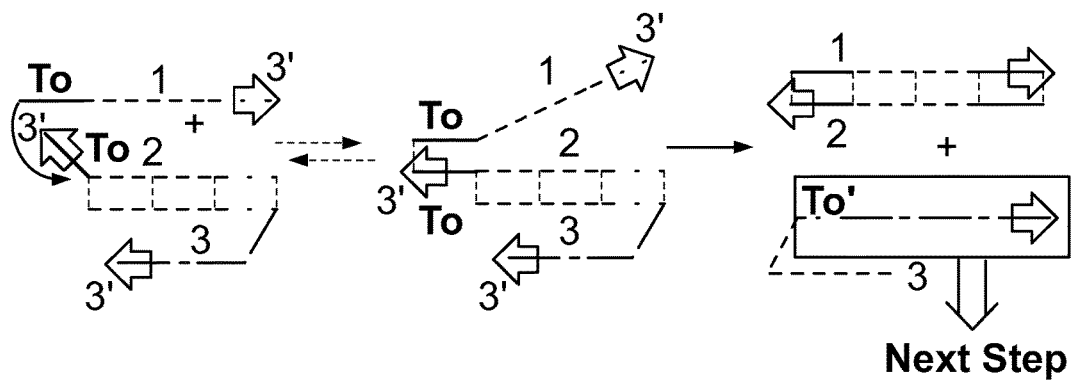
Figure 21C:
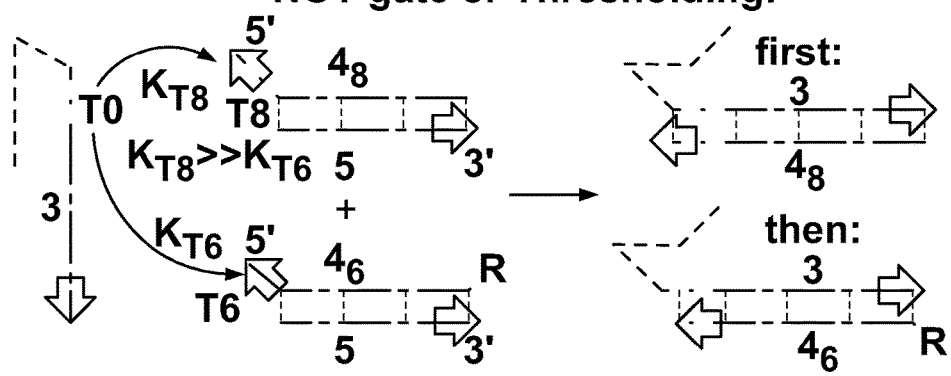
Figure 22A:
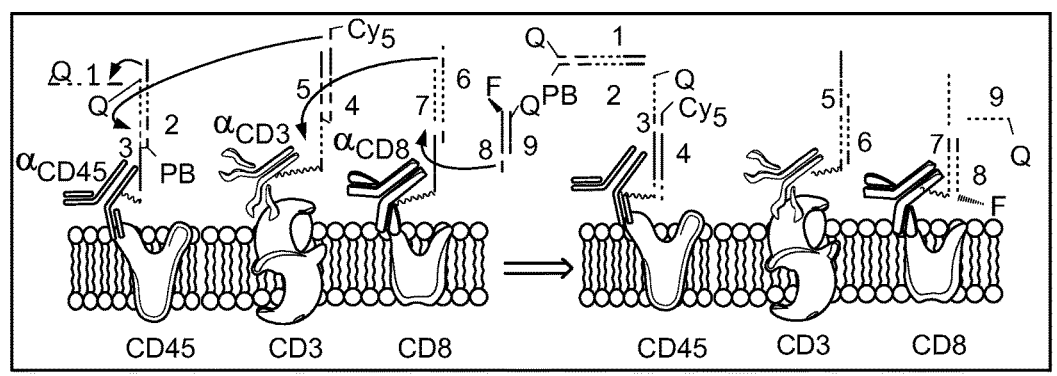
FIG. 22A-FIG. 22B shows an illustration of a cascade assessing presence of three markers on the surface of the cell; the three markers are: CD45, CD3 and CD8 (cf., main text).
Figure 22B:
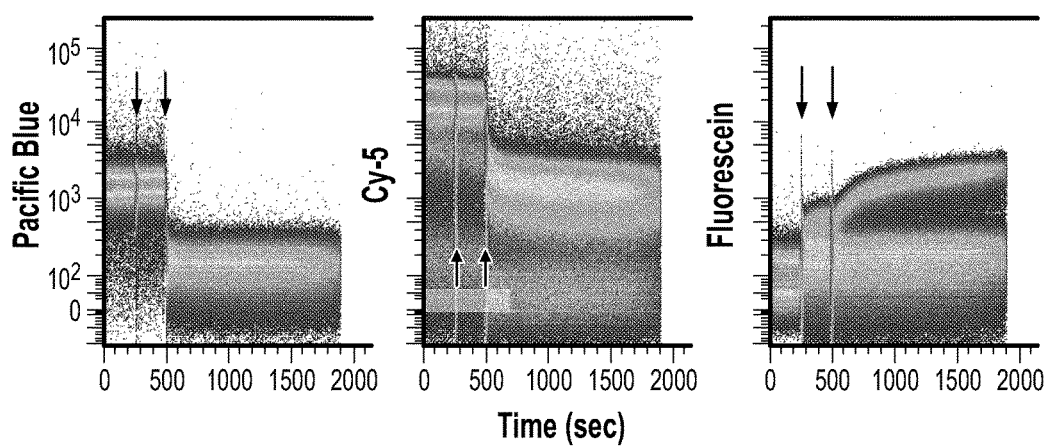

In some embodiments, a target cell can be a lymphocyte (see e.g., FIG. 19), NK cell, T-cell, or B-cell.

Vesicles.

In some embodiments, a target biological object can be a vesicle. A vesicle can be a lipid membrane (e.g., a lipid bilayer membrane, also known as a lamellar phase) enclosing a fluid interior. A vesicle can be an exosome, apoptotic bleb, shedding vesicle, microparticle, prostasome, tolerosome, or prominosome.

Different cell types can produce a large variety of vesicles into extracellular space. Such vesicles can have some surface markers the same as a parental cell or some surface markers that are not present on the surface of parent cells (e.g., intracellular). Labeling extracellular vesicles produced by specific cell types (cancer cells, activated immune cells, etc) can provide for diagnostic or therapeutic applications.

A vesicle can be an artificial vesicle or a natural vesicle.

An artificial vesicle can be a liposome. A vesicle can be a liposome with one phospholipid bilayer, also known as a unilamellar liposome vesicle. A vesicle can be a liposome with more than one phospholipid bilayer, also known as a multilamellar liposome vesicle.

A natural vesicle can be a small organelle produced within a cell. A natural vesicle can for naturally, such as during secretion (exocytosis), uptake (phagocytosis and endocytosis) or transport of materials within the cytoplasm. A vesicle can have the same or a different composition from the cytosolic environment of a source cell.

A vesicle can include a vacuole (e.g., a plant vacuole or contractile vacuole), lysosome, peroxisome, transport vesicle, secretory vesicle, synaptic vesicle, hormonal secretory vesicle, cell wall-associated vesicle, toxic membrane vesicle, signal molecule vesicle, gas vesicle, membrane vesicle, matrix vesicle, multivesicular body, or outer membrane vesicle. Exemplary target vesicles include those produced by cells such as stem cells, leukocyte groups, granulocytes, monocytes, T lymphocytes, T helper cells, T regulatory cells, Cytotoxic T cells, lymphocytes, thrombocytes, and natural killer cells.

Methods of isolating vesicles are known in the art (see generally, Harrison, et al., Ed., Extracellular Vesicles in Health and Disease, 2014, Pan Stanford Publishing; 1st edition, ISBN-10: 9814411981). Such conventional methods can be modified or adapted in view of the present disclosure so as to more precisely or efficiently identify or isolate a vesicle. Conventional methods include isolating a culture medium component, or fraction thereof, from a cell culture. Methods described herein can be used to identify or isolate target vesicles from the culture medium component, or fraction thereof. Conventional methods include crushing a tissue into a suspension so as to allow various membranes to form tiny closed bubbles. Methods described herein can be used to identify or isolate target vesicles from such a suspension. Large fragments of crushed cells can be discarded by low-speed centrifugation, and later the fraction of a known origin (e.g., plasmalemma, tonoplast, etc.) can be isolated by precise high-speed centrifugation in the density gradient. Methods described herein can be used to identify or isolate target vesicles from such a large fragment fraction, small fragment fraction, or a density gradient fraction, or some other fraction in the procedure. Osmotic shock can be used to temporarily open vesicles (filling them with the required solution) and then centrifugate down again or resuspend in a different solution. Methods described herein can be used to identify or isolate target vesicles or component objects thereof before during, or after such procedure.

Organelle or Macromolecule.

In some embodiments, a target biological object can be an organelle or macromolecule. An organelle can be a membrane-bound organelle or a non-membrane bound organelle. An organelle is understood to be a specialized subunit of a cell with a specific function, and is usually separately enclosed within its own lipid bilayer. An organelle can be a Eukaryotic organelle or macromolecule. Exemplary organelles or macromolecules include, but are not limited to, a mitochondria, plastic, flagellum, endoplasmic reticulum, Golgi apparatus, vacuole, nucleus, acrosome, autophagosome, centriole, cilium, eyespot apparatus, glycosome, glyoxosome, hydrogenosome, lysosome, melanosome, mitosome, myofibril, nematocyst, nucleolus, parenthesome, peroxisome, proteasome, ribosome, 80s ribosome, vesicle, nucleosome, or microtubule. Exemplary macromolecules include, but are not limited to large RNA and protein complexes, such as a ribosome, spliceosome, or vault; large protein complexes, such as a proteasome, DNA polymerase III holoenzyme, RNA polymerase II holoenzyme, symmetric viral capsid, complex of GroEL and GroES, membrane protein complex, photosystem I, or ATP synthase; large DNA and protein complexes, such as a nucleosome, centriole and microtubule-organizing center (MTOC), cytoskeleton, or flagellum; or a non-membrane bound cellular structure that does not have a well-defined structure, such as a nucleolus.

An organelle can be a Prokaryotic organelle or macromolecule. Exemplary organelles or macromolecules include, but are not limited to, carboxysome, chlorosome, flagellum, magnetosome, nucleoid, plasmid, ribosome, 70s ribosome, thylakoid, or mesasome.

Surface Marker

As described herein, surface markers of a target biological object can serve as input targets for antibodies linked to nucleotides specific for strand-displacement cascades. As such, a biological object surface marker can be any surface marker or combination thereof that appears (or does not appear) in a unique combination on the surface of a target biological object of interest. In some embodiments, a biological object surface marker will have an identified antibody specific for such marker.

In some embodiments, a biological object surface marker can be a cluster of differentiation (or a cluster of designation) (CD). CD is understood as a protocol for the identification and investigation of surface molecules providing targets for immunophenotyping of cells. In the art, a surface molecule is assigned a CD number once two specific monoclonal antibodies (mAb) are shown to bind to the molecule. A biological object (e.g., a cell population or subpolulation, or a vesicle population or subpopulation, such as an extracellular vesicle subpopulation) can be defined using a "+" or a "−" symbol to indicate whether a certain fraction expresses or lacks a CD molecule. A combination of markers (e.g., CD markers) can provide for cell types or biological objects produced by or associated with a certain cell type(s) with very specific definitions (e.g., within the immune system).

Exemplary CDs are as follows: stem cells, CD34+, CD31−, CD117; all leukocyte groups, CD45+; Granulocyte, CD45+, CD11b, CD15+, CD24+, CD114+, CD182+; Monocyte, CD45+, CD14+, CD114+, CD11a, CD11b, CD91+, CD16+; T lymphocyte, CD45+, CD3+; T helper cell, CD45+, CD3+, CD4+; T regulatory cell, CD4, CD25, Foxp3; Cytotoxic T cell, CD45+, CD3+, CD8+; naïve T-cell, CD45RA+, CD3+; B lymphocyte, CD45+, CD19+ or CD45+, CD20+, CD24+, CD38, CD22; Thrombocyte, CD45+, CD61+; Natural killer cell, CD16+, CD56+, CD3−, CD31, CD30, CD38.

In some embodiments, cell surface markers include CD3, CD8, or CD25. In some embodiments, cell surface markers include CD3, CD8, and CD25.

An object surface marker can be a marker associated with an organelle (see e.g., Nelson et al., 2007, The Plant Journal 51, 1126-1136). An object surface marker can be a marker associated with a biological object (e.g., an organelle or macromolecule). For example, an object surface marker can be a receptor molecule associated or embedded in or on the surface of a biological object (e.g., an organelle or macromolecule). As another example, a target object marker can be a Type 1 receptor (e.g., ionotrophic receptor), Type 2 G protein-coupled receptor (e.g., metabotropic), Type 3 kinase linked or related receptors, or Type 4 nuclear receptor. As another example, a target object marker can be an immune receptor (e.g., pattern recognition receptor (PRR), Toll-like receptor (TLR), killer activated and killer inhibitor receptor (KAR and KIR), complement receptors, Fc receptors, B cell receptor, T cell receptor, cytokine receptor), ion channel linked receptor, nicotinic acetylcholine receptor, a glycine receptor, a GABA receptor (e.g., GABA-A, GABA-C), glutamate receptor (e.g., NMDA receptor, AMPA receptor, Kainate receptor), 5-HT3 receptor, or P2X receptor. As another example, a target object marker can be a cyclic nucleotide-gated ion channel, IP3 receptor, intacellular ATP receptor, or ryanodine receptor.

An object surface marker can be a marker associated with a vesicle coat. A vesicle can have a vesicle coat, such as a clathrin coat, COPI coat, COPII coat, or coatomer coat. Clathrin coats can be found on vesicles trafficking between the Golgi and plasma membrane, the Golgi and endosomes, or the plasma membrane and endosomes. COPI coated vesicles can be responsible for retrograde transport from the Golgi to the ER. COPII coated vesicles can be responsible for anterograde transport from the ER to the Golgi. An vesicle surface marker can be a marker associated with a clathrin coat, COPI coat, COPII coat, or coatomer coat.

A biological object can have a SNARE surface marker. For example, a vesicle can have a SNARE surface marker. A SNARE surface marker can identify a vesicle's cargo. A complementary SNARE on a vesicle target membrane can act to cause fusion of the vesicle and target membrane. Such v-SNARES are thought to exist on the vesicle membrane, while complementary ones on the target membrane are known as t-SNAREs. A SNARE associated with a vesicle or target membrane can be classified as a Qa, Qb, Qc, or R SNARE, which accounts for further variation over v- or t-SNAREs. An array of different SNARE complexes can occur in different tissues or subcellular compartments. Presently, at least 36 SNARE isoforms have been identified in humans.

An object surface marker can be an organic small molecule. For example, an object surface marker can be a steroid or nitro-phenol compound.

Oligonucleotide

As described herein, a plurality of oligonucleotide molecules can be configured so as to result in a series of strand-displacement reactions. Nucleotides specific for strand-displacement cascades can be as described herein. Generally, differences in complementarity between oligonucleotides can drive the strand-displacement reactions.

An oligonucleotide can include about 10 to about 100 nucleotides. For example, an oligonucleotide can include about 10, about 15, about 20, about 25, about 30, about 35, about 40, about 45, about 50, about 55, about 60, about 65, about 70, about 75, about 80, about 85, about 90, about 95, or about 100. It is understood that ranges between each combination of the above recited values are included in the present application.

As described herein, differences in complementarity between oligonucleotide can drive a strand-displacement reaction. A difference in complementarity sufficient to drive a strand-displacement reactions can occur where two oligonucleotides have less than about 99% sequence identity. For example, s difference in complementarity sufficient to drive a strand-displacement reactions can occur where two oligonucleotides have less than about 99%, about 95%, about 90%, about 85%, about 80%, about 75%, about 70%, about 65%, about 60%, about 55%, about 50%, about 45%, about 40%, or less sequence identity. It is understood that ranges between each combination of the above recited values are included in the present application.

An extension of one oligonucleotide when paired with another oligonucleotide can create a "toe hold" sufficient to drive a strand-displacement reaction. A toe hold can include at least about 1 nucleotide. For example, a toe hold can include at least about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, or more nucleotides. It is understood that ranges between each combination of the above recited values are included in the present application.

Presence of a toe hold can contribute to differences in complementarity between two oligonucleotides. Differences in complementarity can include mismatches along with length of two oligonucleotides, presence of one or more toe hold, or a combination thereof.

For example, in a system with two target markers (e.g., YesYes), a first double strand complex can include a first oligonucleotide and a second oligonucleotide, the second oligonucleotide linked to the first target-specific agent (e.g., an antibody). The first target-specific agent can bind to a target biological object surface marker for which it is specific. Introduction of a single stranded fifth oligonucleotide, where the first oligonucleotide has more complementarity for the fifth oligonucleotide than for the second oligonucleotide, can result in a strand displacement reaction in which the first oligonucleotide and the fifth oligonucleotide become paired leaving a single stranded second oligonucleotide.

In the above system, a second double strand complex including a third oligonucleotide and a fourth oligonucleotide, the fourth oligonucleotide linked to a second target-specific agent (e.g., an antibody), can be introduced. The second target-specific agent binds to a target biological object surface marker for which it is specific. Introduction of a single stranded sixth oligonucleotide, where the third oligonucleotide has more complementarity for the second oligonucleotide than for the fourth oligonucleotide, can result in a strand displacement reaction in which the third oligonucleotide and the second oligonucleotide become paired leaving a single stranded fourth oligonucleotide linked to the second target-specific agent linked to the target biological object surface marker for which it is specific.

In the above system, a single stranded sixth oligonucleotide linked to a therapeutic agent can be introduced. The sixth oligonucleotide can have sufficient complementarity to the single stranded fourth oligonucleotide to bind thereto, but insufficient complementarity for the fourth oligonucleotide to disrupt the pairing of the third oligonucleotide and fourth oligonucleotide. In such case, the therapeutic agent is selectively bound to a target biological object having two particular cell surface markers.

In some embodiments, an oligonucleotide itself is a therapeutic agent. For example, in the above described system, the fourth oligonucleotide can be an aptamer against toxin or cytotoxic cells (e.g., NK cells or T cells). Where the third oligonucleotide is transferred to the second oligonucleotide, the fourth oligonucleotide (now single stranded) can become active and acquire a toxin effect or attract a cytotoxic cell. Where an oligonucleotide itself is a therapeutic agent, some other oligonucleotides may not be needed. For example, where the fourth oligonucleotide is an aptamer, the sixth oligonucleotide or the seventh oligonucleotide may not be present.

The above explanation of a YesYes system, can be adapted to other logical systems according to the disclosure herein.

Target Specific Agent

As described herein, a target specific agent can be conjugated to a oligonucleotide specific for strand-displacement cascades. Such a conjugate can form a target marker allowing binding to surface markers of a target biological object. A target specific agent for use with systems described herein can be capable of being coupled to a nucleotide. A target specific agent can be an oligonucleotide, antibody, or protein.

A target specific agent used herein can specifically bind to a particular target biological object surface marker. As such, choice of a target biological object surface marker can be determined according to availability of target specific agent (e.g., an antibody) specific thereto.

In some embodiments, a target-specific agent comprises an immunopeptide, including but not limited to, polyclonal antibodies, monoclonal antibodies (MAbs), antibody fragments (e.g., Fab, F(ab')$_2$, F(ab')$_2$, F(ab')$_3$, Fc, single chain Fv (scFv), scFV-Fc, (scFv)$_2$, dsFv, Vh, Vl, Minibody, Diabody, Triabody, Tetrabody), and antibody fusion molecules. For example, a target-specific agent can be an antibody specific for an object surface marker. As another example, a target-specific agent can be a monoclonal antibody specific for an object surface marker.

Engineering, production, purification, fragmentation, and use of various types of antibodies are well known in the art (see generally, Carter, (2006), Nat Rev Immunol., 6(5), 343-357; Teillaud, (2005), Expert Opin Biol Ther., 5(Supp. 1) S15-27; Subramanian, ed. (2004), Antibodies: Volume 1: Production and Purification, Springer, ISBN 0306482452; Lo, ed. (2003), Antibody Engineering Methods and Protocols, Humana Press, ISBN 1588290921; Ausubel et al., ed., (2002), Short Protocols in Molecular Biology 5th Ed., Current Protocols, ISBN 0471250929; Brent et al., ed. (2003), Current Protocols in Molecular Biology, John Wiley & Sons Inc, ISBN 047150338X; Lo, ed. (2003) Antibody Engineering Methods and Protocols, Humana Press, ISBN 1588290921; Coligan, (2005), Short Protocols in Immunology, John Wiley & Sons, ISBN 0471715786).

Polyclonal antibodies are heterogeneous populations of antibody molecules that are obtained from immunized animals, usually from sera. Polyclonal antibodies may be readily generated by one of ordinary skill in the art from a variety of warm-blooded animals, as well known in the art and described in the numerous references listed above. It is generally understood that larger mammals, such as a horse described herein, are preferred as the amount of serum that can be collected is greater. Generally, an antigen (as discussed above) is injected into the mammal (e.g., a horse). This can induce the β-lymphocytes to produce IgG immunoglobulins specific for the antigen. This polyclonal IgG can be purified from the mammal's serum.

Monoclonal antibodies are homogeneous populations of antibodies to a particular antigen (e.g. an object surface marker). In contrast to polyclonal antibodies that may be specific for several epitopes of an antigen, monoclonal antibodies are usually specific for a single epitope. Generally, monoclonal antibodies are produced by removing β-cells from the spleen of an antigen-challenged animal (wherein the antigen includes the proteins described herein) and then fusing with myeloma tumor cells that can grow indefinitely in culture. The fused hybrid cells, or hybridomas, multiply rapidly and indefinitely and can produce large amounts of antibodies. The hybridomas can be sufficiently diluted and grown so as to obtain a number of different colonies, each producing only one type of antibody. The antibodies from the different colonies can then be tested for their ability to bind to the antigen, followed by selection of the most effective. In particular, monoclonal antibodies can be obtained by any technique that provides for the production of antibody molecules by continuous cell lines in culture such as those described in references listed above.

Such antibodies can be of any immunoglobulin class including IgG, IgM, IgE, IgA, IgD and any subclass thereof. Preferably, the antibody is of the IgE immunoglobulin class. In some embodiments, the antibody is of the IgG immunoglobulin class, which can be utilized either in isolation or in combination with IgE. A hybridoma producing a mAb of the present disclosure may be cultivated in vitro or in vivo. The ability to produce high titers of mAbs in vivo makes this a particularly useful method of production. MAbs generally have a longer terminal half life than many antibody fragments, which can be desirable for therapeutic applications.

MAbs can be selected on the basis of their (a) specificity, (b) high binding affinity, (c) isotype, and (d) stability. MAbs can be screened or tested for specificity using any of a variety of standard techniques, including Western Blotting (Koren, E. et al., Biochim. Biophys. Acta, 876:91-100 (1986)) and enzyme-linked immunosorbent assay (ELISA) (Koren et al., Biochim. Biophys. Acta, 876:91-100 (1986)).

Chimeric, humanized, and fully human MAbs can effectively overcome potential limitations on the use of antibodies derived from non-human sources to treat cancer, thus providing decreased immunogenicity with optimized effector functions (see e.g., Teillaud, (2005), Expert Opin. Biol. Ther., 5(1), S15-S27; Tomizuka et al., (2000), Proc. Nat. Acad. Sci. USA, 97, 722-727; Carter et al., (2006), Nat Rev Immunol., 6(5), 343-357, 346-347).

It may be desirable to produce and use functional antibody fragments (e.g., Fab, F(ab')$_2$, F(ab')$_2$, F(ab')$_3$, Fc, single chain Fv (scFv), scFV-Fc, (scFv)$_2$, dsFv, Vh, Vl, Minibody, Diabody, Triabody, Tetrabody). Generally, these alternative antibody formats can span a molecular-weight range of 12-150 kDa; a valency (n) range from monomeric (n=1), dimeric (n=2), trimeric (n=3), tetrameric, or even higher; and antigen-binding specificities from one to more than three antigens or epitopes on the same antigen.

Preferably, an antibody is a monoclonal antibody or antibody fragment specific for an object surface marker, and will usually bind with at least a $K_D$ of about 1 mM, more usually at least about 300 μM, typically at least about 30 μM, preferably at least about 10 μM, and more preferably at least about 3 μM or better.

Therapeutic Agent

As described herein, a therapeutic agent can be coupled to a oligonucleotide specific for strand-displacement cascades. Accordingly, at the termination of strand-displacement cascades, the therapeutic agent can be bound to the target biological object by way of a target marker.

A therapeutic agent can be any agent known to have an effect on a target biological object. A therapeutic agent for use with systems described herein can be coupled to a nucleotide. A therapeutic agent can be a cell toxin. Exemplary cells toxins include, but are not limited to, ribosome inactivating proteins (RIPs), such as saporin and gelonin. A therapeutic agent can be calicheamicin or maytansinoid (e.g., gemtuzumab zogamicin or Mylotarg). A therapeutic agent can be a cardiotonic steroid (e.g., bufalin or carbamate).

A therapeutic agent can be an aptamer (see e.g., Boltz et al. 2011 J Biol Chem 286(24), 21896-21905).

Other therapeutic agents for therapeutic modules described herein include (i) bi-specific antibodies used to destroy target cells by crosslinking them to T-cells (which are then, in the process, activated; e.g., CD19 on B-cells and CD3 on T-cells); or connect 5, once displayed on targeted cells, to an antibody conjugate displayed on T-cells; (ii) crosslinking with CD95 ("death receptor"); (iii) delivery of siRNA using aptamers; (iv) GDEPT vector delivery; (v) liposome targeting; and (vi) hypercrosslinking.

In some embodiments, a therapeutic agent can be added to or substituted with an imaging agent (e.g., quantum dot; radiolabel, such as PET SPECT, etc.; fluorescent label; or MRI agent).

Molecular Coupling

As described herein, a target-specific agent (e.g., an antibody) can be coupled to nucleotides specific for strand-displacement cascades. Also as described herein, a therapeutic agent can be coupled to nucleotides specific for strand-displacement cascades.

Coupling, tagging, or linking molecules to oligonucleotides, antibodies, or proteins are well known in the art. Except as otherwise noted herein, therefore, the subject matter of the present disclosure can be carried out in accordance with such known processes.

Conjugation of an oligonucleotide and a target-specific agent (e.g., an antibody) can be according to any method understood in the art. For example, coupling can be based on a disulfide bond reduction and coupling to maleimide-derivatized oligonucleotides (see e.g., Liu et al. 2010 Anal. Chem. 82, 5219-5226; Hermanson, "Bioconjugate Techniques", 2nd Edition, Elsevier Inc, Academic Press, New York (2008)). In some embodiments, coupling techniques can provide on average from 1:1 to 1:4 (target-specific agent:oligonucleotide) conjugates, as determined by both ion exchange HPLC and UV/Vis comparison to standard mixtures.

As another example, coupling can be according to cross-linking protocols based on NHS-ester coupling to target-specific agent, for which commercial kits are available. As another example, coupling can be according to a biotinylated target-specific agent and streptavidin. In some embodiments, biotinylated target-specific agents and streptavidin coupling is used only for one step in a cascade, due to potential exchange of biotinylated oligonucleotides between target-specific agents.

A target-specific agent can be coupled, tagged, or linked to an oligonucleotide. Strepavidin can be used to cross-link a target-specific agent to a biotinylated oligonucleotide (see e.g., Example 1).

A beacon, tracer, or stain (e.g., fluorophore) can be coupled, tagged, or linked to a target-specific agent, such as an oligonucleotide, antibody, or protein.

A toxin or drug can be coupled, tagged, or linked to a target-specific agent, such as an oligonucleotide, antibody, or protein.

A crosslink to other cells, toxins, or drugs (e.g., aptamer, antibody) can be coupled, tagged, or linked to a target-specific agent, such as an oligonucleotide, antibody, or protein. An aptamer can be coupled, tagged, or linked to a target-specific agent, such as an oligonucleotide, antibody, or protein. An antibody can be coupled, tagged, or linked to a target-specific agent, such as an oligonucleotide, antibody, or protein.

A nanoparticle or vesicle (e.g., liposome, micelle) can be coupled, tagged, or linked to a target-specific agent, such as an oligonucleotide, antibody, or protein. A nanoparticle or vesicle (e.g., liposome, micelle) carrying a toxin or drug can be coupled, tagged, or linked to a target-specific agent, such as an oligonucleotide, antibody, or protein.

Target Biological Object Separation

As described herein, biological objects can be separated based on sequential recognition of a selected set of surface markers by molecular automata. After a molecular device described herein autonomously evaluates Boolean functions on a biological object surface with a plurality of surface markers as inputs and a tag as an output, targeted biological object can be separated according to their unique handle.

Biological object separation based on surface antigens are known in the art. Multistep (e.g., two step) cell separation based on surface antigens are known in the art. Except as otherwise noted herein, therefore, the process of the present disclosure can be carried out in accordance with such processes.

For example, a target cell having a unique handle resulting from use of sequentially recognized target markers described herein can be separated by flow cytometry (e.g., Fluorescence-activated cell sorting (FACS)). Flow cytometry is understood as a laser-based, biophysical technology employed in cell sorting or marker detection by suspending cells in a stream of fluid and passing them by an electronic detection apparatus. Flow cytometry can allow simultaneous multiparametric analysis of the physical and chemical characteristics of up to thousands of particles per second. Use of flow cytometry to physically sort particles based on their properties (e.g., a unique handle resulting from sequentially recognized target markers described herein) so as to isolate or purify target cells is understood in the art. Data generated by a flow-cytometer can be plotted in a single dimension, to produce a histogram, or in two-dimensional dot plots or even in three dimensions. The regions on these plots can be sequentially separated, based on fluorescence intensity, by creating a series of subset extractions, termed "gates". Plots can be made on logarithmic scales. Because different fluorescent dyes' emission spectra can overlap, signals at the detectors can be compensated electronically as well as computationally, as understood in the art. Data accumulated using the flow cytometer can be analyzed using software, e.g., WinMDI, Flowing Software, or web-based Cytobank, FCS Express, Flowjo, FACSDiva, CytoPaint (aka Paint-A-Gate), VenturiOne, CellQuest Pro, Infinicyt or Cytospec. Representative automated population identification methods include FLOCK in Immunology Database and Analysis Portal (ImmPort), FLAME in GenePattern and flowClust, in Bioconductor.

FACS can provide a method for sorting a heterogeneous mixture of biological cells into two or more containers, one cell at a time, based upon the specific light scattering and fluorescent characteristics of each cell. FACS can provide fast, objective and quantitative recording of fluorescent signals from individual cells as well as physical separation of target cells having a unique handle. In FACS, a cell suspension can be entrained in the center of a narrow, rapidly flowing stream of liquid. The flow can be arranged so that there is a large separation between cells relative to their diameter. A vibrating mechanism can cause the stream of cells to break into individual droplets. The system can be adjusted so that there is a low probability of more than one cell per droplet. Just before the stream breaks into droplets, the flow can pass through a fluorescence measuring station where the fluorescent character of interest of each cell is measured. An electrical charging ring can be placed just at the point where the stream breaks into droplets. A charge can be placed on the ring based on the immediately prior fluorescence intensity measurement, and the opposite charge can be trapped on the droplet as it breaks from the stream. The charged droplets can then fall through an electrostatic deflection system that diverts droplets into containers based upon their charge. In some systems, the charge can be applied directly to the stream, and the droplet breaking off retains charge of the same sign as the stream. The stream can then be returned to neutral after the droplet breaks off.

For example, a target biological object having a unique handle resulting from use of sequentially recognized target markers described herein can be separated using a Cytometric Bead Array (CBA). Compositions and methods of the present disclosure can be adapted for detection in accordance with CBA.

As another example, a target biological object having a unique handle resulting from use of sequentially recognized target markers described herein can be separated using magnetic-activated cell sorting (MACS). MACS is understood to be a method for separation of various cell populations depending on their surface antigens (CD molecules) but can be adapted for separation of a biological object. MACS separation can include incubating target biological objects having unique handles with magnetic nanoparticles coated with antibodies against a particular unique handle. This can cause a target biological object to attach to the magnetic nanoparticles. A solution or suspension containing or thought to contain a target biological object can be transferred on a column placed in a strong magnetic field. In some embodiments, the target biological objects attached to the nanoparticles (having the unique handle) stay on the column, while other biological objects (not having the unique handle) flow through. According to such methods, the taregy biological objects can be separated positively or negatively with respect to a unique handle.

A magnetic nanoparticle can be coated with an anti-fluorochrome antibody. A unique handle of a target biological object can be fluorescent-labelled. The magnetic nanoparticle coated with an anti-fluorochrome antibody can be incubated with the fluorescent-labelled target biological objects (resulting from sequentially recognized target markers described herein) and provide for biological object separation with respect to the unique handle.

As another example, a target biological object having a unique handle resulting from use of sequentially recognized target markers described herein can be separated using Dynabeads. Dynabeads are superparamagnetic spherical polymer particles with a uniform size and a consistent, defined surface for the adsorption or coupling of various bioreactive molecules or cells. Such conventional materials can be adapted for a target biological object having a unique handle resulting from use of sequentially recognized target markers described herein.

As another example, a target biological object (e.g., a vesicle) having a unique handle resulting from use of sequentially recognized target markers described herein can be separated using beads coated with an anti-fluorochrome antibody or (strept)avidin or any other anti-small molecule antibody (with small molecule being a unique handle on the object). Examples of small molecules that can be used as handles include steroids or nitro-phenol compounds. Beads can be spherical polymer particles that can have a uniform size or a consistent or defined surface for the adsorption or coupling of various bioreactive molecules or vesicles. Such conventional materials can be adapted for a target biological object having a unique handle resulting from use of sequentially recognized target markers described herein. Such beads can be collected by low speed centrifugation with following washing from unbound objects by repeated centrifugation. As another example, a target biological object (e.g., vesicle) having a unique handle resulting from use of sequentially recognized target markers described herein can be separated using plasmapheresis.

Molecular Engineering

The following definitions and methods are provided to better define the present invention and to guide those of ordinary skill in the art in the practice of the present invention. Unless otherwise noted, terms are to be understood according to conventional usage by those of ordinary skill in the relevant art.

Design, generation, and testing of the variant nucleotides, having the above required activitiesis within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557.

Nucleotide complementarity percent (%) is understood as the percentage of nucleotide residues that are identical with nucleotide residues in a comparison sequence when the two sequences are aligned. To determine percent complementarity, sequences are aligned and if necessary, gaps are introduced to achieve the maximum percent sequence identity. Sequence alignment procedures to determine percent complementarity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence complementarity of a given sequence A to, with, or against a given sequence B (which can alternatively be phrased as a given sequence A that has or comprises a certain percent complementarity identity to, with, or against a given sequence B) can be calculated as: percent sequence complementarity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

Generally, conservative substitutions can be made at any position so long as the required activity is retained.

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The formulation should suit the mode of administration. The agents of use with the current disclosure can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided is a process of treating a disease or disorder in a subject in need administration of a therapeutically effective amount of a therapeutic module described herein, so as to deliver a therapeutic agent to a target biological object having a particular combination of markers on the target biological object surface or to prevent delivery of a therapeutic agent to a target biological object having a particular combination of markers on the target biological object surface. Cascades on a target biological object surface, as described herein, can result in a unique oligonucleotide displayed on the targeted biological object. In some embodiments, a therapeutic module can interact with such unique oligonucleotide to cause a therapeutic effect. In some embodiments of a therapeutic module in which an output of a biomolecular computing cascade will be coupled to a therapeutic effect, e.g., target biological object elimination.

In various embodiments, systems of biomolecules, e.g., mixtures of interacting proteins and nucleic acids, can become active or inactive based on analyses of their environments. In such systems, switching between an active state and an inactive state (e.g., between possible outcomes) can occur if certain sets of sensory inputs are present or absent in the environment. The dependence of these changes of states on inputs can be described through input-output correlation tables (e.g., "truth tables"). Thus can be achieved implementation of systems of cascaded reactions coupled to target specific agents (e.g., antibodies) interacting with target biological object surface markers.

According to approaches described herein, a therapeutic module can be constructed in which an output of a biomolecular computing cascade can be coupled to a therapeutic effect, e.g., target biological object elimination. This can be achieved by, for example, triggering delivery of proteins or small molecule toxins, or by activating an enzyme involved in a conversion of a prodrug into a drug. Thus can be achieved inhibition of toxic effects on non-target biological objects bearing a protective signatures on the biological object surface, and analysis of a plurality of biological object surface markers (e.g., three surface markers).

Also according to approaches described herein, an imaging module can be constructed in which an output of a biomolecular computing cascade can be coupled to generation or amplification of various signals useful for imaging of events on the surface of targeted biological objects. For example, a cell-specific signal can be amplified through accumulation of Gd(III) complexes (e.g., MRI contrast) or "light-up" fluorophores, radiolabels, or the like. For example, an imaging module can be used to determine mass of insulin producing β-cells in the pancreas in vivo. The mass of β-cells, the insulin producing component of endocrine pancreas, represents less than 0.005% of the normal adult bodyweight.

Imaging of β-cell molecular targets can reveal quantitative information about β-cell mass and or function, which can be used, e.g., to monitor diabetes progression, assess therapeutic approaches related to proliferation and differentiation of endogenous β-cell progenitors, or appraise methods of preserving mature β-cell mass or track the function or viability of transplanted cells.

According to approaches described herein, a plurality of target biological object surface markers (e.g., three) can be selected such that only pancreatic endocrine cells, or biological objects associated with or produced by pancreatic endocrine cells, would have all of them (e.g., LAT-1, Glut 2, D2R, Kir6.1, or GLP1 RI) (i.e., other objects in other tissues would not have all markers) individual markers. A system described herein can be modularly built, i.e., a combination of parts having individual functions. In some embodiments, available functions can include one or more of (i) recognition (e.g., interactions with environment that can be transduced downstream); (ii) computing (e.g., a process through which inputs are correlated to outputs); and (iii) actions (e.g., possible output functions, including light-up property, capture tags, or therapeutic moieties). Modularity can allow change of behaviors in systems by mixing and matching varieties of functional modules, or adjusting them to targeted applications. Thus can be achieved combining different recognition and computing modules with "tagging" modules (e.g., fluorescein or biotin). In this way, autonomous biocomputing cascades can, for example, mark for isolation a target biological object, such as a subpopulation of lymphocytes, within complex mixtures of peripheral blood mononuclear cells (PBMCs) in vitro. As another example, autonomous biocomputing cascades can mark for isolation a target biological object, such as a subpopulation of extracellular vesicles within complex mixtures of blood, serum, or plasma in vitro.

Therapeutic approaches based on target biological object-surface analysis as described herein can be useful in a disease or disorder that can benefit from selective elimination of a biological object type based on the presence or absence of multiple surface makers. Non-limiting examples include, cancer, hematopoietic malignancies, and autoimmune diseases.

For example, with respect to lymphocytes during hematopoiesis (i.e., blood cell generation), branches of the hematopoietic tree are characterized by the expression of markers on the cell surface. These markers (or antigens) include cluster of differentiation markers or "CD"(s) with associated numbers. Hematopoietic neoplasms express markers characteristic for their lineage and stages of differentiation and such markers can be used in immunophenotyping or characterization of a target biological object (e.g., a vesicle).

While targeted delivery of a toxin to a tumor cell by appropriate monoclonal antibodies (MAbs) can result in significant beneficial effects in patients in both hematopoietic malignancies and SLE, the dosage and potential efficacy of such a MAb-toxin immunoconjugates has been limited by the concurrent development of toxic effects in normal cells. A major factor in the action of these conventional immunoconjugates on normal cells is the fact that the surface markers recognized by every immunoconjugate are present on significant numbers of normal cells. Thus, despite significant progress in immunotherapy, immunosuppression, or myelosuppression, is a particular problem in the immunoconjugate treatment of hematopoietic neoplasms because virtually every lymphocyte tumor surface marker is shared by some populations of normal lymphocytes. But new findings show that tumor-derived extracellular vesicles control metastatic progression (Peinado et al. 2012 Nature Med. 18, 883-891). Accordingly, extracellular vesicles produced by malignant cells can be removed from blood stream (e.g., with plasmapheresis) according to methods and compositions described herein.

Approaches described herein can selectively eliminate one population, preserve another population, or activate therapeutic modules in the presence or absence of a combination of multiple markers. A system implementing a basic Boolean logic AND (YESYES) and NOT (YESNOT) operation can significantly improve the outcome of therapy, either by enhancing delivery to biological objects, or by protecting non-target biological objects.

Methods described herein are generally performed on a subject in need thereof. A subject in need of the therapeutic methods described herein can be a subject having, diagnosed with, suspected of having, or at risk for developing a disease or disorder that can benefit from selective marking, isolation, selection, imaging, analysis, or elimination of a biological object (e.g., a cell type or extracellular vesicle) based on the presence or absence of multiple biological object-surface makers. A determination of the need for treatment will typically be assessed by a history and physical exam consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and chickens, and humans. For example, the subject can be a human subject.

Non-limiting examples of recognized or emerging clinical needs addressable with a system described herein: chronic lymphocytic leukemia (CLL); cutaneous T-cell lymphoma (CTCL), examples of hematopoietic malignancies, and targeting B-cells in autoimmune diseases. Specifically: in CLL, selective elimination of pathogenic lymphocytes can be based on YESCD19YESCD5 (a combination extremely rare on healthy lymphocytes). In CTCL, side-effects are a recognized problem that can be minimized by protecting healthy $CD8^+$ cells by specifically targeting YESCD25NOTCD8 subpopulations. In autoimmune diseases, therapy based on the elimination of broad populations of lymphocytes (B- or T-cells) may have beneficial effects, but only with a concomitant harmful effect on the immune system. A system described herein can eliminate or substantially reduce target biological objects associated with or produced by individual subpopulations of lymphocytes (e.g., including the cells themselves), narrowing down eliminated subpopulations.

Generally, a safe and effective amount of a system described herein is, for example, that amount that would cause the desired therapeutic effect in a subject while minimizing undesired side effects. In various embodiments, an effective amount of a therapeutic agent described herein can substantially inhibit, slow the progress of, or limit the development of a disease or disorder that can benefit from selective elimination of a target biological object type based on the presence or absence of multiple surface makers.

According to the methods described herein, administration can be parenteral, pulmonary, oral, topical, intradermal, intramuscular, intraperitoneal, intravenous, subcutaneous, intranasal, epidural, ophthalmic, buccal, or rectal administration.

When used in the treatments described herein, a therapeutically effective amount of an agent described herein can be employed in pure form or, where such forms exist, in pharmaceutically acceptable salt form and with or without a pharmaceutically acceptable excipient. For example, systems of the present disclosure can be administered, at a reasonable benefit/risk ratio applicable to any medical treatment, in a sufficient amount to substantially inhibit, slow the progress of, or limit the development of a disease or disorder that can benefit from selective elimination of a target biological object based on the presence or absence of multiple surface makers.

The amount of an agent or system described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, $4^{th}$ ed., Lippincott Williams & Wilkins, ISBN 0781741475; Shamel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of agent or system can occur as a single event or over a time course of treatment. For example, agent or system can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for a disease or disorder that can benefit from selective elimination of a target biological object based on the presence or absence of multiple surface makers.

An agent or system can be administered simultaneously or sequentially with another agent, such as an antibiotic, an antiinflammatory, or another agent. For example, an agent or system can be administered simultaneously with another agent, such as an antibiotic or an antiinflammatory. Simultaneous administration can occur through administration of separate compositions, each containing one or more of an agent or system, an antibiotic, an antiinflammatory, or another agent. Simultaneous administration can occur through administration of one composition containing two or more of an agent or system, an antibiotic, an antiinflammatory, or another agent. An agent or system can be administered sequentially with an antibiotic, an antiinflammatory, or another agent. For example, an agent or system can be administered before or after administration of an antibiotic, an antiinflammatory, or another agent.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intramuscular, intraperitoneal, intravenous, subcutaneous, intranasal, epidural, ophthalmic, buccal, or rectal administration.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 µm), nanospheres (e.g., less than 1 µm), microspheres (e.g., 1-100 µm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. 2006 Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Screening

Also provided are methods for screening. In some embodiments, a candidate small molecule can be a target specific agent can be conjugated to a oligonucleotide specific for strand-displacement cascades (see above). An effect of a candidate small molecule on a target biological object can thereby be assessed.

The subject methods find use in the screening of a variety of different candidate molecules (e.g., potentially therapeutic candidate molecules). Candidate substances for screening according to the methods described herein include, but are not limited to, fractions of tissues or cells, nucleic acids, polypeptides, siRNAs, antisense molecules, aptamers, ribozymes, triple helix compounds, antibodies, and small (e.g., less than about 2000 mw, or less than about 1000 mw, or less than about 800 mw) organic molecules or inorganic molecules including but not limited to salts or metals.

Candidate molecules encompass numerous chemical classes, for example, organic molecules, such as small organic compounds having a molecular weight of more than 50 and less than about 2,500 Daltons. Candidate molecules can comprise functional groups necessary for structural interaction with proteins, particularly hydrogen bonding, and typically include at least an amine, carbonyl, hydroxyl or carboxyl group, and usually at least two of the functional chemical groups. The candidate molecules can comprise cyclical carbon or heterocyclic structures and/or aromatic or polyaromatic structures substituted with one or more of the above functional groups.

A candidate molecule can be a compound in a library database of compounds. One of skill in the art will be generally familiar with, for example, numerous databases for commercially available compounds for screening (see e.g., ZINC database, UCSF, with 2.7 million compounds over 12 distinct subsets of molecules; Irwin and Shoichet (2005) J Chem Inf Model 45, 177-182). One of skill in the art will also be familiar with a variety of search engines to identify commercial sources or desirable compounds and classes of compounds for further testing (see e.g., ZINC database; eMolecules.com; and electronic libraries of commercial compounds provided by vendors, for example: ChemBridge, Princeton BioMolecular, Ambinter SARL, Enamine, ASDI, Life Chemicals etc).

Candidate molecules for screening according to the methods described herein include both lead-like compounds and drug-like compounds. A lead-like compound is generally understood to have a relatively smaller scaffold-like structure (e.g., molecular weight of about 150 to about 350 kD) with relatively fewer features (e.g., less than about 3 hydrogen donors and/or less than about 6 hydrogen acceptors; hydrophobicity character x log P of about −2 to about 4) (see e.g., Angewante (1999) Chemie Int. ed. Engl. 24, 3943-3948). In contrast, a drug-like compound is generally understood to have a relatively larger scaffold (e.g., molecular weight of about 150 to about 500 kD) with relatively more numerous features (e.g., less than about 10 hydrogen acceptors and/or less than about 8 rotatable bonds; hydrophobicity character x log P of less than about 5) (see e.g., Lipinski (2000) J. Pharm. Tox. Methods 44, 235-249). Initial screening can be performed with lead-like compounds.

When designing a lead from spatial orientation data, it can be useful to understand that certain molecular structures are characterized as being "drug-like". Such characterization can be based on a set of empirically recognized qualities derived by comparing similarities across the breadth of known drugs within the pharmacopoeia. While it is not required for drugs to meet all, or even any, of these characterizations, it is far more likely for a drug candidate to meet with clinical successful if it is drug-like.

Several of these "drug-like" characteristics have been summarized into the four rules of Lipinski (generally known as the "rules of fives" because of the prevalence of the number 5 among them). While these rules generally relate to oral absorption and are used to predict bioavailability of compound during lead optimization, they can serve as effective guidelines for constructing a lead molecule during rational drug design efforts such as may be accomplished by using the methods of the present disclosure.

The four "rules of five" state that a candidate drug-like compound should have at least three of the following characteristics: (i) a weight less than 500 Daltons; (ii) a log of P less than 5; (iii) no more than 5 hydrogen bond donors (expressed as the sum of OH and NH groups); and (iv) no more than 10 hydrogen bond acceptors (the sum of N and O atoms). Also, drug-like molecules typically have a span (breadth) of between about 8 Å to about 15 Å.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to all or parts of a molecular automata system described herein. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988, Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1

General Procedures, Methods, and Materials

The following example outlines the general procedures, methods, and materials used in the subsequent examples.

Figure 1B:
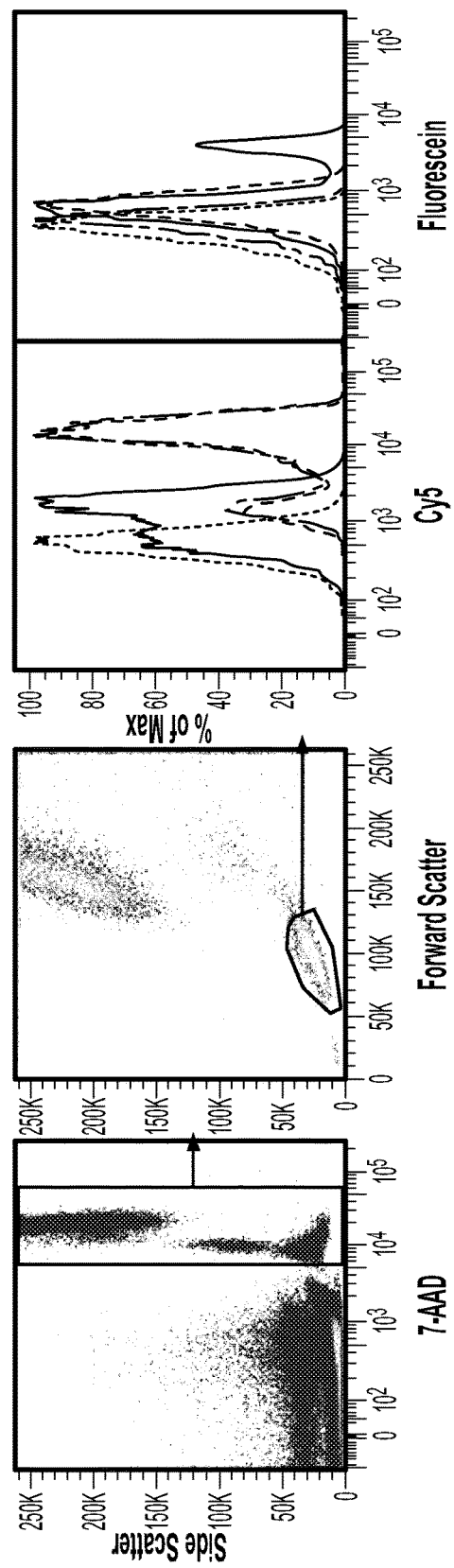

Briefly, oligonucleotides were coupled to antibodies, unless stated otherwise, in a two-step procedure: (i) DTT was used under conditions that reduce interchain disulfide bonds; (ii) oligonucleotides with maleimides at 5' ends were coupled to resulting sulfhydryls, and the products were purified using gel filtration. One biotinylated antibody was used in the NOTCD45RA cascade, in which cases streptavidin was used to cross-link it to biotinylated oligonucleotides, and this procedure was performed directly on cells without purification of conjugates (negative controls with no streptavidin and no antibody were successfully run as well, in this case). Reagents were added to cell suspensions, and in all experiments involving PBMC's, reagents were removed from solution by centrifugation. In whole blood experiments (see e.g., FIG. 1), reagents were left in blood, to mimic in vivo applications.

Example 2

Antibody Selection

The following example describes the materials used as the antibodies for the following examples.

Anti-human CD3 (clone HIT3a); anti-human CD8 (clone SK1); anti-human CD45 (clone HI30); anti-human CD45RA (clone HI100), were commercially supplied by Biolegend. Anti-human CD20 Rituxan (Rituximab) was commercially supplied by Genentech.

Example 3

Oligonucleotide Materials and Design Methods

The following example describes the materials and methods used in the sequence design of the oligonucleotides described in the following examples.

All oligonucleotides were commercially manufactured by Integrated DNA Technologies Inc. (Coralville, Iowa), with HPLC purification, and used as received, except for Pacific Blue dye modified oligonucleotides were commercially manufactured by Invitrogen™ (Life Technologies Corporation). The following 3' and 5' modifications were used: thiol modifier C6 S-S; Biotin-TEG; Iowa Black® FQ; Iowa Black® RQ; Fluorescein dye 6-FAM™ (NHS ester); or Cy5™.

Figure 2:
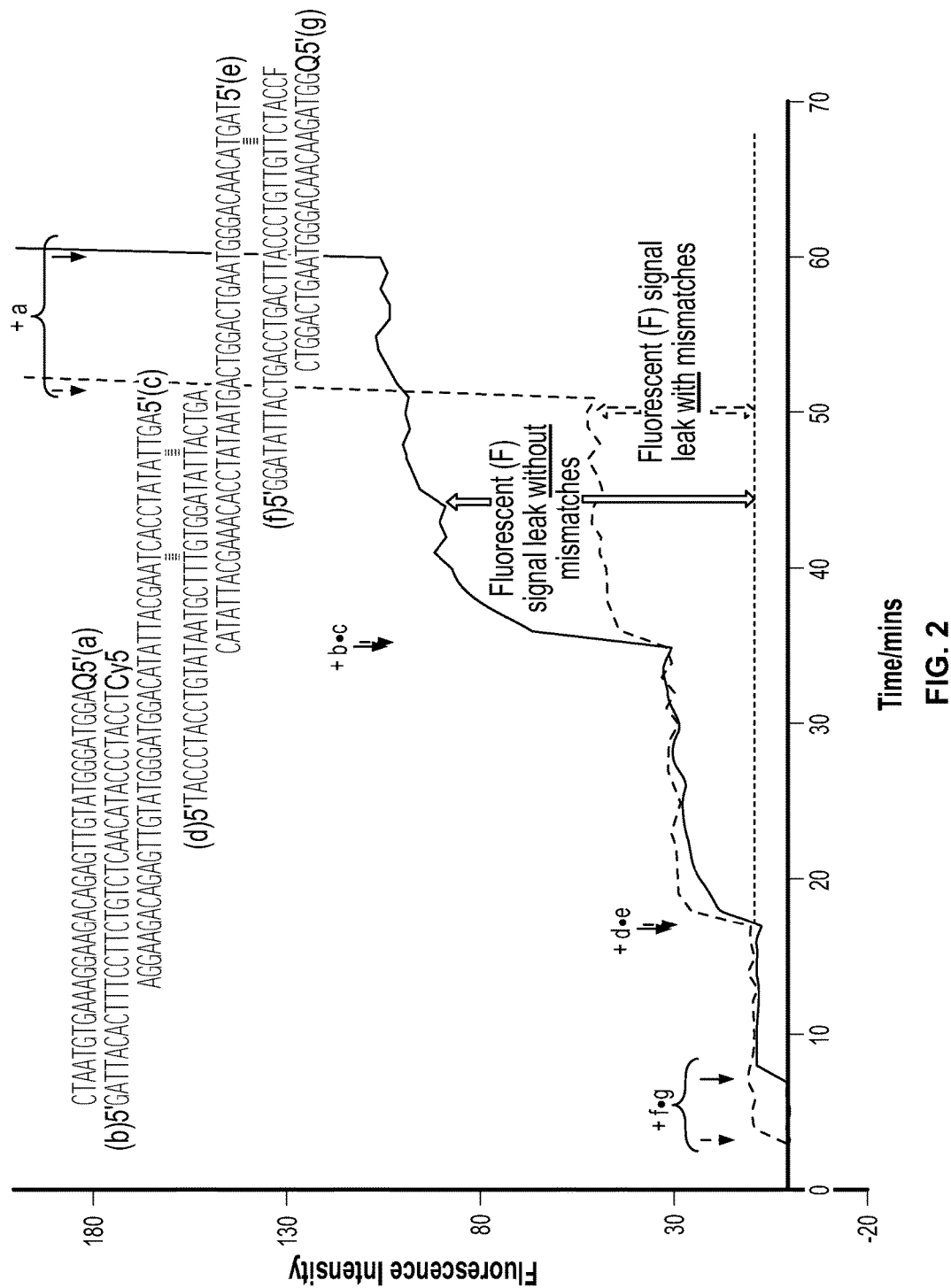
FIG. 2 is a series of oligonucleotide sequences and fluorescence spectra showing the effect of mismatches (depicted by hashed lines) on unwanted fluorescent signal (fluorescein F) leak in a YES-YES cascade. Duplexes b•c (b, SEQ ID NO: 2; c, SEQ ID NO: 3), d•e (d, SEQ ID NO: 4; e, SEQ ID NO: 5), and f•g (f, SEQ ID NO: 6; g, SEQ ID NO: 7)(one experiment with mismatches and one experiment without mismatches) were formed by combining 100 μM stock solutions of the respective single stranded oligonucleotides in PBS buffer (pH 7) and incubating at room temperature for 30 minutes (Note—strands b and g were added in slight excess). 1 μl (~50 μM) of the resulting f•g (f, SEQ ID NO: 6; g, SEQ ID NO: 7) duplex solution was added to 120 μl of PBS buffer in a cuvette for fluorescence measurements (monitoring fluorescein and Cy5 channels). Then 1 μl of the remaining duplexes and lastly 2 μl (100 μM) of a was added at time points indicated. (a) is SEQ ID NO: 1, (b) is SEQ ID NO: 2, (c) is SEQ ID NO: 3, (d) is SEQ ID NO: 4, (e) is SEQ ID NO: 5, (f) is SEQ ID NO: 6, and (g) is SEQ ID NO: 7.

Cascade sequences were designed to have minimal (ideally none) secondary structure, and to have minimal non-desired base-pairing with any other sequence in the cascade. This was achieved using the software NUPACK. (see e.g., FIG. 2)

Figure 3A:
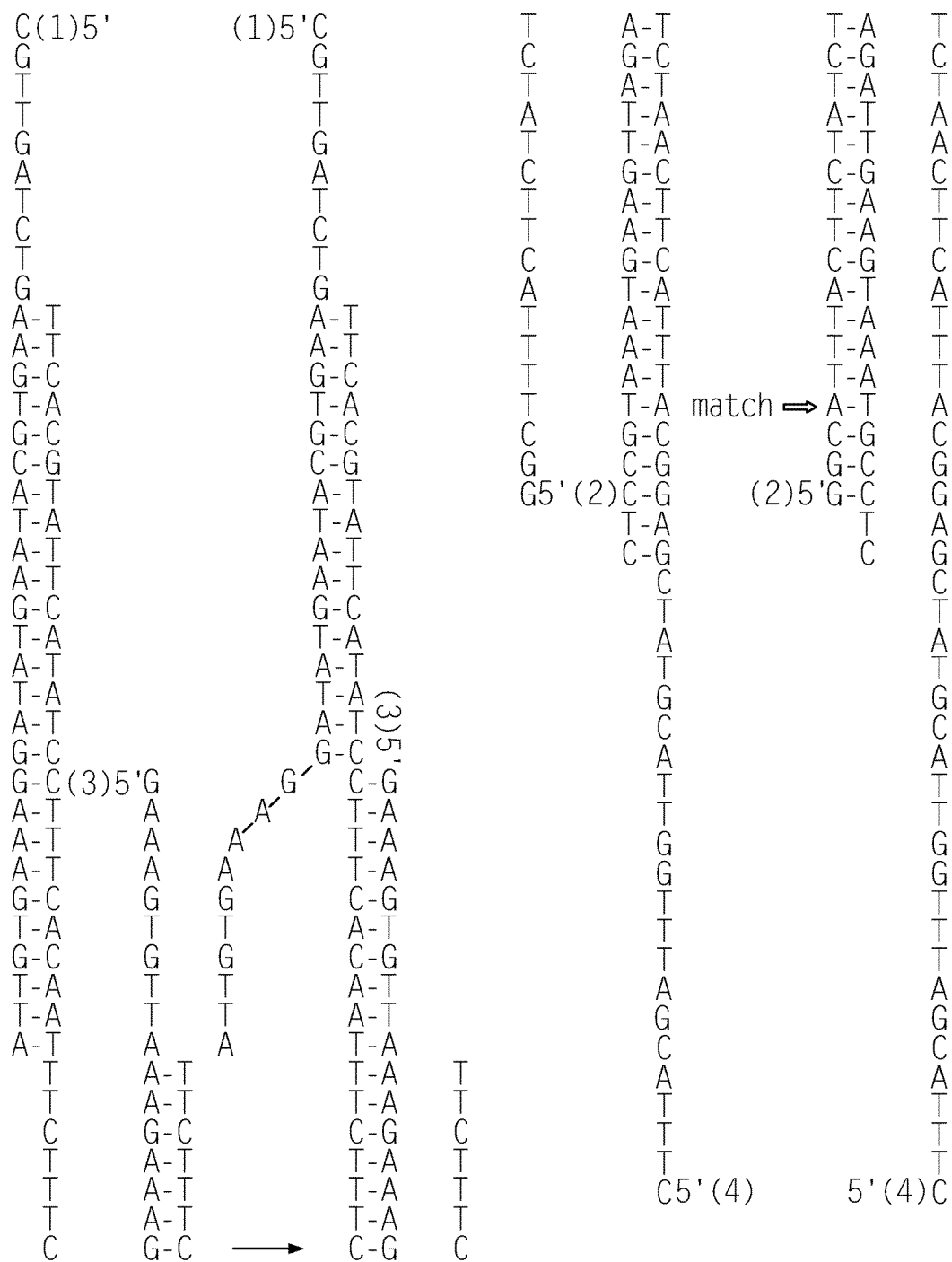
FIG. 3A-FIG. 3B is a series of oligonucleotide sequences showing the use of mismatches to diminish signal 'leak'.
Figure 3B:
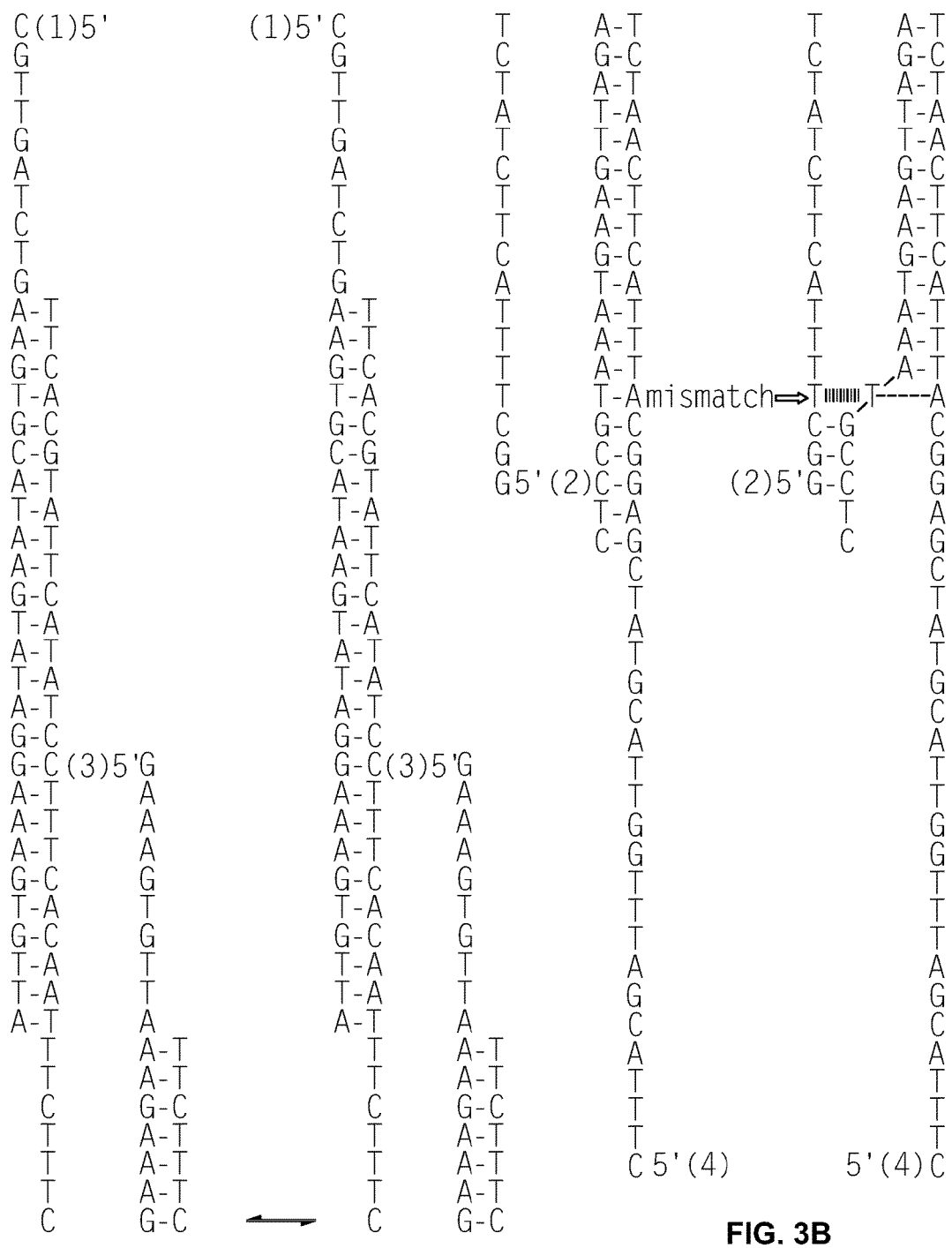
Figure 4D:
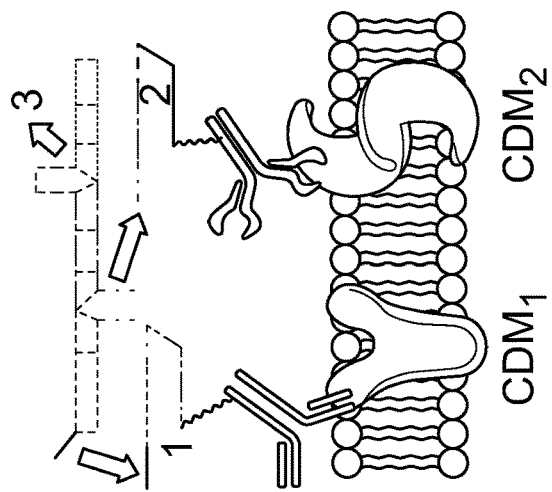
Figure 4C:
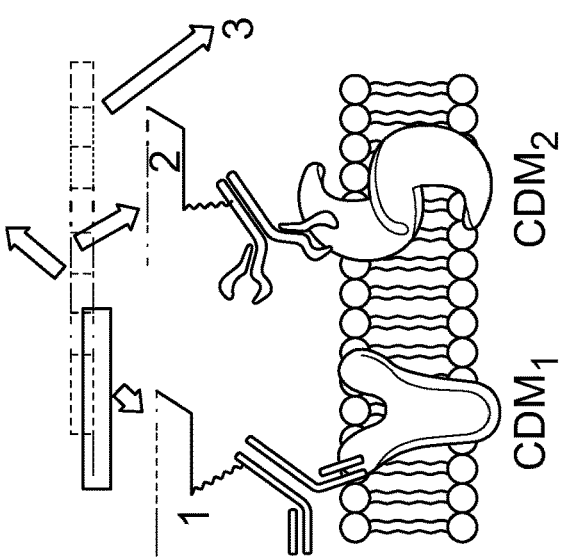
Figure 4B:
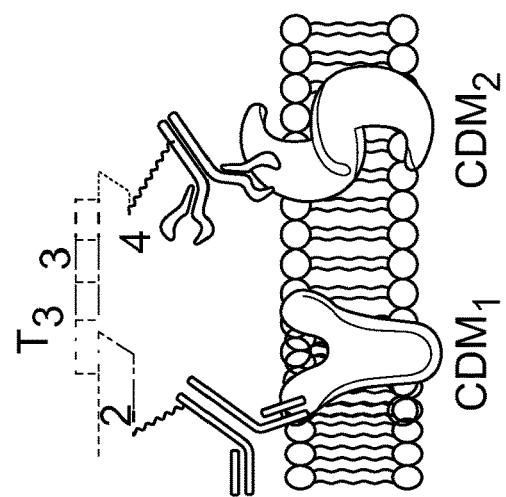
Figure 4E:
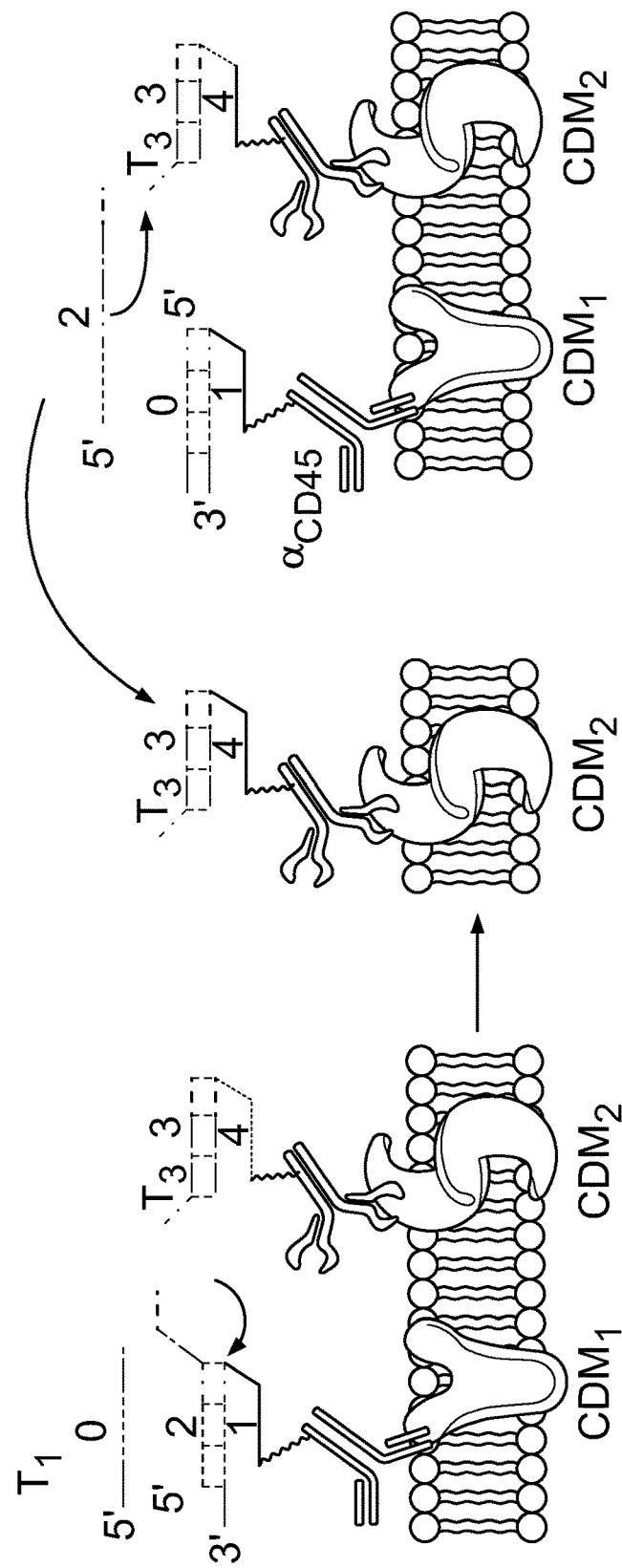

Two nucleotides were added to the 3' ends of sequences for strands 3 and 5 in the YES-YES and YES-NOT cascade and to strands 5 and 7 in the YES-YES-YES cascade, to inhibit unwanted strand invasion by the 5'-ends of sequences 2 and 4, and 4 and 6, respectively. By optimizing the operation of the cascades in solution, signal 'leakage' was minimized by addition of mismatches (see e.g., FIG. 2 and FIG. 3).

Example 4

Sample Staining

The following example describes the materials used for staining samples.

Samples were stained with CD4 APCCy7, CD19 PerCp Cy5.5 (eBioscience), CD45RO Pacific Blue and CD45RA PE (BioLegend). Further materials used in the following examples include: 7-aminoactinomycin-D (7-AAD) (Sigma) and was used in final concentration 2 µg/ml, 1× BD FACS Lysing Solution (BD Biosciences), ImmunoPure Streptavidin (ThermoScientific), and anti-FITC MicroBeads (MiltenyiBiotec GmbH).

Example 5

Cell Culture

The following example describes the materials and methods used in cell culture.

Peripheral blood mononuclear cells (PBMC) were isolated on a Ficoll-Paque Plus (GE HealthCare) gradient from whole blood or buffy coat obtained from NYC Blood center. Cells were washed and stained in PBS (Sigma) buffer, supplemented with 2% FBS (Gibco), and 1.2 mM $MgCl_2$ (Ambion).

Example 6

Flow Cytometry

The following example describes the materials and methods used in flow cytometry.

FACSCanto (Becton Dickinson) flow cytometer with 405 nm, 488 nm, and 633 nm excitation wavelengths was used for flow cytometry measurements. Instrument setup was performed by using CST beads. Fluorescence compensation was performed by single staining using anti-mouse Ig, k/Negative Control (FBS) Compensation Particles Set (BD CompBeads, BD Biosciences). Amplifier settings for forward scatter and side scatter were used in linear mode and for fluorescence channels, logarithmic mode was used. Events were gated based on the forward scatter versus side scatter and fluorescence intensities versus time. Kinetics experiments were recorded for around 30 minutes. Cells analysis was performed at the rate of 12 µl per min. The fluorescence intensities of each event were measured using 530 (30 nm band pass), 660 nm (20 nm band pass) and 450 nm (50 nm band pass), 585 nm (42 nm band pass), 780 nm (60 nm band pass) filters, respectively. The data was transferred and analyzed with FlowJo software version 9.4.11.

Example 7

Synthesis of Antibody-Oligonucleotide Conjugates

The following example describes the synthetic procedure of Rituxan-oligonucleotide conjugate and general synthesis for an antibody-oligonucleotide conjugates.

Part 1—Activated (S1) oligonucleotide (26 nmoles, 200 µl from 130 µM stock) was combined with excess 1,6-bismaleimidohexane (BMH) (200 µl of 1.44 mg/802 µl in DMSO, i.e. 1300 nmoles {50-fold excess}). The reaction mixture (50% DMSO) was incubated at room temperature for 1 hour and then split in two and each half precipitated with cold ethanol (1.5 mL) by leaving at −20° C. for 45 mins. The precipitate was separated by centrifugation and the pellet washed twice with cold ethanol and dried in vacuo. The dried pellets were resuspended in water and applied to a NAP5 desalting column (GE Healthcare) to remove any remaining traces of free BMH. The eluent was frozen and lyophilized.

Part 2—The following was carried out using aseptic techniques. 700 µl of rituximab (1.4 mg, 9.7 nmoles) (1000 mg/500 mL, 5% dextrose, 0.01% $NaN_3$) was buffer exchanged with 0.1 M sodium phosphate pH 8.0 buffer containing 1 mM EDTA via Zeba desalting column ("2 mL", Pierce). DTT (10 mM stock) was added to the resulting solution to give a final DTT concentration of 0.1 mM. The reaction mixture was incubated at 37° C. overnight (22 hrs). Unreacted DTT was removed using two subsequent Zeba desalting columns, eluting with PBSE (PBS with 5 mM EDTA), pH 6.8. The final concentration of rituximab was 9.3 uM determined by UV-vis ($\varepsilon 280$ nm=1.7 mL/(mg×cm) i.e. 240,000 $M^{-1}$ $cm^{-1}$). Using Ellman's reagent it was determined that there were on average six sulfhydryl groups per antibody (i.e. reduction of 3 disulfide bonds). The activated antibody was kept on ice.

For anti-human CD3, CD8, and CD45, the antibodies were buffer exchanged with 0.1 M TRIS, pH 8.0 and DTT added to give a concentration of 5 mM, then incubated at 37° C. for 30 mins. (S2) Theses antibodies were then purified and characterized as above.

Part 1 and Part 2 products were then combined, for example, 1 nmole of activated oligonucleotide (4.3 µl) was added to 0.25 nmoles of activated rituximab (27 µl) i.e. 4:1 oligo:antibody (see e.g., FIG. 4 for results). For coupling double helical DNA to the antibody, a slight excess of complementary strand was added to the activated oligonucleotide from Part 1 with incubation for 30 mins, then this combined with Part 2 (see e.g., FIG. 3 for results). Purification was carried out by size exclusion chromatography on a Superdex 200 10/300 GL column (GE Healthcare) with an Åkta purifier system (GE Healthcare).

Example 8

3-Step and 2-Step Cascade Protocol

The following example describes the protocol for the preparation and analysis of the 3-step cascade, yesCD8yesCD3yesCD4, and 2-step cascades.

A mixture of the antibody-oligonucleotide conjugates were incubated with 1.5×10⁶ cells at a final concentration of 0.1 µM (or 7.5 µg antibody/ml), each duplex in a final volume of 100 µl, on ice for 20 minutes. After incubation the cells were washed twice with 2.5 ml of cold buffer on 300×g for 5 minutes at +4° C. (Eppendorf Centrifuge 5804 R). The pellet was resuspended in 400 µl of buffer and then run on a FacsCanto (BD Bioscience) flow cytometer to measure Fluorescence intensity vs Time. Duplex 5•6 and trigger 0 were added to a final concentration of 0.5 µM in real time during measurement.

Example 9 yesCD8yesCD3 Cascade in Whole Blood

The following example describes the protocol for the preparation and analysis of yesCD8yesCD3 cascade in whole blood.

Antibody conjugated duplexes 3•4$_{\alpha CD8}$ and 1•2$_{\alpha CD3}$ were added to 300 µl of whole blood cells at a final concentration of 1.5 µg of antibody/ml and incubated for 15 minutes at room temperature. Afterwards, 4 µl of duplex 5•6 was added to a final concentration of 0.5 µM, incubated 15 minutes, followed by trigger 0 at a final concentration of 1 µM and incubated for a further 15 minutes at room temperature. To examine the result of the cascade reaction, red blood cells were lysed with 1× BD FACS Lysing Solution in the dark at

Example 10

YESCD8NOTCD45RA CASCADE

The following example describes the protocol for the preparation and analysis of YESCD8NOTCD45RA cascade.

αCD45RA was conjugated to duplex 5*•6* via biotin-streptavidin coupling (assembly in situ method without purification of conjugates). Specifically, 1.5 million PBMCs were incubated with 0.5 μg of biotinylated anti-human antibody CD45RA in a final volume of 100 μl of cold buffer for 20 minutes on ice. Then, the cells were washed twice with 2.5 ml of cold buffer by centrifugation (300×g, 5 minutes, at 4° C.). The next incubation was performed with 0.5 μg of ImmunoPure Streptavidin in a final volume of 100 μl of cold buffer, for 20 minutes on ice. The cells were then washed by centrifugation as above and biotinylated duplex $5*•6*_{biotin}$ was added at a final concentration of 0.1 μM in a final volume of 100 μl of cold buffer for 20 minutes on ice. The cells were then washed twice as described above. Next, a final concentration of 0.1 μM of $3•4_{\alpha CD8}$ was added together with αCD4 and αCD19 antibodies and the cells were incubated for 20 minutes on ice. After incubation, the cells were washed twice by centrifugation as described above, and resuspended in a total volume of 400 μl of buffer. During flow cytometric analysis, duplex 5•6 and trigger 2, at a final concentration 0.5 μM and 1 μM respectively, were added in real time at room temperature.

The biotin coupling method was not used on more than one antibody, because it was observed, in this case, a noticeable exchange of oligonucleotides between two biotinylated antibodies (5-20%), which makes data analysis more difficult and results less clear-cut (i.e., the observation could need to be "corrected").

Example 11

Magnetic Beads Separation of Cells (YESCD45YESCD3)

The following example describes the separation of cells with magnetic beads.

$3•4_{\alpha CD3}$ was attached to the PBMC cell surface via biotin-streptavidin, as previously described. PBMCs were then incubated with $1•2_{\alpha CD45}$ (0.1 μM) for 20 minutes on ice. The cells were washed twice by centrifugation (300×g, 5 minutes, at 4° C.) and incubated with 0.5 μM oligonucleotide duplex 5•6 at room temperature for 5 minutes. Cells were washed and trigger 0 (1 μM final concentration) was added and incubated for 20 minutes. Afterwards, cells were washed with 15 ml of buffer and incubated with Anti-FITC Micro beads (MiltenyiBiotec GmbH) as described in the kit protocol.

Example 12

Isolation and Enrichment of Subpopulations of T- and B-, $CD8^{POS}$-, and $CD4^{POS}$-Cells The following example describes the isolation and enrichment of subpopulations of T- and B-, $CD8^{pos}$-, and $CD4^{pos}$-cells.

Isolation of subpopulations of T- and B-, $CD8^{pos}$-, and $CD4^{pos}$-cells was performed using Pan T Cell Isolation Kit II, B Cell Isolation Kit II, CD8+ T Cell Isolation Kit (all from MiltenyiBiotec) and Negative Selection Human CD4+ T Cell Enrichment Kit (StemCell Technologies). The enrichment was accomplished precisely as described in the original kits protocols.

To assess the purity of the enriched T- and B-, $CD8^{pos}$-, and $CD4^{pos}$-subpopulations, cells were stained with the following fluorochrome-conjugated antibodies: CD4 Pacific Blue (eBioscience, clone OKT4), CD8 PECy7 (BioLegend, cloneSK1), CD20 APC (eBioscience, clone 2H7), CD3 PE (eBioscience, clone UCHT1), CD45 Pacific Orange (Invitrogen, clone 2D1).

Example 13

Concentration Determination by UV-Vis Spectroscopy

The following example describes the procedure for determining the concentration of oligonucleotides by UV-vis spectroscopy.

For example, absorption coefficients for rituximab at 280 nm is 240,000 $M^{-1}$ $cm^{-1}$, and at 260 nm is 126,000 $M^{-1}$ $cm^{-1}$. Absorption coefficient for two-step cascade strand (4) oligonucleotide is 480,000 $M^{-1}$ $cm^{-1}$.

Figure 5:
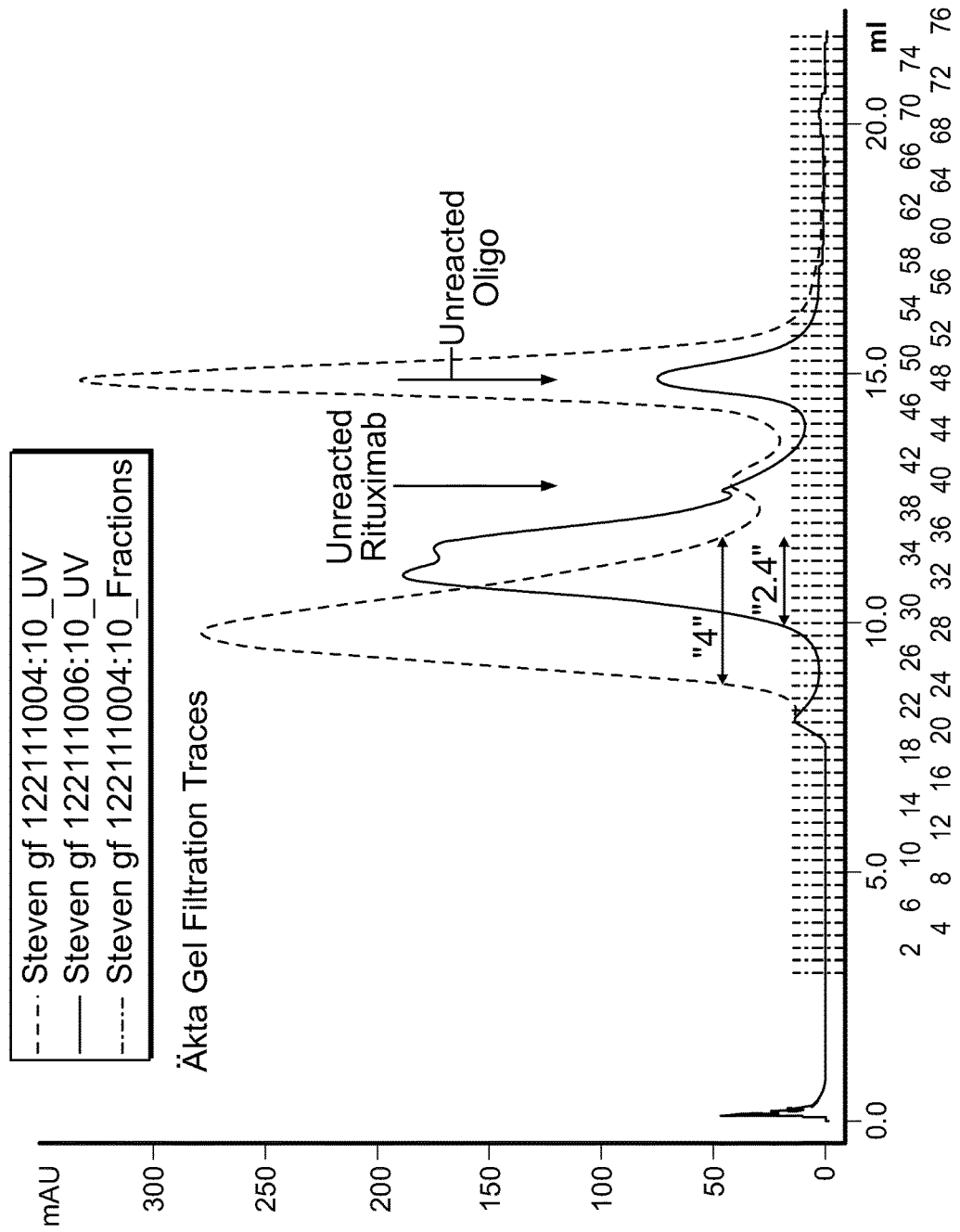
FIG. 5 is a size exclusion chromatograph spectrum showing the purification of rituximab-oligonucleotide conjugates. Sample "4" are products isolated from the reaction of 4 equivalents of oligo-BMH with one equivalent of sulfhydryl-rituxan. Sample "2.4" are products isolated from the reaction of 2.4 equivalents of oligo-BMH with one equivalent of sulfhydryl-rituxan. For other antibodies, 4 equivalents of oligonucleotide were used.

By adding 1, 2, 3, 4, 5, 6, and 7 equivalents of oligonucleotide to one equivalent of rituximab, the following A260 nm/A280 nm ratios were found: 1.12, 1.33, 1.41, 1.46, 1.50, 1.52, and 1.54 respectively (see e.g., FIG. 5).

For the "4" sample, the 260/280 ratio was found to be 1.52, and for the "2.4" the 260/280 ratio was 1.38, corresponding to an average of 6.0 oligonucleotides per rituximab for the "4" sample, and 2.9 oligonucleotides per rituximab for the "2.4" sample (see e.g., FIG. 5). Therefore, the absorption coefficient for the "4" sample is (126,000+6× 480,000)$M^{-1}$ $cm^{-1}$=3,010,000 $M^{-1}$ $cm^{-1}$, and using Beer's Law, the concentration of '6:1' conjugate in the sample is 3.14 μM, which implies an absolute oligonucleotide concentration of 19 μM (see e.g., FIG. 5). Analogously, the concentration of '2.9:1' conjugate (abs coeff.=1,520,000 $M^{-1}$ $cm^{-1}$) in the sample "2.4" is 1.2 μM, which implies an absolute oligo concentration is 3.4 μM (see e.g., FIG. 5).

Example 14

Blood Cells as Targets for Molecular Automata

The following example describes the targets used for molecular automata.

Figure 6A:
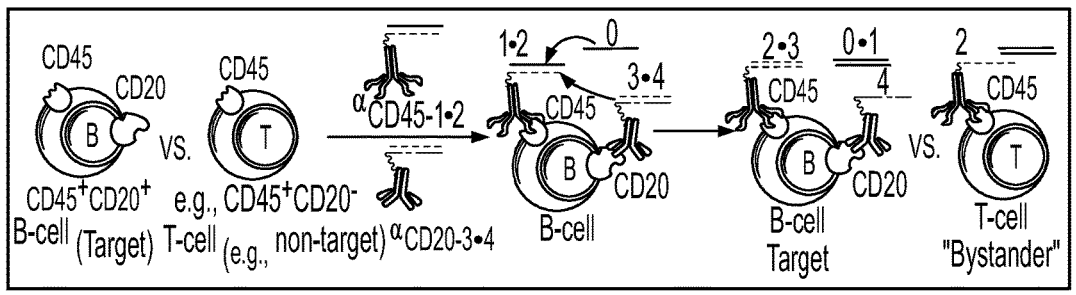
FIG. 6A-FIG. 6C is a series of drawings showing the design considerations for automata operating on cell surfaces.
Figure 6B:
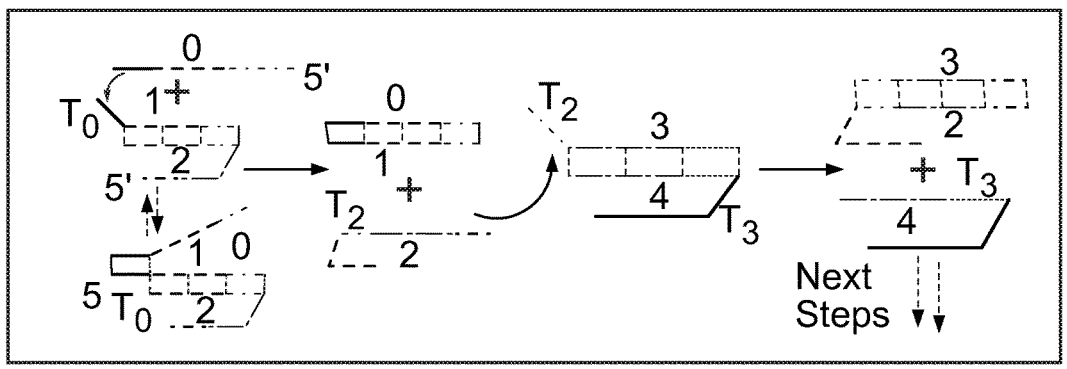
Figure 6C:

Blood cells were chosen as targets for molecular automata, as they are the most exhaustively studied examples of cells with lineages and stages of differentiation defined by the presence or absence of multiple cell surface markers. Blood cells are commonly characterized by flow cytometry via different levels of expression of multiple cell surface markers known as Clusters of Differentiation or CDs, with CD45s, CD20, CD3, and CD8 used as examples herein. Here the basic design principles for automata that can tag lymphocytes with targeted markers characteristic for B-cells (i.e., $CD45^+CD20^+$ cells) in the presence of $CD45^+CD20^-$ cells (e.g., $CD45^+CD3^{+'}$ T-cells) is shown (see e.g., FIG. 6).

Example 15

Program Execution

Figure 7:
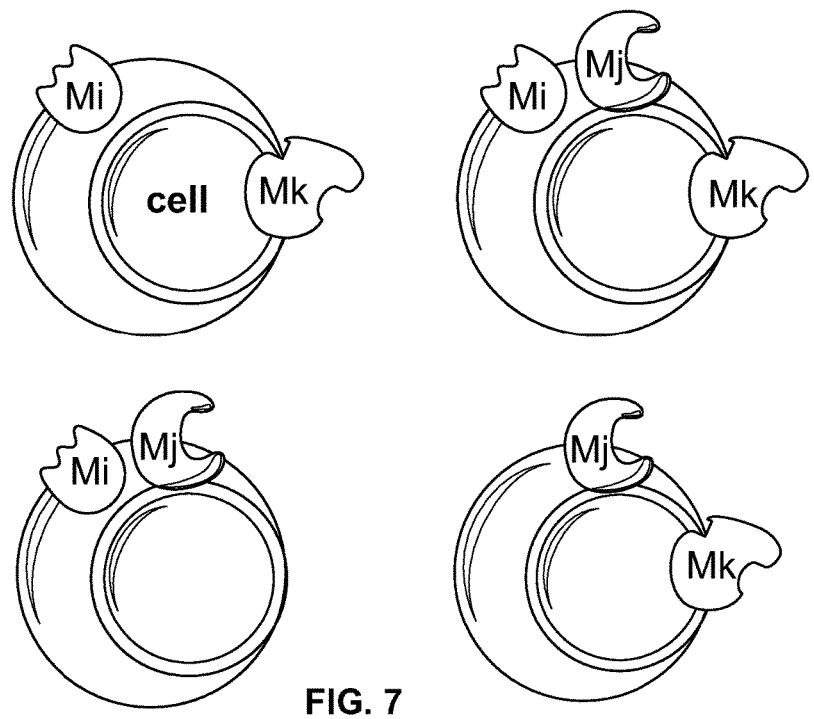
FIG. 7 is a series of drawings illustrating four examples of molecular automata for evaluation of cell surfaces.
Figure 8:
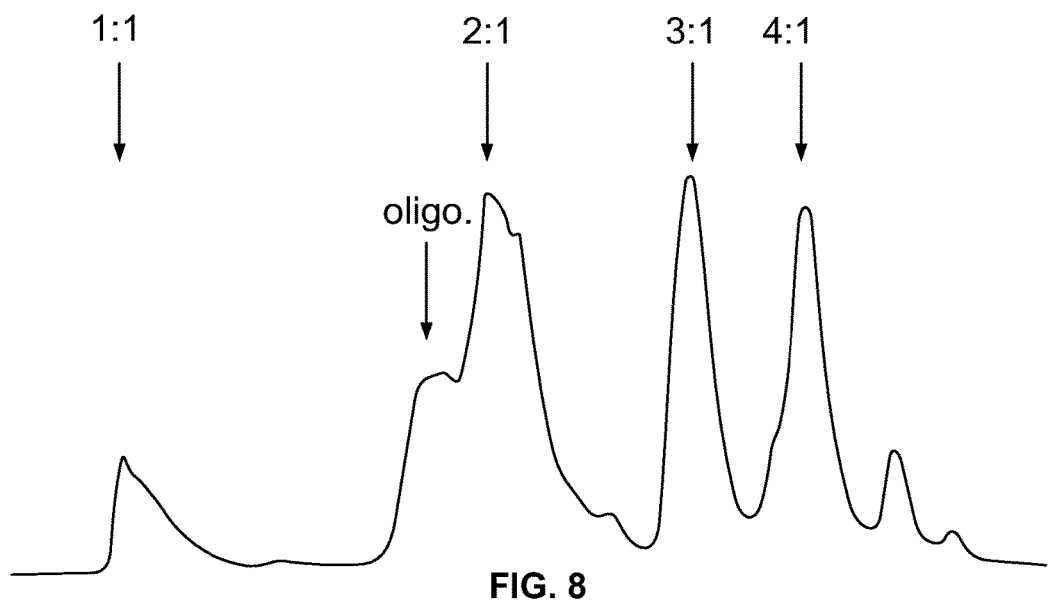
FIG. 8 is a HPLC spectrum showing the anion exchange HPLC analysis/purification of rituxan-oligonucleotide conjugates carried out on a Shimadzu LC-20AB pump equipped with an SPD-M20A PDA detector using a Tosoh Biosciences TSKgel DEAE-NPR column, 4.6×50 mm (IDxL). Buffer A was composed of 20 mM TRIS, and buffer B, 20 mM TRIS/1 M NaCl, both adjusted to pH 7.2.). Ratios of oligonucleotide:antibody are arrowed above the respective peak, and were determined by comparing the UV absorbance 260 nm/280 nm ratio with standards made from non-conjugated oligonucleotide and antibody. Each peak was checked for activity via its performance in a YES-YES cascade, and it was found that all peaks were active with performance increasing as oligonucleotide:antibody ratio increased. For all cascade experiments, however, all oligonucleotide-antibody conjugates were purified by size-exclusion FPLC due to increased yield (see e.g., FIG. 2).
Figure 9:
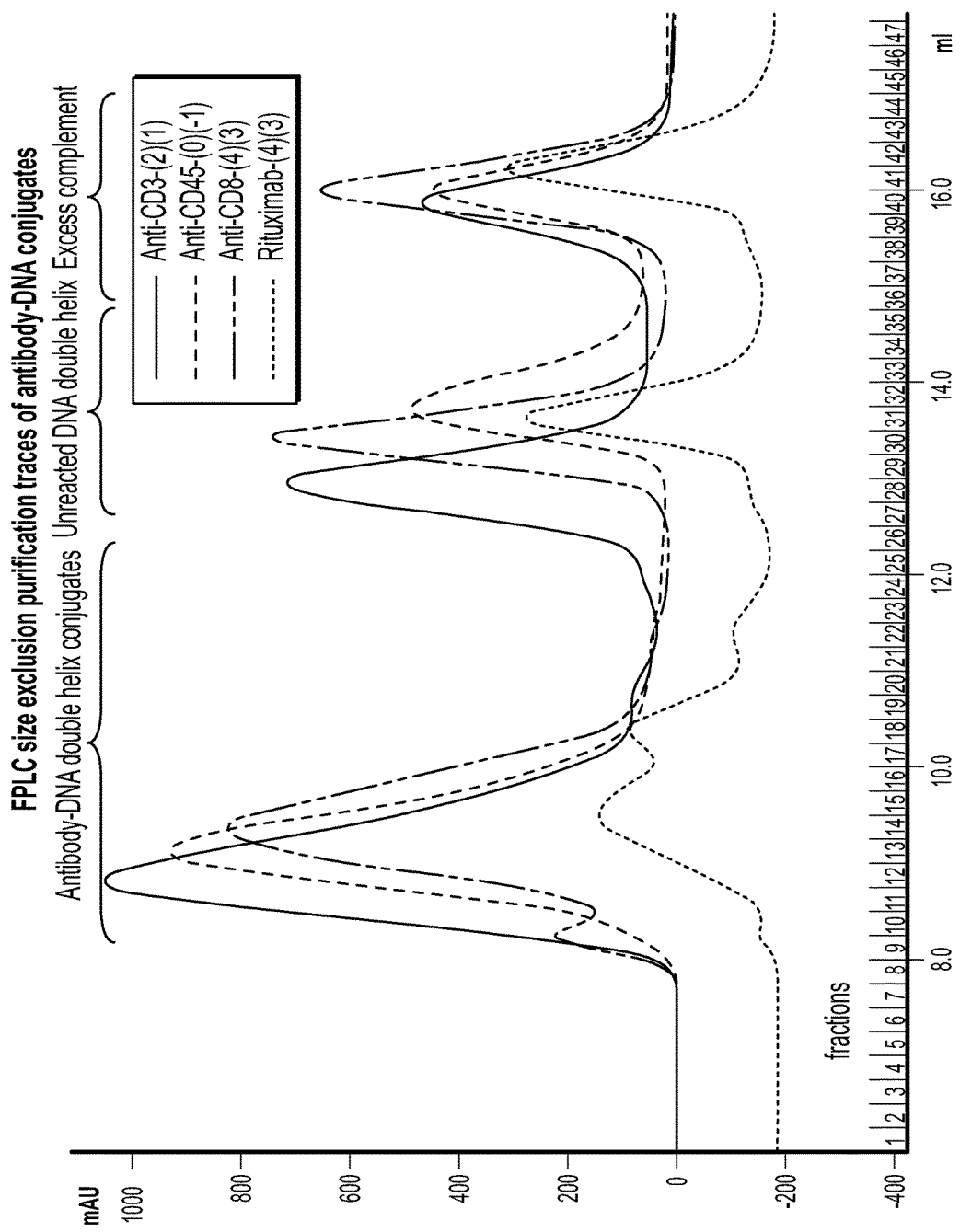
FIG. 9 is a series of size exclusion chromatograph traces showing the purification of antibody-DNA double helix conjugates. Initial fractions (e.g. for 3•4$_{Rituxan}$, fractions 12, 13, and 14) were preferred for running cascade experiments due to results obtained in FIG. 3A-FIG. 3B.

The following example describes the automata program execution. The "program" (conditional sequential transitions) that an automaton can execute on the surfaces of lymphocytes can be defined by a set of antibodies against markers $M_i$ directing cascades of chemical reactions on cell surfaces (see e.g., FIG. 6, FIG. 7 with CD20 and CD45 as Mi's).

The well-established antibodies targeting CD markers (αCD45, αCD45RA, αCD20 (Rituximab), αCD3, and αCD8) were used as antibodies against markers, Mi. All of these antigens are present at between 80 and 200 thousand copies per cell surface on targeted subpopulations of lymphocytes, ensuring strong signal when measured by flow cytometry. These antibodies were conjugated with a set of partially complementary oligonucleotides (1•2, 3•4, and 5•6) optimized to execute, when triggered with oligonucleotide 0, modified strand-displacement cascades (see e.g., FIG. 2, FIG. 3, FIG. 4, FIG. 5, FIG. 6B, FIG. 6C, FIG. 8, FIG. 9).

Once turned on, such an automaton would ask a series of questions regarding the presence on the same cell surface of different markers via oligonucleotide transfers enabled by sequential exposure of new toeholds (cf. FIG. 4B), executing 'if YES $M_i$ then proceed' or 'if NOT $M_i$ then proceed' functions.

Example 16

Automata Evaluation of Two Surface Markers

The following example describes the demonstration of the ability of the automata to evaluate two surface markers.

Figure 10A:
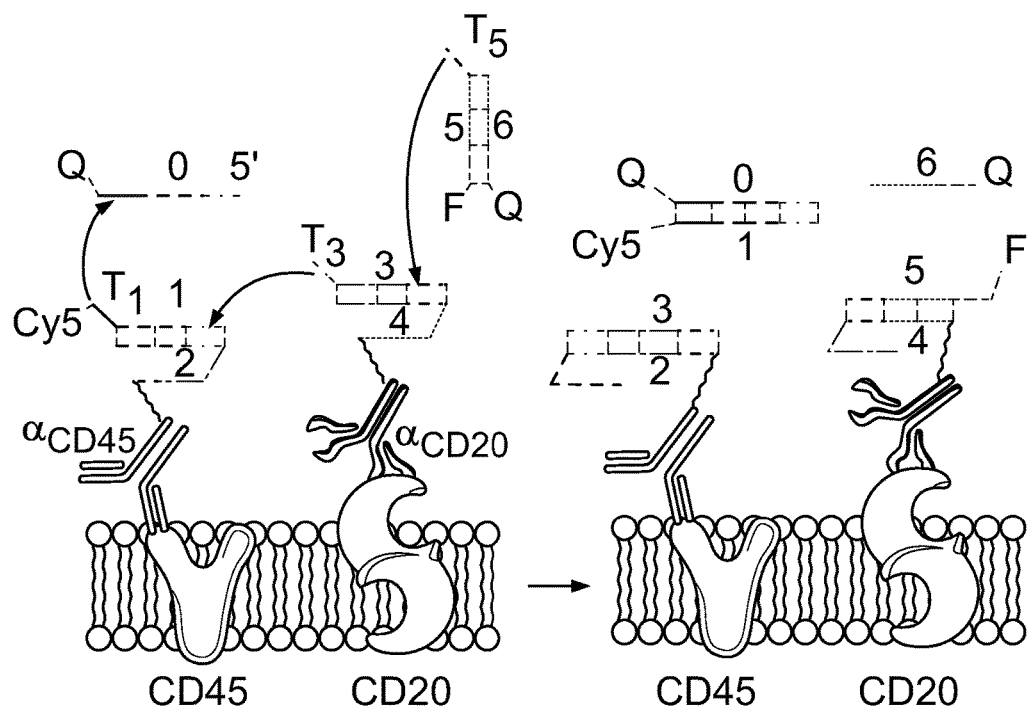
FIG. 10A-FIG. 10C is a series of drawings and spectra showing the demonstration of an automata assessing the presence of two cell surface markers.
Figure 10B:
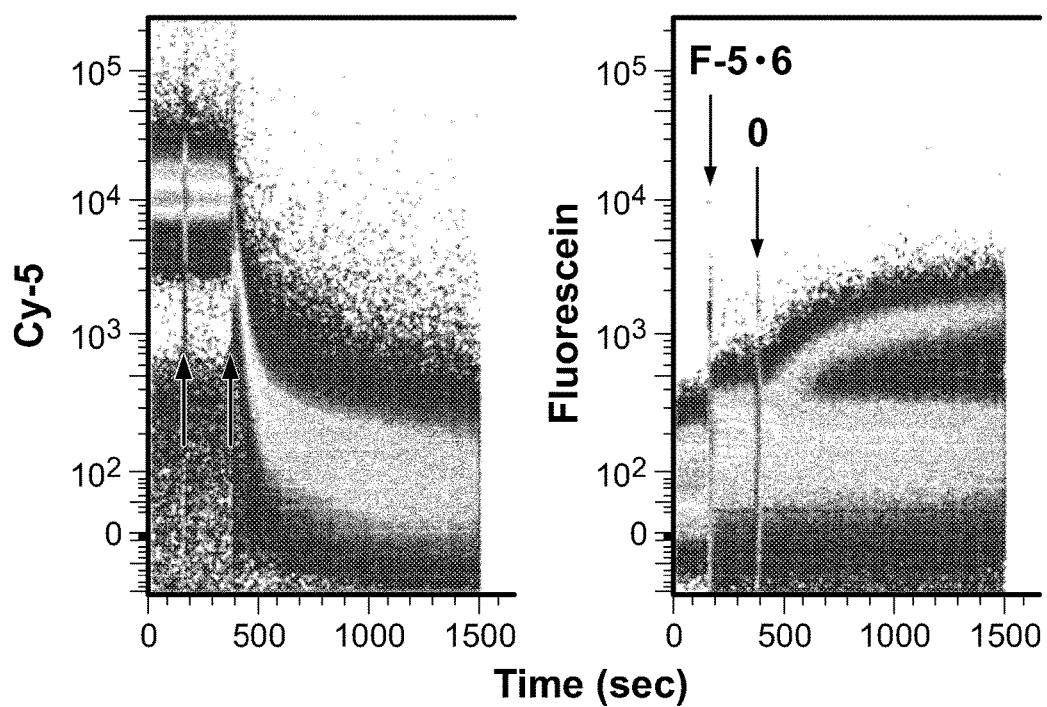
Figure 10C:
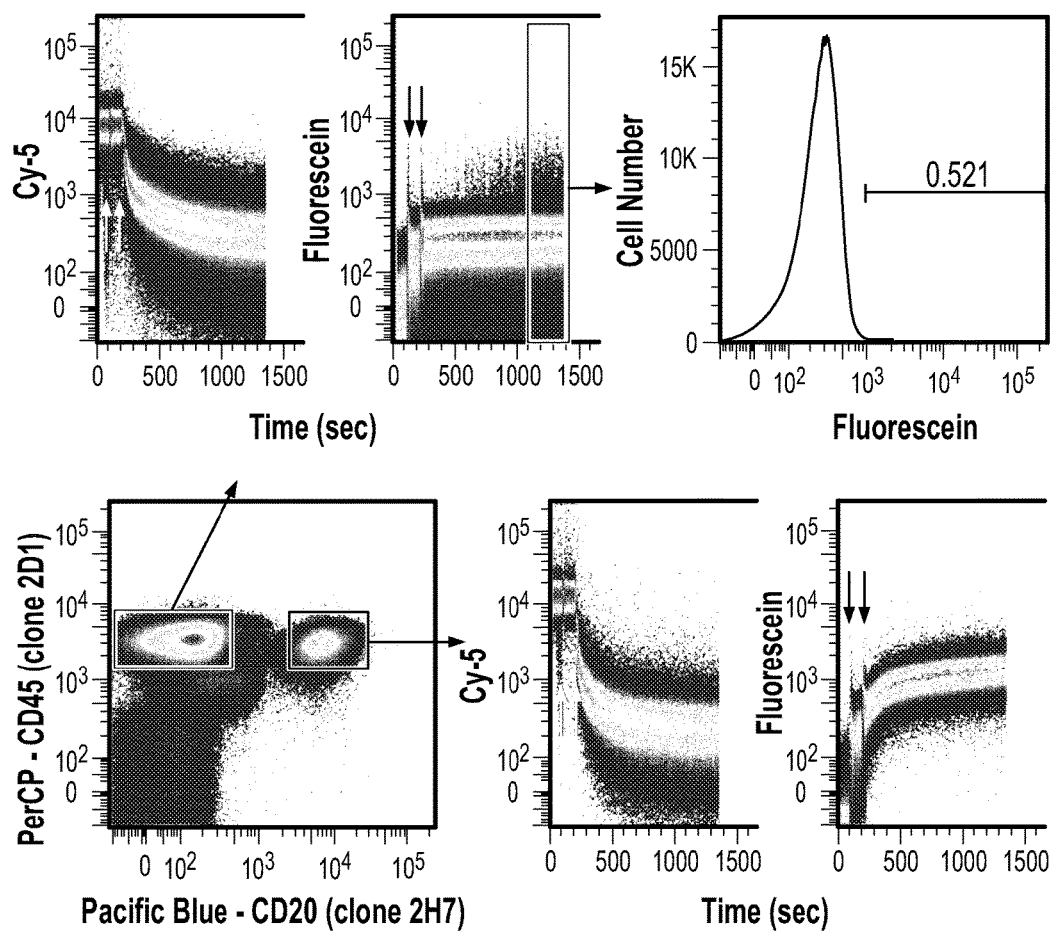
Figure 11A:
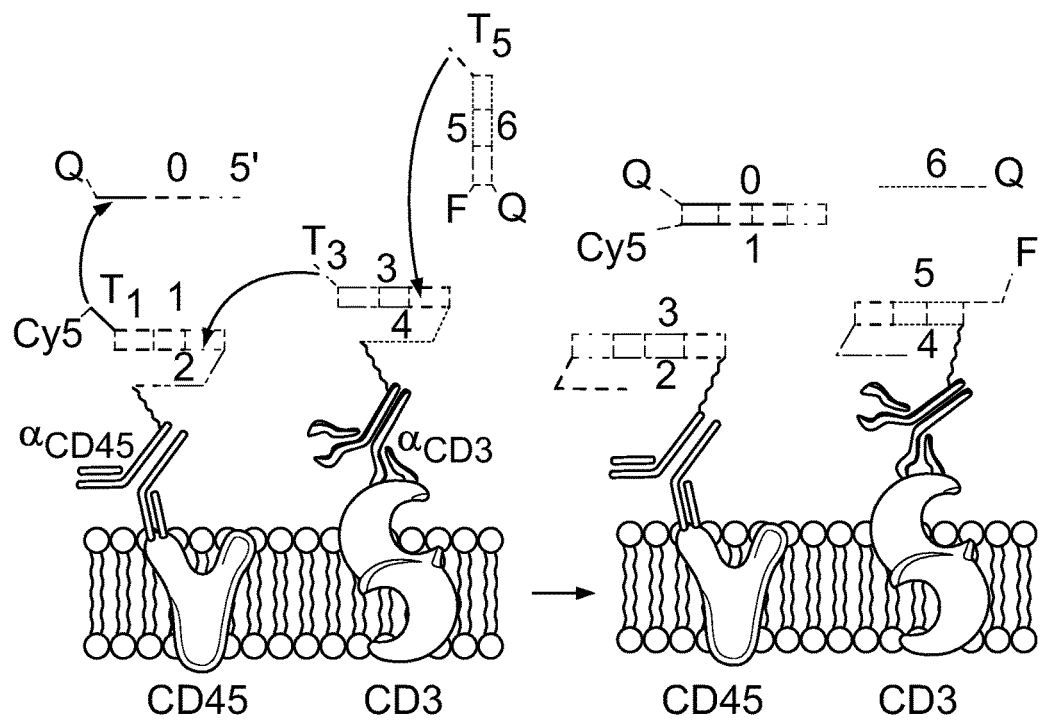
FIG. 11A-FIG. 11E is a series of drawings and flow cytometry fluorescence spectra demonstrating the operation of automata YESCD45YESCD3, YESCD45 (YESCD20ORYESCD3), and control YESCD3YESCD20.
Figure 11B:
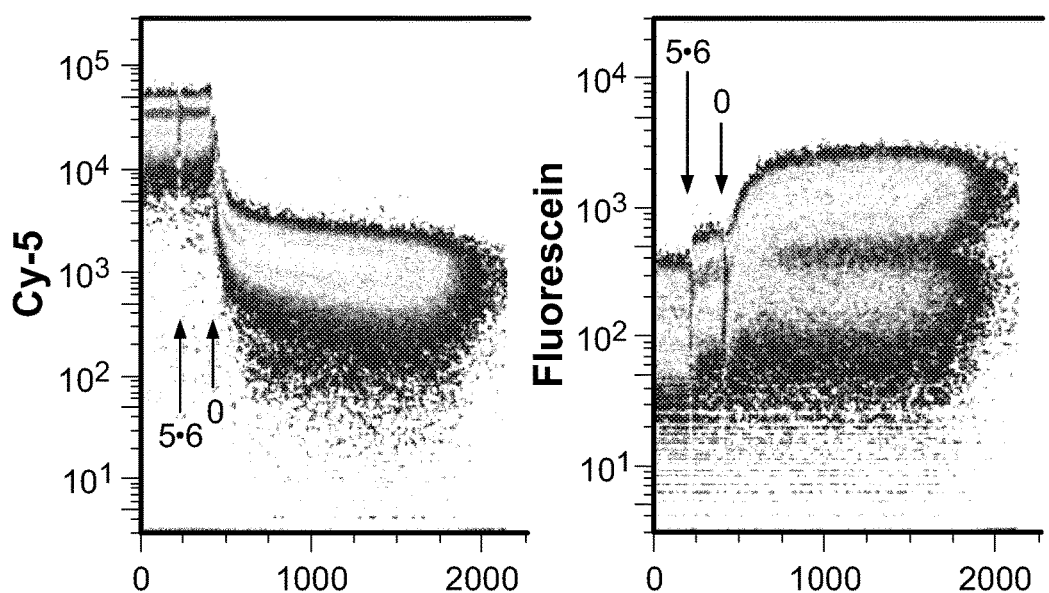
Figure 11C:
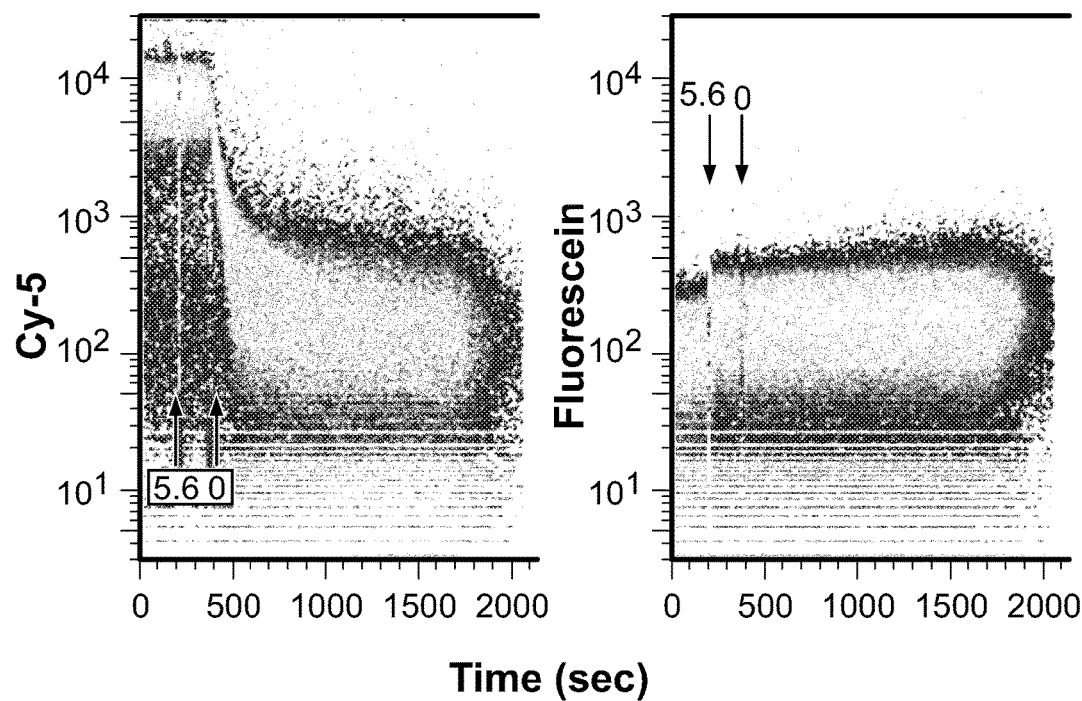
Figure 11D:
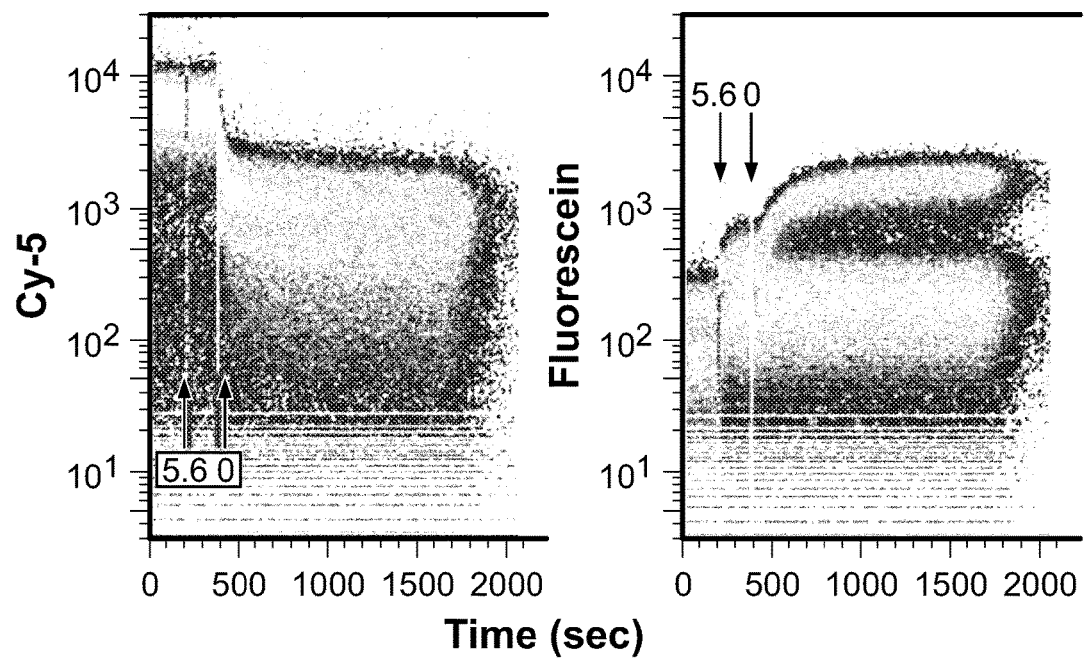
Figure 11E:
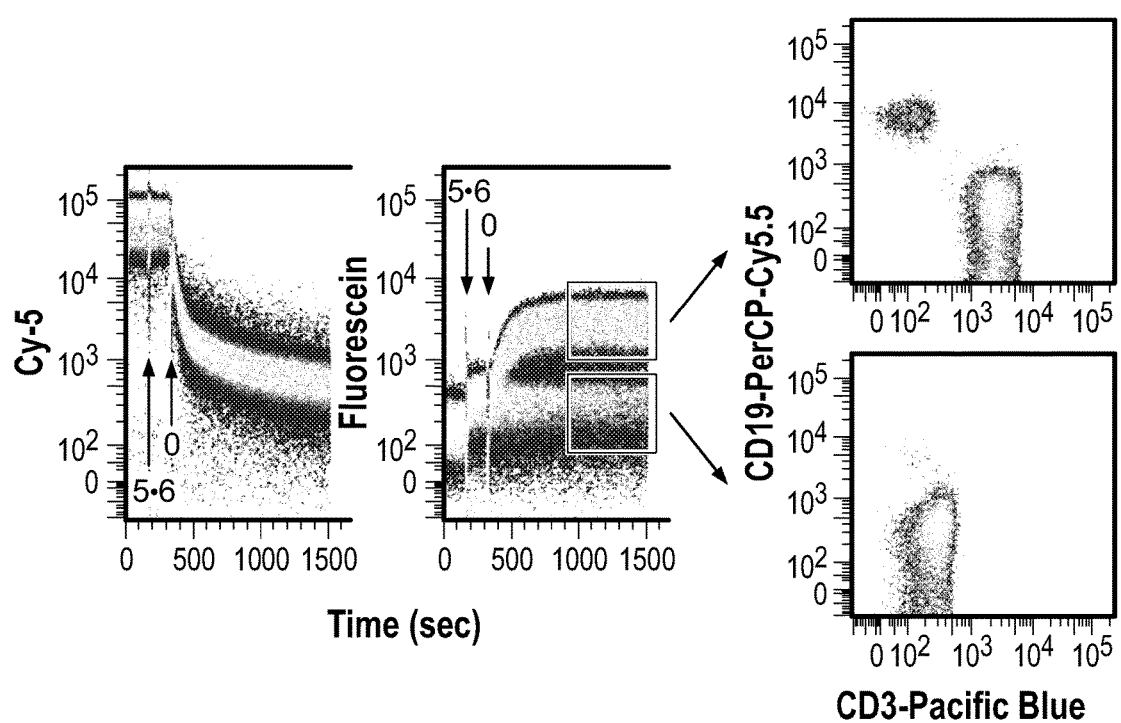
Figure 12:
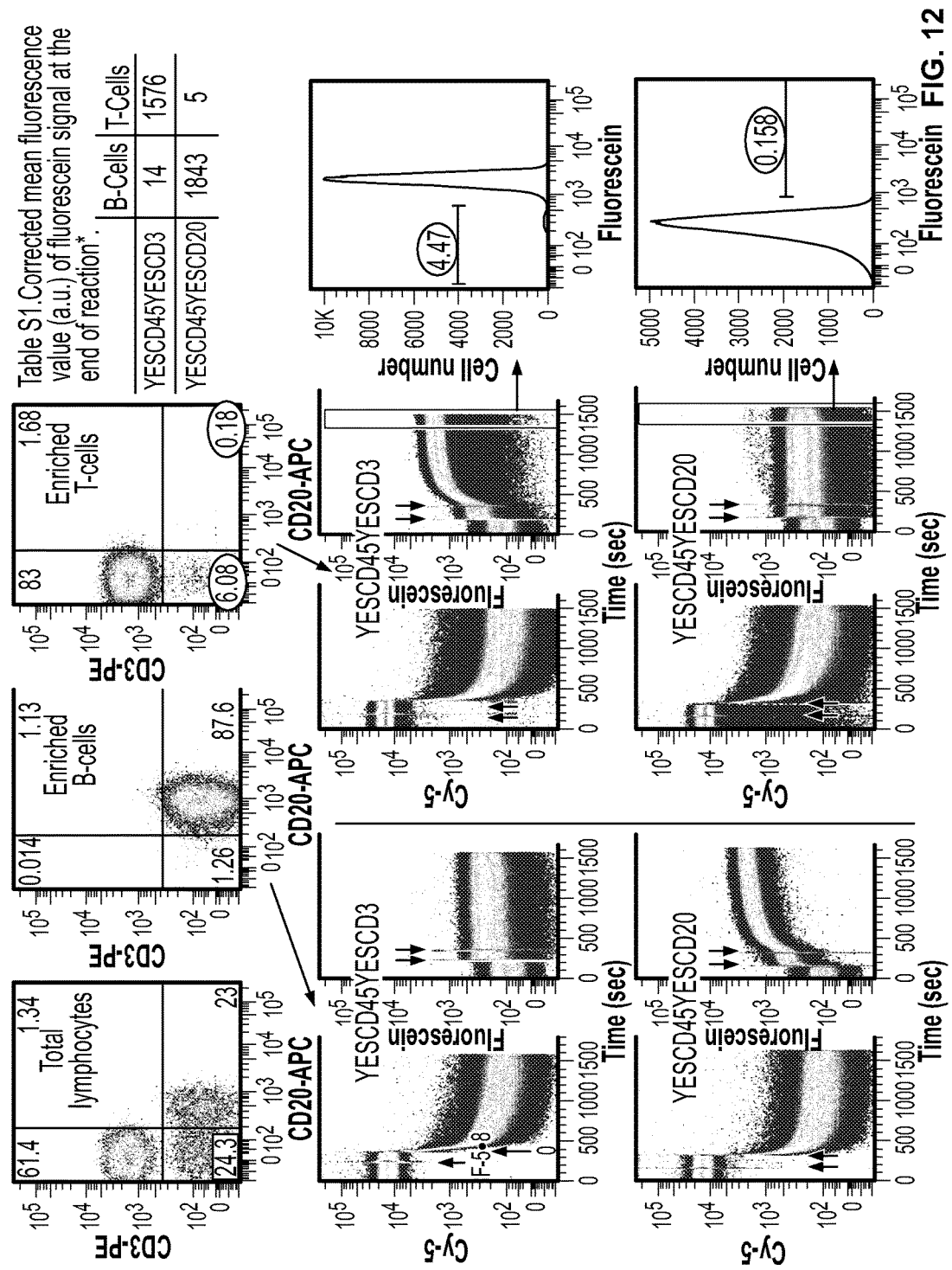
FIG. 12 is a series of fluorescence signals in a scheme showing experiments on enriched B- and T-cells, as described in FIG. 10A-FIG. 10C (mean fluorescence signal normalized to background after the addition of F−5•6 but before addition of trigger 0).

First, the ability for automata to evaluate two surface markers (see e.g., FIG. 10A for YESCD45YESCD20 experiment, functionally equivalent to CD45ANDCD20) and to selectively label one targeted subpopulation within peripheral blood mononuclear cells (PBMCs—a mixture of various lymphocytes, monocytes, and macrophages) was tested.

All possible automata that could read combinations of two out of three markers, CD45 (a marker of nucleated hematopoietic cells), CD20 (a B-cell marker), and CD3 (a pan-T-cell marker) were constructed. Two of these automata are capable of successful completion of their "program": YESCD45YESCD20 would operate (label) only on B-cells (see e.g., FIG. 10A) and YESCD45YESCD3 would operate only on T-cells (see e.g., FIG. 11). The third possible two-step automaton, YESCD3YESCD20 is a negative control, because no subpopulations in this example display these two markers simultaneously. The operation of these automata is equivalent to asking: "Is this cell a nucleated hematopoietic cell?" (YESCD45) followed by, in the case of the first automaton, "Is this a nucleated hematopoietic cell from a B-cell lineage?" (YESCD20) and, in the case of the second automaton, "Is this nucleated hematopoietic cell from the T-cell lineage?" (YESCD3). In all these automata, if both questions are answered positively in a row, the reaction performed, given here on an example of B-cells, will be: $0+1\cdot 2_{\alpha CD45}+3\cdot 4_{\alpha CD20}\rightarrow 0\cdot 1+_{\alpha CD45}2\cdot 3+_{\alpha CD20}4$, with targeted subpopulations displaying a newly uncovered single-stranded oligonucleotide, 4. This one marker can then be said to contain the same information as traditional multicolor labeling with the same antibodies that were used in construction of automata and that would otherwise be used to characterize the immunological phenotype of these cells (e.g., $CD45^+CD20^+$).

Additionally, a system was set up so the output oligonucleotide would interact with a solution phase label such as: $_{\alpha CD20}4+F-5\cdot 6\rightarrow_{\alpha CD20}4\cdot 5-F+6$ (where F is a fluorescent signal from fluorescein when not quenched by 6), and the response of targeted cells to the cascade could be directly analyzed by flow cytometry (YESCD45YESCD20→F) within a heterogenous population of cells. In order to assess the full operation of automata, 1 was labeled with Cy5, so both its removal and subsequent acquisition of fluorescein by $_{\alpha CD20}4$ on the cell surface could be monitored simultaneously in real time.

Experiments showed the first two automata successfully labeled only surfaces of either B-($CD45^+CD20^+$) or T-($CD45^+CD3^+$) cells (see e.g., FIG. 10A, FIG. 10B, FIG. 11, FIG. 12). Each outcome was confirmed three or more times on individual human blood samples and monitored by multicolor flow cytometry. From these same components an automaton was also made that could label the surfaces of both B- and T-cells by using $3\cdot 4_{\alpha CD20}$ and $3\cdot 4_{\alpha CD3}$ in the same solution (cf., FIG. 11E); a possible presentation of this automaton is that it is demonstrating an OR function, as in YESCD45(YESCD20ORYESCD3). After the successful demonstrations of these automata in mixtures of cells (PBMCs), it was also confirmed that the automata worked on enriched cell subpopulations with correct marker combinations (B- or T-cells), and that all cells that were $CD45^+CD20^+$ (or $CD3^+$) were labeled anti-CD45 and anti-CD20 (or anti-CD3) antibodies were used; cells that were negative in one of these markers were not labeled (see e.g., FIG. 12).

Example 17

Control Automata

Figure 13:
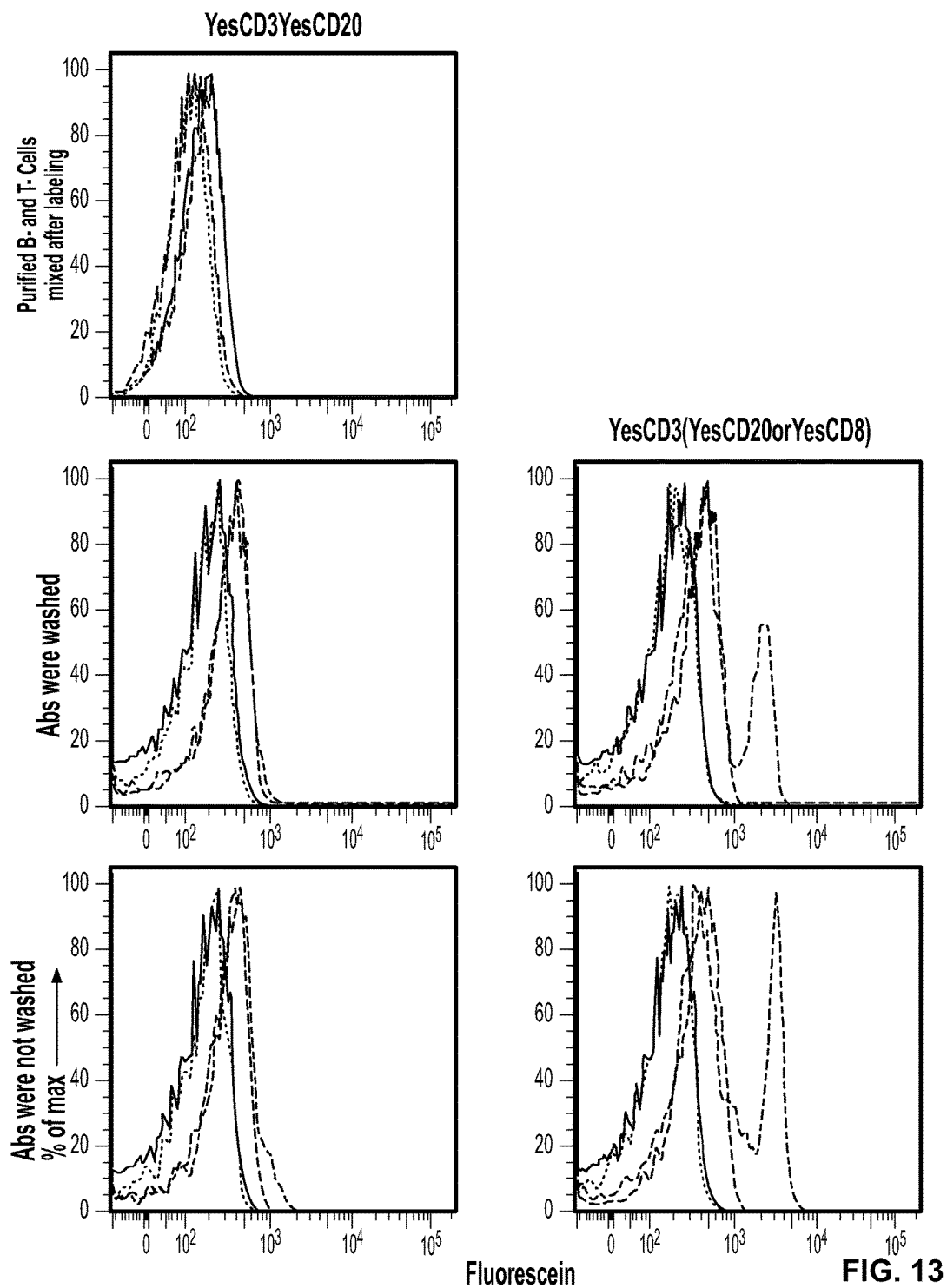
FIG. 13 is a series of fluorescence spectra showing the estimation of the bystander effects (cross-talk between different types of cells in mixture) on YESCD3YESCD20 (left column) with no cells positive for both of these markers and YESCD3(YESCD20ORYESCD8) with automata supposed to increase fluorescence only on CD8+ cells. The cells in the top panel were enriched as CD3+ and CD20+, exposed to conjugates, excess of reagents washed away, and then the cells were remixed before the reaction was triggered. Middle row panels show with cells (PBMCs), excess of conjugates were removed from cells by centrifugation and washing, while excess of reagents in solution was not removed with PBMCs in bottom. Individual traces: Red—unlabeled cells ("autofluorescence"); blue—PBMCs incubated at 4° C. for 20 minutes with anti-CD3 conjugated with duplex 1•2-Cy5 and anti-CD20 (left column) and/or anti-CD8 (right column) conjugated with duplex 3•4; green trace—same as "blue", but with F−5•6-Q added to PBMCs with cells incubated at room temperature for an additional 5 min; black—subsequent addition of 0-Q at room temperature for 20 min before measuring (where F is fluorescein and Q is the respective quencher; oligonucleotide numbering references the two-step YES-YES cascade). Comparison of black and green traces allows us to assess cascades that occur between two cells, as opposed to cascades that occur only on one cell.
Figure 14:
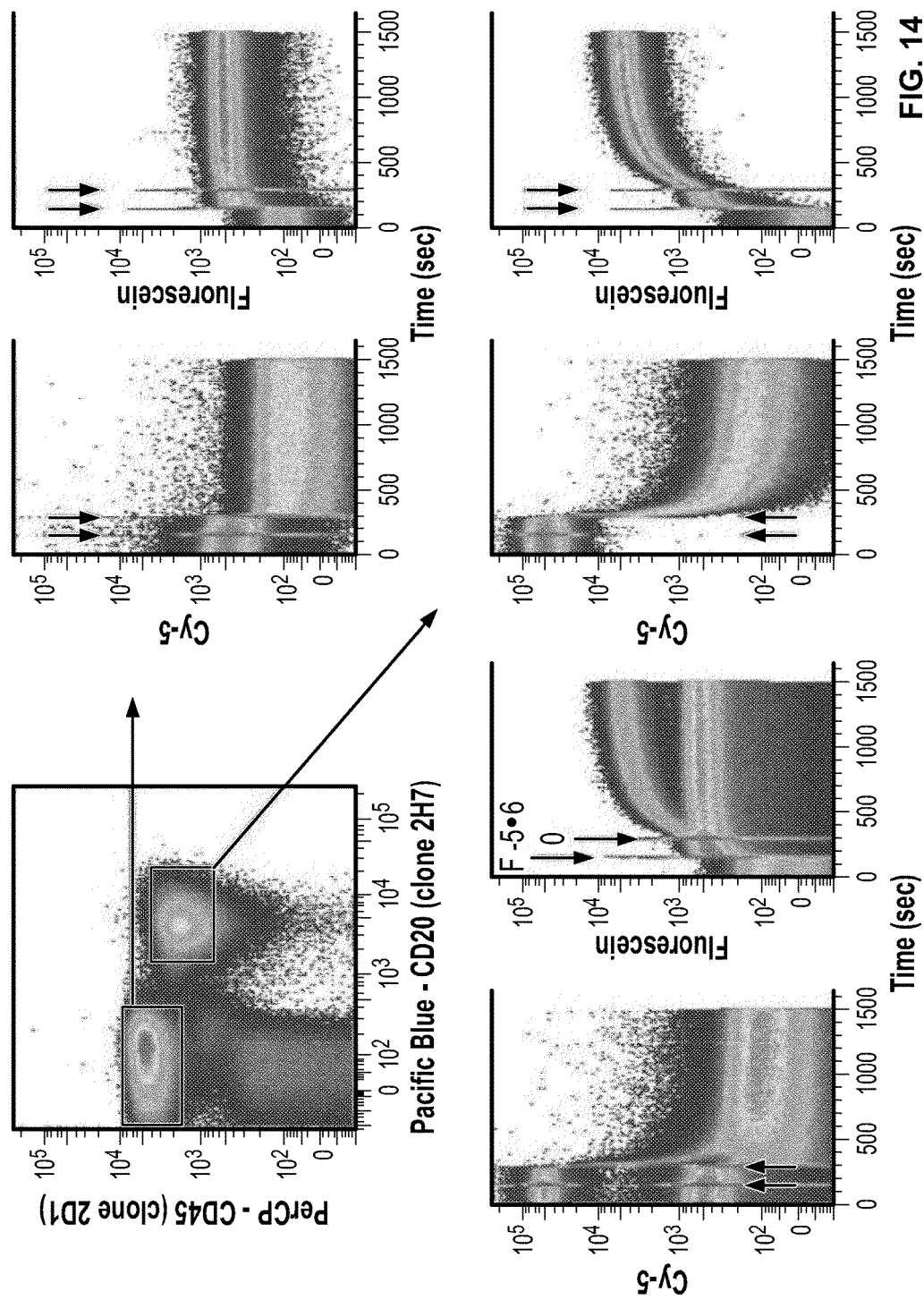
FIG. 14 is a series of flow cytometry images demonstrating a reverse direction cascade (YESCD20YESCD45) showing selective labeling of CD20+ cells and no leak to CD3+ cells that are also CD45+ (Double labeling experiment as well). Anti-CD45 and anti-CD20 antibodies coupled to different fluorophores and targeting different epitopes were used in this experiment to focus the observation on primarily B- and T-cells.

The following example describes the control experimental protocol. Various controls were studied in further detail in automata that are not supposed to provide an answer or cascades that could occur only between markers on separate cells (between two subpopulations). Using the third possible two-step automaton as described above, YESCD3YESCD20, no labeling was observed within the time-frame of the experiment, indicating that T-cells are not observably exchanging elements with B-cells either through diffusion or through direct physical contact of cells (see e.g., FIG. 13). T- and B-cells were separated, labeling the former with $1\cdot 2_{-\alpha CD3}$, the latter with $3\cdot 4_{-\alpha CD20}$. Upon remixing the cells, no crosstalk between different lineages was observed, within the detection limits of the flow cytometer (these are also negative controls for a direct 0+3•4 reaction; see e.g., FIG. 13). Finally, it was demonstrated that automata YESCD20YESCD45, with the inverted order of assessing the cell, worked without labeling any $CD45^+CD20^-$ cells (see e.g., FIG. 14). All of these experiments demonstrate low noise in the automata in the absence of an excess of elements in the solution-phase (i.e., they demonstrate minimal tagging of cells via diffusion or by direct contact between cells). In order to estimate the effects of washing away excess of antibody conjugates, automata YESCD3YESCD20 and YESCD3 (YESCD20 OR YESCD8) were studied without prior removal of the excess components from the solution. In both cases a visible change was observed in the fluorescence of non-target cells, albeit several-fold weaker than in the case of targeted cells (see e.g., FIG. 13).

Figures 15A, 15B:
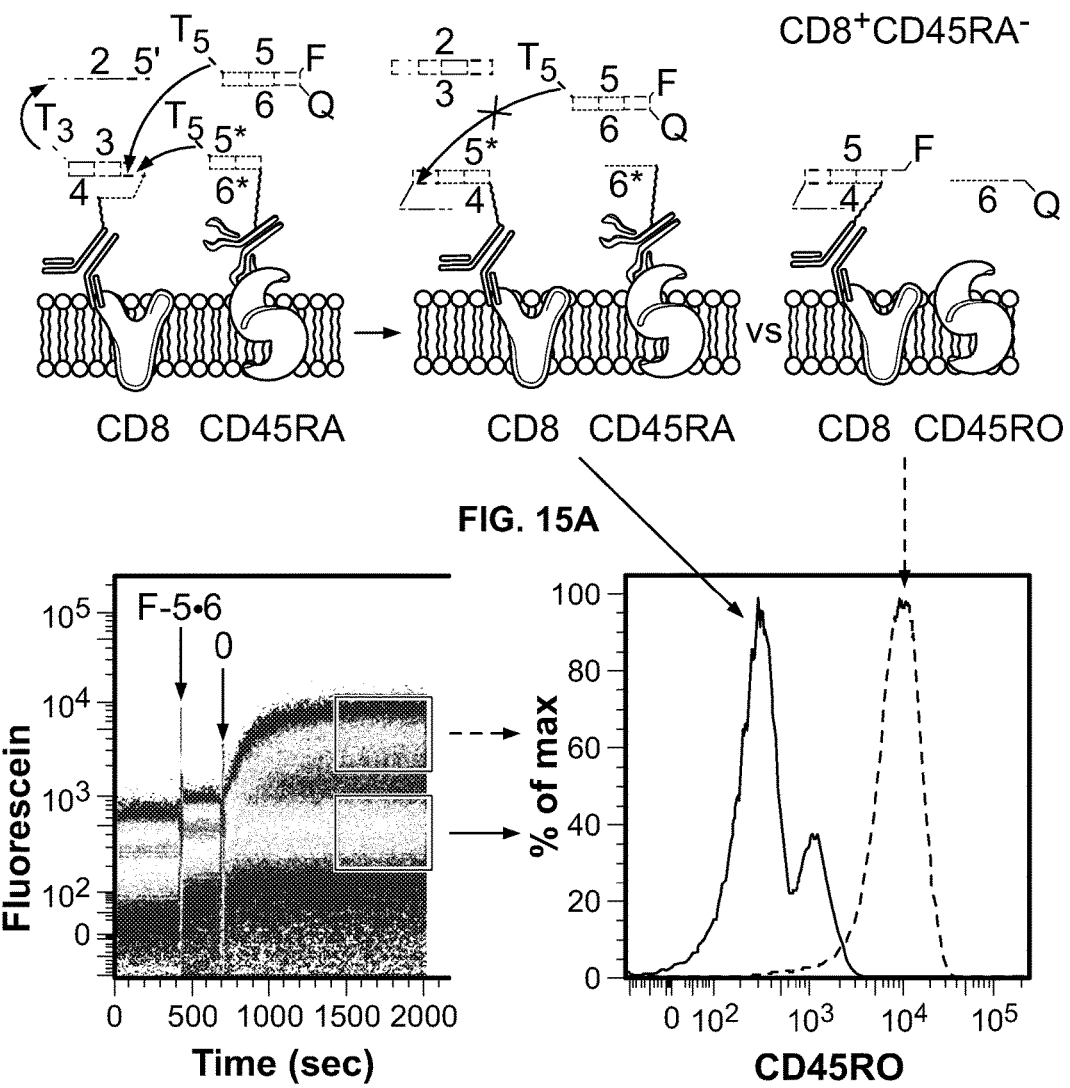
FIG. 15A-FIG. 15C is a series of drawings and spectra showing the demonstration of an automata assessing the absence of a cell surface marker.
Figure 15C:
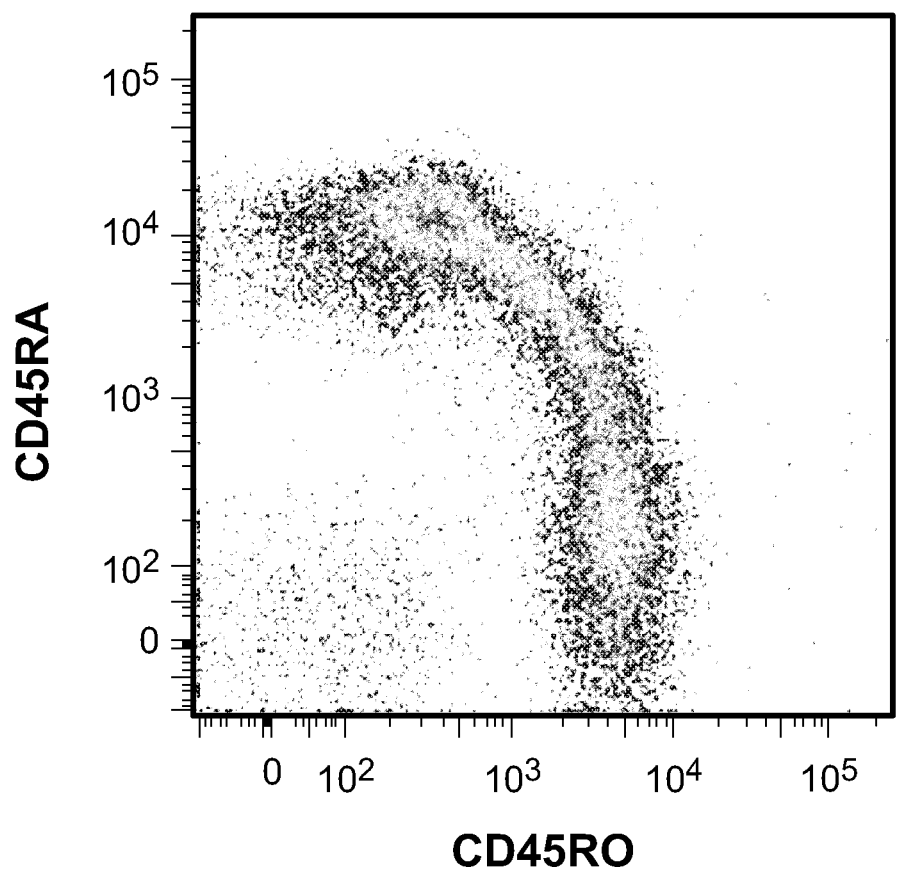
Figure 16A:
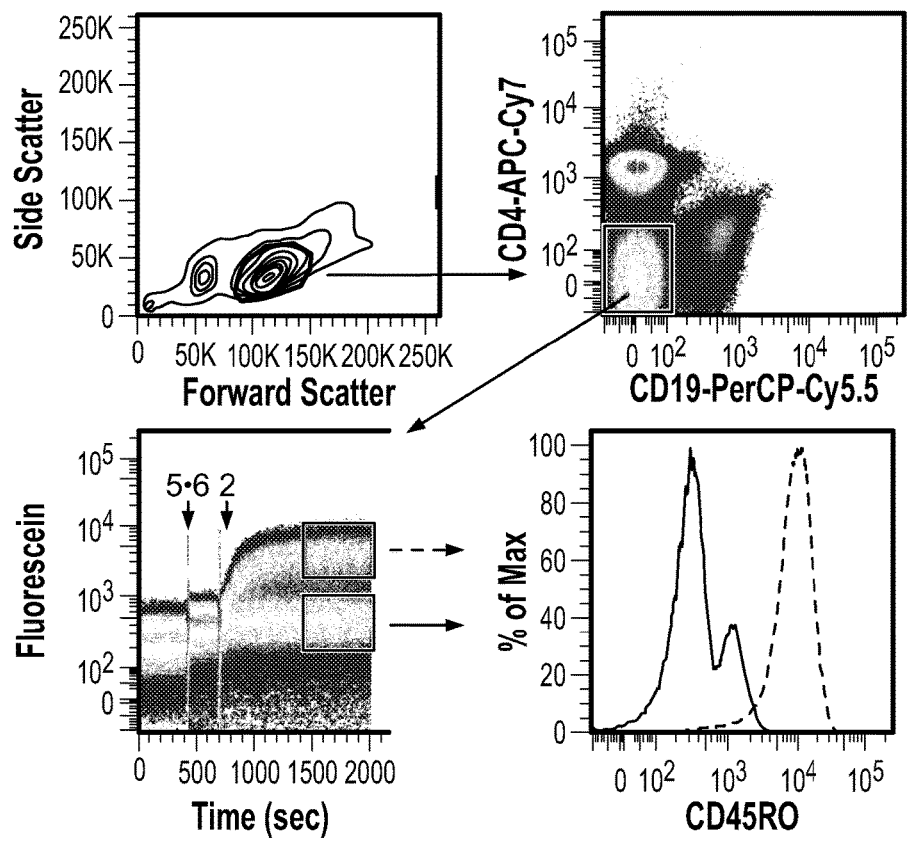
FIG. 16A-FIG. 16B is a series of images and spectra demonstrating YESCD8NOTCD45RA.
Figure 16B:
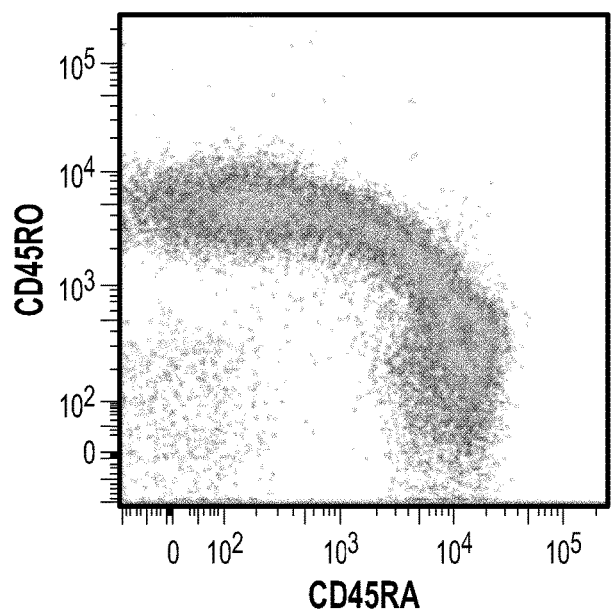

The structures comprising these two-step automata were adjusted to enable an 'if NOT$M_i$ then proceed' function (NOT$M_i$, see e.g., FIG. 15, FIG. 16), i.e., automata labeling cells with fluorescent oligonucleotides only in the absence of a CD marker. During the differentiation of T-cells, from naïve to memory, there is a transition in expression of two different isoforms of CD45 (CD45RA and CD45RO) and an automaton assessing the presence of isoforms of CD45 on CD8⁺T-Cells was created, with one of the isoforms inhibiting the cascade (CD45RA). The automaton YESCD8NOTCD45RA consisted of $3•4_{\alpha CD8}$ and $5**6*_{\alpha CD45RA}$ triggered by 2 in the presence of solution-phase F–5•6. All cells that strongly responded to the automaton, by acquiring F–5 from solution-phase, strongly expressed CD45RO, that is, they were CD45RA⁻ cells (see e.g., FIG. 2B, FIG. 16B). This was in contrast with CD8⁺ CD45RA⁺ T-cells, namely CD45RO⁻ or CD45RO$^{dim}$, which were hindered in acquiring F–5 due to competition with 5* from CD45RA in proximity to CD8-displaying 4, instead forming $5**4_{\alpha CD8}$ (see e.g., FIG. 15, FIG. 16). It should be noted that the 'if NOTM$_i$ then proceed' function is currently limited by the ratio of levels of expression of individual markers on the cell surface (at least until a threshold function is introduced).

Example 18

3-Step Cascade YESCD45YESCD3YESCD8

Figure 17A:
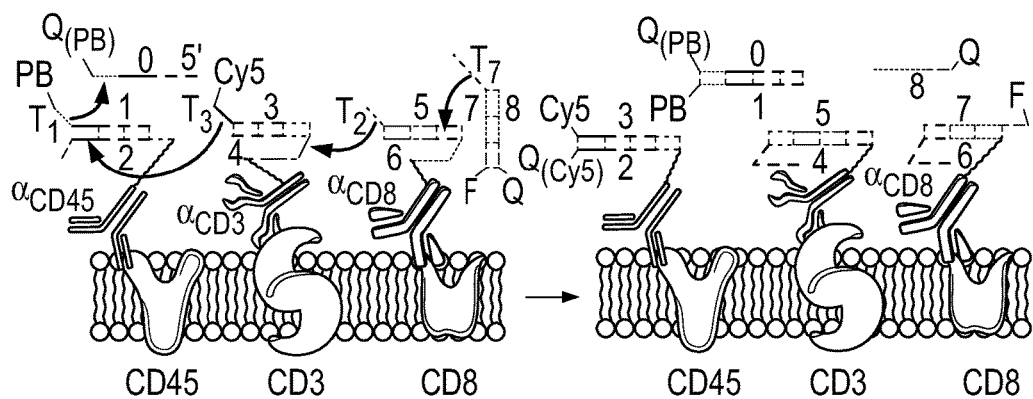
FIG. 17A-FIG. 17B is a series of drawings and spectra demonstrating an automata assessing the presence of three markers (CD45, CD3, and CD8) on the surface of the cell.
Figure 17B:
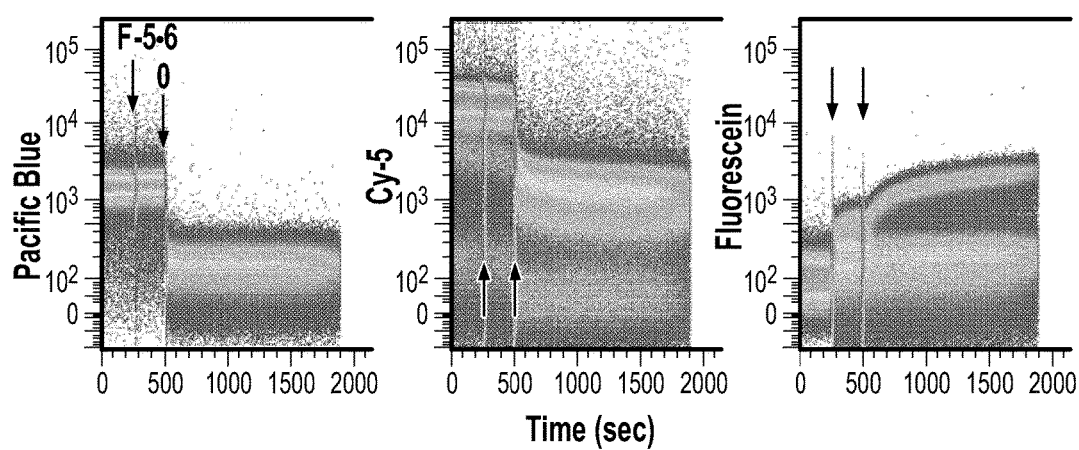
Figure 18:
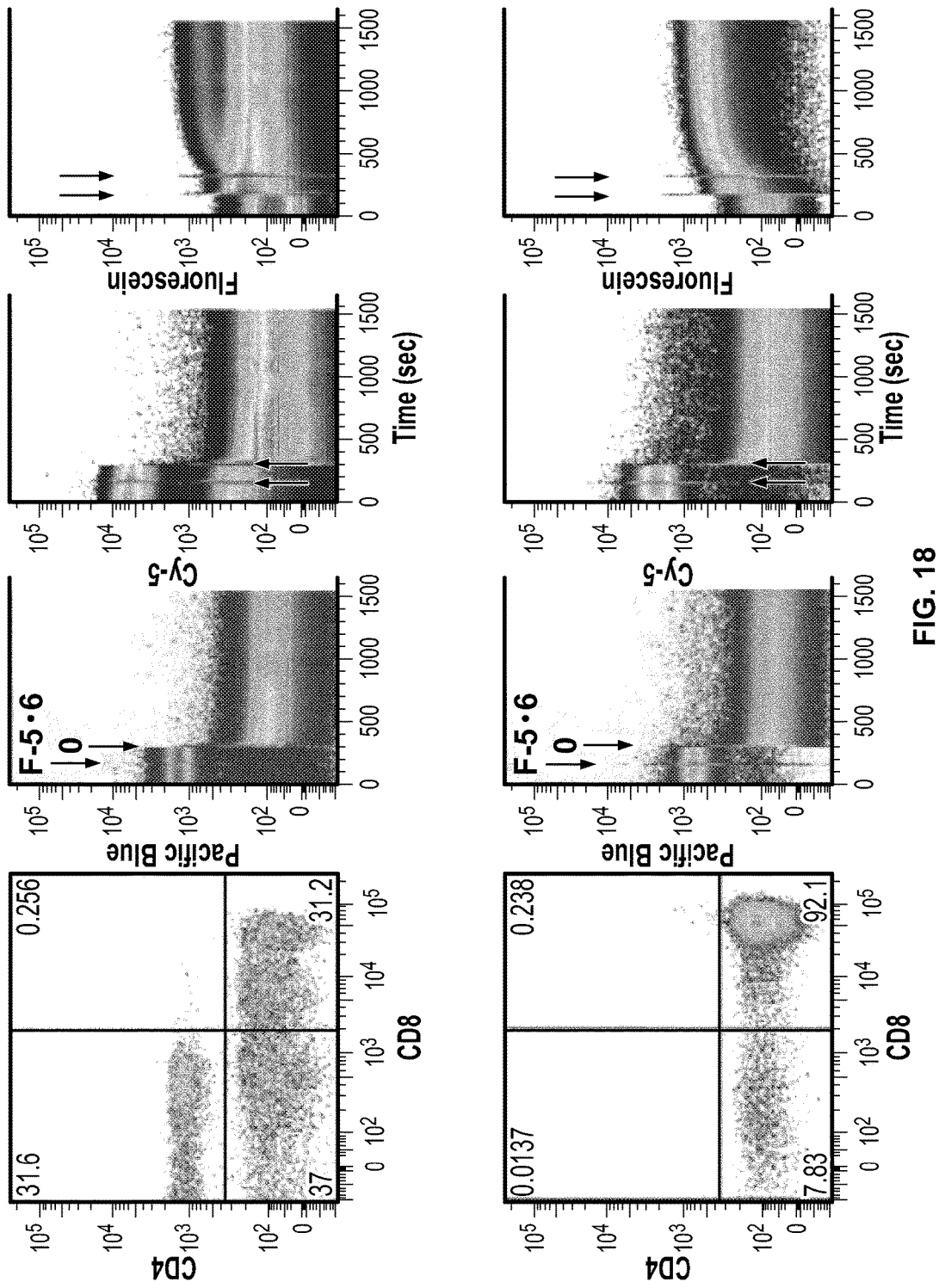
FIG. 18 is a series of images showing three-layer cascade on lymphocytes. Top row shows gated from PBMCs based on light scattering signals. The middle row shows enriched CD8+. The bottom row shows CD4+ cells, as in FIG. 17A-FIG. 17B.
Figure 18:
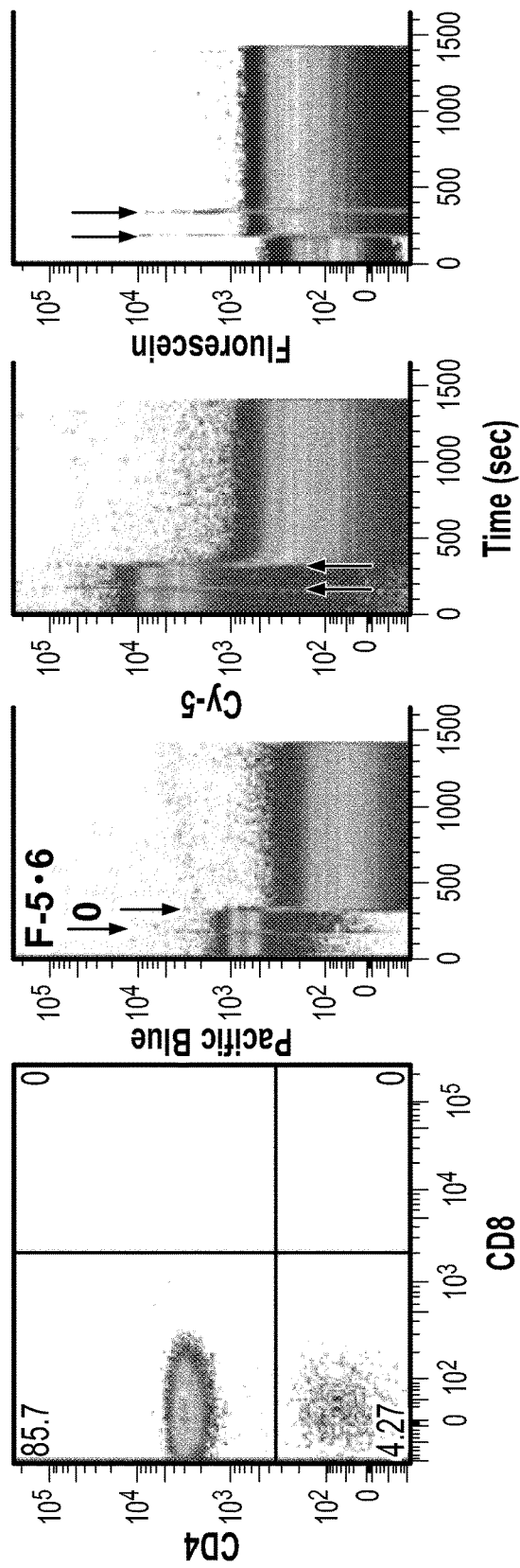

The following example describes the establishment of the three step cascade. The previous examples describe, among other things, the establishment of three types of transitions that could be used to build larger automata, YESM$_i$, NOTM$_i$, and OR (the last function consisting of adding to the cells two antibodies conjugated to identical oligonucleotide components). As an example of the feasibility of building more complex automata from these simple transitions, an automaton with a three-step cascade was built, evaluating the presence of up to three markers, and executing on the cell surface YESCD45YESCD3YESCD8 (the third question: "Is this nucleated hematopoietic cell of T-Cell lineage a CD8 positive cell?", thus separating helper from cytotoxic T-cells). In this automaton, the surface of CD8⁺ cells enabled the following reaction: $0+1•2_{\alpha CD45}+3•4_{\alpha CD3}+5•6_{\alpha CD8}+7•8 \rightarrow 0.1+_{\alpha CD45}2•3+_{\alpha CD3}4•5+_{\alpha CD}86•7+8$. The labeling scheme allowed for the monitoring of each step in this cascade via flow cytometry in real time (see e.g., FIG. 17B, FIG. 18). This automaton was successfully demonstrated on targeted cells, with changes in fluorescence of cells being fully consistent with changes in distances between various components upon each step in the cascade (the first step is monitored by the removal of Pacific Blue, second by the drop in Cy5 due to quenching, and third by the acquisition of fluorescein from solution).

Example 19

Applications of Automata

The following example describes applications of automata. Here, the automata are tested under conditions that could lead to applications. It was demonstrated that: (1) isolation with a purity equivalent to a standard isolation protocol fluorescein-labeled cells after a YESCD45YESCD3 automaton; where a standard method for isolation of cells was used (see e.g., FIG. 1A, using anti-fluorescein antibody conjugated to magnetic beads) and (2) an automaton (using YESCD3YESCD8) can function in whole blood, such that it was possible to simply add automata components to the mixture all together prior to triggering the reaction (see e.g., FIG. 1B). The former demonstration was important, because it showed that there is no detectable decrease in purity of isolated cells between a single step automaton-based procedure (in situ cascade) and the standard separation protocol based on individual separation steps for each CD marker. The latter demonstration also established that blood components did not interfere with the cascades. Together with demonstrations that interactions via solution-phase information transfer do not represent major pathways in labeling cells (see e.g., FIG. 13), this example shows automata can be sued for labeling and eventually eliminating cells in vivo, depending on the pharmacokinetic properties of conjugates.

The above examples have established that a combination of antibodies and oligonucleotide-based reaction cascades can operate as molecular automata to assess the presence or absence of cell surface markers on living human cells.

Example 20

Therapeutic Modules with RIPS

This example describes therapeutic modules that interact with unique oligonucleotides displayed on a targeted cell.

Models of cell targeting with toxins are based on results described above, e.g., YESYES and YESNOT (protective) cascades based on CD8⁺ T-Cells and CD45RO/RA isoforms (CD45RA is mostly located on naive T cells and CD45RO is located on memory T cells). Further demonstration occurs by targeting lymphocyte subpopulations with direct mechanistic implications in animal models. Thus is demonstrated in vivo elimination of specific subpopulations of lymphocytes in rats, and results in animal models can be monitored with imaging approaches described herein. Cytotoxicity is assessed ex vivo with the FMCA assay and cell proliferation with the MTT assay.

Two toxin-delivery module ribosome inactivating proteins (RIPs), saporin and gelonin, are used to target lymphocytes and cancer cells. For saporin, it is estimated that 1,000 binding events of its conjugate on a cell surface is sufficient to cause cell death. Although gelonin is about ~6-10-fold less toxic, it has some significant practical advantages. It is less costly; it is readily available on a larger scale; it has been previously conjugated to oligonucleotides; and used to eliminate specific subsets of lymphocytes with immunotoxins. It was also confirmed that gelonin can be readily conjugated to oligonucleotides at approximately 1:1 ratio. The conjugate to 8 showed low cytotoxicity (>10 μM), unless it was delivered directly across the cell membrane (e.g., via lipofectamine); in this case toxicity became low-to-sub nanomolar.

Toxin-carrying modules contain gelonin or saporin conjugated to an oligonucleotide 5 displayed on CD8. Elimination of subsets of CD8⁺ cells are compared via four possible cascades for three markers (TABLE 1), CD8, CD45RO, and CD45RA (CD45 isoforms RO and RA are mostly exclusive, although there are some minor mixed populations, cf., FIG. 4A).

TABLE 1

|     | CD8 | CD45RO | CD45RA |   |
| --- | --- | --- | --- | --- |
| I   | +   | +   |     | T |
| I   | +   |     | +   |   |
| II  | +   | +   |     |   |
| II  | +   |     | +   | T |
| III | +   | +   |     |   |
| III | +   |     | +   | T |
| IV  | +   | +   |     | T |
| IV  | +   |     | +   |   |

Each of yesCD8yesCD45RO (I) and yesCD8notCD45RO (II), yesCD8yesCD45RA (III) and yesCD8notCD45RA (IV) are tested with delivery of toxin module (T in table). Aside from standard assays, proof of activity of RIPs (i.e., ability to halt protein synthesis) is confirmed by a radioactive glycine uptake assay.

Figure 23A:
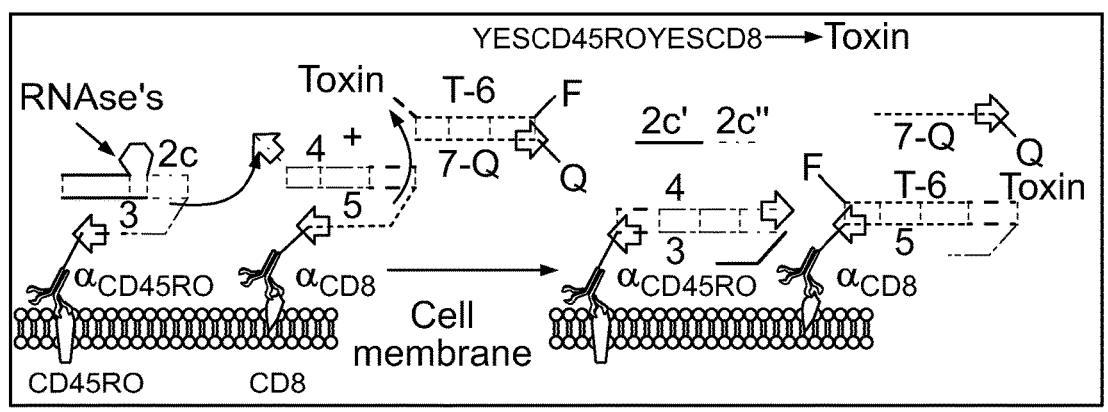
FIG. 23A-FIG. 23B is an illustration of a therapeutic module having a toxin conjugate.

One scheme for cascade I is provided in FIG. 23A, with toxin being conjugated to 6 as in 6*7 conjugate. In two-step cascades, lengths of oligonucleotides can be minimized (down to 30) and mismatches that were introduced to prevent non-specific interaction with downstream elements in three-and-more-step cascades can be eliminated. RNAse's triggered degradation of RNA can be used to start a cascade so as to simplify a therapeutic procedure by reducing the number of injections. The cascade can be triggered by a cleavage of an RNA loop.

Figure 23B:
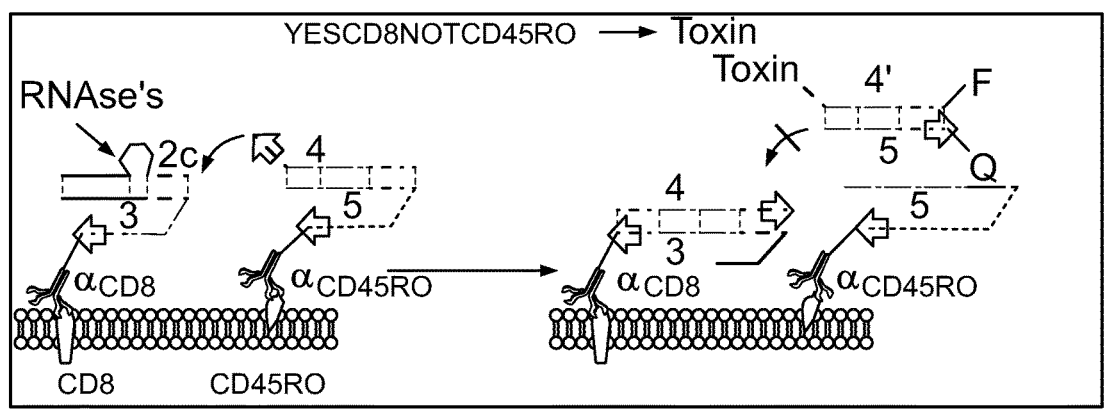

One scheme for a protective cascade (e.g., II) is given in FIG. 23B. This is a cascade in which CD8+ cells are protected by the presence of CD45RO; thus, the uptake of the toxin from solution is minimized by the faster competing reaction from the cell surface. This cascade can be optimized by adjusting toehold regions and by optimizing loads of antibody-oligonucleotide conjugates.

Additional demonstrations in animal models include CD4+CD25+ Vbeta (18+7+8.6) $T_{reg}$ or CD4+CD45RC+ $T_c$ cells. Additional demonstrations in clinical models include CLL lymphocytes targeted via yesCD19yesCD5.]

Example 21

Therapeutic Modules with Cardiotonic Steroids

Cardiotonic steroids are known for inhibiting digitalis-sensitive isoforms of Na+,K+ ATPases in the cell membranes of human cells, inducing differentiation and causing apoptosis and cytolysis in a variety of human tumor cell lines, with EC50's ranging from 380 pM to 10 nM. Using several established tumor cell lines (e.g. Jurkat, U-937, CCRF-CEM, PLC/PRF5), these reports were confirmed, i.e., that bufalin is cytotoxic at EC50<10 nM.

The severe toxicity of cardiotonic steroids with serum concentrations above the 5-10 nM range has precluded their administration to humans in tumoricidal doses. However, cardiotonic steroids have been used therapeutically for centuries and human subjects without cardiac disease can easily tolerate total digoxin body stores of 2.5 µmoles and serum digoxin concentrations of 2 nM. Unlike other potent low MW compounds (such as calicheamicin and maytansine), cardiotonic steroids have been well characterized pharmacologically and pharmacokinetically, are readily measured in blood, and have specific Fab antidotes which can also be used to promote the excretion of drug being released from targeted cells. As such, reaction cascades allow sufficient local (effective) tumor concentrations, while keeping concentrations of drug in serum and in normal tissues below the established toxic range.

Also demonstrated is bufalin esters and carbamates at the C3 hydroxyl group can control cytotoxicity.

Bufalin
A: 5 nM 90 nM
B

6 µM
C

Galactosidase cleavage

While ordinary esters (e.g. succinamate) are reasonably cytotoxic (~10-20 nM), sterically hindered carbamates and esters were found to be three orders of magnitude less cytotoxic. This result support that bufalin analogs with well-adjusted steric hindrance can be used as prodrugs or in conjugates.

Example 22

Preventing Graft Versus Host Disease

This example describes two step cascades for elimination of naïve T-cells.

Naïve T-cells are CD3 positive, CD45RA positive (CD3+ CD45RA+). Many β-cells are CD45RA+. All other T-cells are CD3+.

Figure 24:
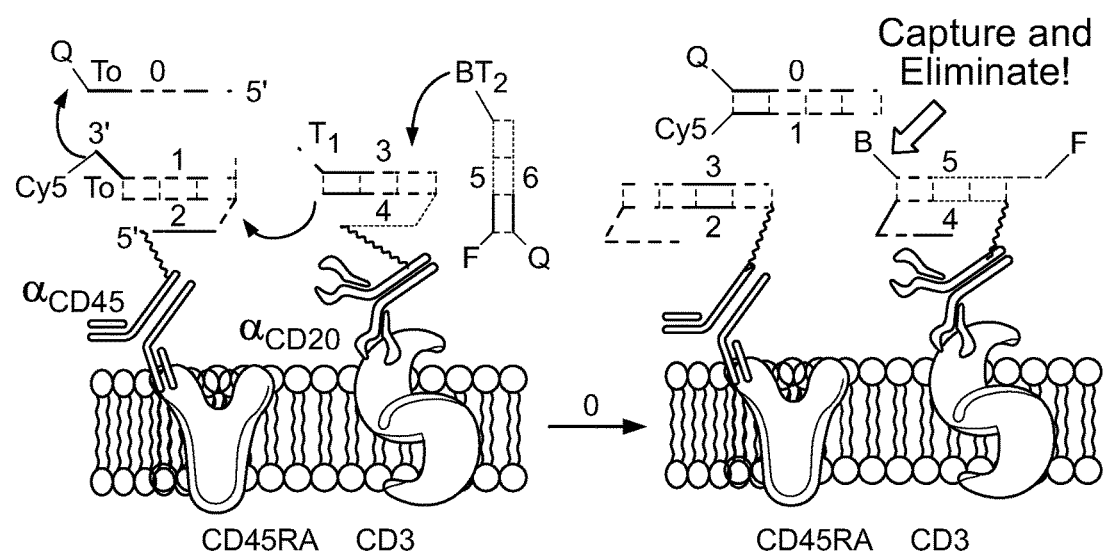
FIG. 24 is an illustration of a Y ESCD45RAYESCD3 module.

A two step yesCD45RAyesCD3 cascade is depicted in FIG. 24. FIG. 25 Flow cytometry was used to analyze and isolate various cell samples exposed or not to magnetic beads or the yesCD45RAyesCD3 module. Control (no magnetic beads, no module) is shown in FIG. 25A. Control (magnetic beads, no module) is shown in FIG. 25B. Cells exposed to module and magnetic beads are shown in FIG. 25C. FIG. 25D shows flow-cytometry of a sample of control cells not exposed to module and not exposed to magnetic beads prior to separation, where 36% are CD19/20⁻CD3⁻, 59.1% are T-cells, and 4.9% are B-cells. FIG. 25E shows flow-cytometry of a sample of control cells not exposed to module and exposed to magnetic beads, where 77.5% are CD19/20⁻CD3⁻, 18.4% are T-cells, and 4.1% are B-cells. FIG. 25F shows flow-cytometry of a sample of cells exposed to module and exposed to magnetic beads, where 1.3% are CD19/20⁻ CD3⁻, 96.2% are T-cells, and 2.5% are B-cells.

As shown above, the YESCD45RAYESCD3 module can provide for isolation of naïve T-cells. Such an approach can be used for depleting T-cells from an allograft so as to prevent attack of recipient tissues (see generally, Anderson et al. 2013 Biol Blood Marrow Transplant 19, 185-195).

---

The invention claimed is:

1. A molecular automaton system for isolation, elimination, or treatment of a target biological object,
(I) where the target biological object comprises a first object surface marker and a second object surface marker, the system comprises
  (a) a first target marker comprising
    (i) a first target-specific agent specific for the first object surface marker, and
    (ii) a first double strand complex comprising a first oligonucleotide and a second oligonucleotide, the second oligonucleotide linked to the first target-specific agent;
  (b) a second target marker comprising
    (i) a second target-specific agent specific for the second object surface marker, and
    (ii) a second double strand complex comprising a third oligonucleotide and a fourth oligonucleotide, the fourth oligonucleotide linked to the second target-specific agent;
  (c) a single stranded fifth oligonucleotide; and
  (d) a single stranded sixth oligonucleotide linked to an isolation agent, a cytotoxic agent, or a therapeutic agent;

wherein,
the first oligonucleotide has more complementarity for the fifth oligonucleotide than for the second oligonucleotide, such that when in proximity, the fifth oligonucleotide will disrupt the first double strand complex to form a single stranded second oligonucleotide and a third double strand complex comprising the first oligonucleotide and the fifth oligonucleotide;
the third oligonucleotide has more complementarity for the second oligonucleotide than for the fourth oligonucleotide, such that when in proximity, the single stranded second oligonucleotide will disrupt the second double strand complex to form a single stranded fourth oligonucleotide and a fourth double strand complex comprising the second oligonucleotide and the third oligonucleotide, the fourth double strand complex linked to the first target-specific agent via the second oligonucleotide, and the single stranded fourth oligonucleotide linked to the second target-specific agent; and
the sixth oligonucleotide has sufficient complementarity to the single stranded fourth oligonucleotide to form a fifth double strand complex therewith, but has insufficient complementarity for the fourth oligonucleotide to disrupt the second double strand complex; or (II) where the target biological object comprises a first object surface marker but not a second object surface marker, the system comprises
(a) a first target marker comprising
(i) a first target-specific agent specific for the first object surface marker, and
(ii) a first double strand complex comprising a first oligonucleotide and a second oligonucleotide, the second oligonucleotide linked to the first target-specific agent;
(b) a second target marker comprising
(i) a second target-specific agent specific for the second object surface marker, and
(ii) a second double strand complex comprising a third oligonucleotide and a fourth oligonucleotide, the fourth oligonucleotide linked to the second target-specific agent;
(c) a single stranded fifth oligonucleotide;
(d) a sixth double strand complex comprising a sixth oligonucleotide and a seventh oligonucleotide, the sixth oligonucleotide linked to an isolation agent, a cytotoxic agent, or a therapeutic agent;
wherein,
the first oligonucleotide has more complementarity for the fifth oligonucleotide than for the second oligonucleotide, such that when in proximity, the fifth oligonucleotide will disrupt the first double strand complex to form a single stranded second oligonucleotide and a third double strand complex comprising the first oligonucleotide and the fifth oligonucleotide;
the third oligonucleotide has more complementarity for the second oligonucleotide than for the fourth oligonucleotide, such that when in proximity, the single stranded second oligonucleotide will disrupt the second double strand complex to form a single stranded fourth oligonucleotide and a fourth double strand complex comprising the second oligonucleotide and the third oligonucleotide, the fourth double strand complex linked to the first target-specific agent via the second oligonucleotide, and the single stranded fourth oligonucleotide linked to the second target-specific agent;
the sixth oligonucleotide has more complementarity for the second oligonucleotide than for the seventh oligonucleotide, such that when in proximity, the single stranded second oligonucleotide will disrupt the sixth double strand complex to form a single stranded seventh oligonucleotide and a seventh double strand complex comprising the second oligonucleotide and the sixth oligonucleotide, the seventh double strand complex linked to the first target-specific agent via the second oligonucleotide, and the single stranded fourth oligonucleotide linked to the second target-specific agent; and
the third oligonucleotide has more complementarity for the second oligonucleotide than the sixth oligonucleotide has for the second oligonucleotide, such that when in proximity, the sixth oligonucleotide cannot displace the third oligonucleotide from the fourth double strand complex comprising the second oligonucleotide and the third oligonucleotide.

2. The system of claim 1, wherein the system forms a marked target biological object.

3. The system of claim 1, wherein the target biological object comprises at least one of a cell, an organelle, or a vesicle.

4. The system of claim 1, wherein the target biological object comprises at least one of a stem cell, a leukocyte group, a granulocytes, a monocyte, a T lymphocyte, a T helper cell, a T regulatory cell, a cytotoxic T cell, a naïve T cell, a lymphocyte, a thrombocyte, or a natural killer cell.

5. The system of claim 4, wherein the target biological object comprises at least one of a natural killer cell, a T-cell, or a B-cell.

6. The system of claim 1, wherein the target biological object is selected from the group consisting of an exosome, apoptotic bleb, shedding vesicle, microparticle, prostasome, tolerosome, prom inosome, unilamellar liposome vesicle, or multilamellar liposome vesicle, vacuole, plant vacuole, contractile vacuole, lysosome, peroxisome, transport vesicle, secretory vesicle, synaptic vesicle, hormonal secretory vesicle, cell wall-associated vesicle, toxic membrane vesicle, signal molecule vesicle, gas vesicle, membrane vesicle, matrix vesicle, multivesicular body, outer membrane vesicle, mitochondria, plastic, flagellum, endoplasmic reticulum, Golgi apparatus, vacuole, nucleus, acrosome, autophagosome, centriole, cilium, eyespot apparatus, glycosome, glyoxosome, hydrogenosome, lysosome, melanosome, mitosome, myofibril, nematocyst, nucleolus, parenthesome, peroxisome, proteasome, ribosome, 80s ribosome, vesicle, nucleosome, microtubule, large RNA and RNA-protein complex, ribosome, spliceosome, vault, proteasome, DNA polymerase III holoenzyme, RNA polymerase II holoenzyme, symmetric viral capsid, complex of GroEL and GroES, membrane protein complex, photosystem I, ATP synthase, large DNA and DNA-protein complex, nucleosome, centriole and microtubule-organizing center, cytoskeleton, nucleolus, carboxysome, chlorosome, magnetosome, nucleoid, plasmid, ribosome, 70s ribosome, thylakoid, and mesasome.

7. The system of claim 1, wherein the target biological object is produced by or associated with at least one of a stem cell, a leukocyte group, a granulocytes, a monocyte, a T lymphocyte, a T helper cell, a T regulatory cell, a cytotoxic T cell, a naïve T cell, a lymphocyte, a thrombocyte, or a natural killer cell.

8. The system of claim 7, wherein the target biological object is produced by or associated with at least one of a natural killer cell, a T-cell, or a B-cell.

9. The system of claim 1, wherein
the target biological object is a stem cell and the first object surface marker or the second object surface marker is selected from the group consisting of CD34+, CD31−, and CD117;
the target biological object is a leukocyte group and the first object urface marker or the second object surface marker is CD45+;
the target biological object is a granulocyte and the first object surface marker or the second object surface marker is selected from the group consisting of CD45+, CD11 b, CD15+, CD24+, CD114+, and CD182+;
the target biological object is a monocyte and the first object surface marker or the second object surface marker is selected from the group consisting of CD45+, CD14+, CD114+, CD11a, CD11 b, CD91+, CD16+;
the target biological object is a T lymphocyte and the first object surface marker or the second object surface marker is selected from the group consisting of CD45+ and CD3+;
the target biological object is a T helper cell and the first object surface marker or the second object surface marker is selected from the group consisting of CD45+, CD3+, and CD4+;
the target biological object is a T regulatory cell and the first object surface marker or the second object surface marker is selected from the group consisting of CD4, CD25, and Foxp3;
the target biological object is a Cytotoxic T cell and the first object surface marker or the second object surface marker is selected from the group consisting of CD45+, CD3+, and CD8+;
the target biological object is a naïve T-cell and the first object surface marker or the second object surface marker is selected from the group consisting of CD45RA+ and CD3+;
the target biological object is a B lymphocyte and the first object surface marker or the second object surface marker is selected from the group consisting of CD45+, CD19+ or CD45+, CD20+, CD24+, CD38, and CD22;
the target biological object is a Thrombocyte and the first object surface marker or the second object surface marker is selected from the group consisting of CD45+ and CD61+; or
the target biological object is a Natural killer cell and the first object surface marker or the second object surface marker is selected from the group consisting of CD16+, CD56+, CD3−, CD31, CD30, and CD38.

10. The system of claim 1, wherein:
the first target-specific agent comprises a first antibody specific for the first object surface marker; and
the second target-specific agent comprises a second antibody specific for the second object surface marker.

11. The system of claim 10, wherein:
the first target-specific agent comprises a first monoclonal antibody specific for the first object surface marker; and
the second target-specific agent comprises a second monoclonal antibody specific for the second object surface marker.

12. The system of claim 1, wherein the first object surface marker or the second object surface marker is selected from the group consisting of a Type 1 receptor, Type 2 G protein-coupled receptor, Type 3 kinase linked receptor, and Type 4 nuclear receptor.

13. The system of claim 1, wherein the first object surface marker or the second object surface marker is selected from the group consisting of an immune receptor, pattern recognition receptor, Toll-like receptor, killer activated receptor and killer inhibitor receptor, complement receptor, Fc receptor, B cell receptor, T cell receptor, cytokine receptor, ion channel linked receptor, nicotinic acetylcholine receptor, glycine receptor, gamma-aminobutyric acid receptor, gamma-aminobutyric acid A receptor, gamma-aminobutyric acid C receptor, glutamate receptor, N-methyl-D-aspartate receptor, α amino-3-hydroxy-5-methyl-4-isoxazolepropionic acid receptor, Kainate receptor, 5-HT3 receptor, P2X receptor, cyclic nucleotide-gated ion channel, Inositol triphosphate receptor, intracellular ATP receptor, and ryanodine receptor.

14. The system of claim 1, wherein the first object surface marker or the second object surface marker is selected from the group consisting of a clathrin coat-associated marker, COPI coat-associated marker, COPII coat-associated marker, coatomer coat-associated marker, SNARE marker, v-SNARE, t-SNARE, Qa SNARE, Qb SNARE, Qc SNARE, and R SNARE.

15. The system of claim 1, wherein the first object surface marker or the second object surface marker is a small molecule selected from the group consisting of a steroid or nitro-phenol compound.

16. The system of claim 1, wherein the first oligonucleotide, the second oligonucleotide, the third oligonucleotide, the fourth oligonucleotide, the fifth oligonucleotide, the sixth oligonucleotide, or the seventh oligonucleotide comprise about 10 to about 100 nucleotides.

17. The system of claim 16, wherein the first oligonucleotide, the second oligonucleotide, the third oligonucleotide, the fourth oligonucleotide, the fifth oligonucleotide, the sixth oligonucleotide, or the seventh oligonucleotide comprise about 10, about 15, about 20, about 25, about 30, about 35, about 40, about 45, about 50, about 55, about 60, about 65, about 70, about 75, about 80, about 85, about 90, about 95, or about 100 nucleotides.

18. The system of claim 1, wherein more complementarity comprises about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45%, about 50%, about 55%, or about 60%.

19. The system of claim 1, wherein
a double strand complex comprises a pair of oligonucleotides having a difference in nucleotide number selected from the group consisting of about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, and about 25 nucleotides; and
the difference in nucleotide number creates a toe hold sufficient to drive a strand-displacement reaction.

20. The system of claim 1, wherein the target biological object is isolated according to at least one of flow cytometry, fluorescence-activated cell sorting, magnetic-activated cell sorting, Cytometric Bead Array, a magnetic nanoparticle coated with an anti-fluorochrome antibody, superparamagnetic spherical polymer particles, polymer beads coated with an anti-fluorochrome antibody, avidin, or streptavidin, or plasmapheresis.

21. A method for isolating, eliminating, or treating a target biological object with the molecular automaton system of claim 1, comprising:
- (I) (a) contacting the first target marker, the second target marker, and a population of biological objects optionally comprising the target biological object, the target biological object comprising the first object surface marker and the second object surface marker, to form a marked target biological object; and
  - (b) contacting the single stranded fifth oligonucleotide and the single stranded sixth oligonucleotide linked to the isolation agent, the cytotoxic agent, or the therapeutic agent with the marked target biological object; or
- (II) (a) contacting the first target marker, the second target marker, and a population of biological objects optionally comprising the target biological object, the target biological object comprising the first object surface marker but not the second object surface marker, to form a marked target biological object; and
  - (b) contacting the single stranded fifth oligonucleotide and the sixth double strand complex linked to the isolation agent, the cytotoxic agent, or the therapeutic agent with the marked target biological object.

22. The method of claim 21, wherein the target biological object comprises a cell, an organelle, or a vesicle.

23. The method of claim 21, wherein the target biological object comprises a stem cell, a leukocyte group, a granulocytes, a monocyte, a T lymphocyte, a T helper cell, a T regulatory cell, a cytotoxic T cell, a nave T cell, a lymphocyte, a thrombocyte, or a natural killer cell.

24. The method of claim 23, wherein the target biological object comprises at least one of a natural killer cell, a T-cell, or a B-cell.

25. The method of claim 21, wherein the target biological object is selected from the group consisting of an exosome, apoptotic bleb, shedding vesicle, microparticle, prostasome, tolerosome, prominosome, unilamellar liposome vesicle, or multilamellar liposome vesicle, vacuole, plant vacuole, contractile vacuole, lysosome, peroxisome, transport vesicle, secretory vesicle, synaptic vesicle, hormonal secretory vesicle, cell wall-associated vesicle, toxic membrane vesicle, signal molecule vesicle, gas vesicle, membrane vesicle, matrix vesicle, multivesicular body, outer membrane vesicle, mitochondria, plastic, flagellum, endoplasmic reticulum, Golgi apparatus, vacuole, nucleus, acrosome, autophagosome, centriole, cilium, eyespot apparatus, glycosome, glyoxosome, hydrogenosome, lysosome, melanosome, mitosome, myofibril, nematocyst, nucleolus, parenthesome, peroxisome, proteasome, ribosome, 80s ribosome, vesicle, nucleosome, microtubule, large RNA and RNA-protein complex, ribosome, spliceosome, vault, proteasome, DNA polymerase III holoenzyme, RNA polymerase II holoenzyme, symmetric viral capsid, complex of GroEL and GroES, membrane protein complex, photosystem I, ATP synthase, large DNA and DNA-protein complex, nucleosome, centriole and microtubule-organizing center, cytoskeleton, nucleolus, carboxysome, chlorosome, magnetosome, nucleoid, plasmid, ribosome, 70s ribosome, thylakoid, and mesasome.

26. The method of claim 21, wherein the target biological object is produced by or associated with a stem cell, a leukocyte group, a granulocytes, a monocyte, a T lymphocyte, a T helper cell, a T regulatory cell, a cytotoxic T cell, a nave T cell, a lymphocyte, a thrombocyte, or a natural killer cell.

27. The method of claim 26, wherein the target biological object is produced by or associated with at least one of a natural killer cell, a T-cell, or a B-cell.

28. The method of claim 21, wherein
- the target biological object is a stem cell and the first object surface marker or the second object surface marker is selected from the group consisting of CD34+, CD31−, and CD117;
- the target biological object is a leukocyte group and the first object surface marker or the second object surface marker is CD45+;
- the target biological object is a granulocyte and the first object surface marker or the second object surface marker is selected from the group consisting of CD45+, CD11 b, CD15+, CD24+, CD114+, and CD182+;
- the target biological object is a monocyte and the first object surface marker or the second object surface marker is selected from the group consisting of CD45+, CD14+, CD114+, CD11a, CD11 b, CD91+, CD16+;
- the target biological object is a T lymphocyte and the first object surface marker or the second object surface marker is selected from the group consisting of CD45+ and CD3+;
- the target biological object is a T helper cell and the first object surface marker or the second object surface marker is selected from the group consisting of CD45+, CD3+, and CD4+;
- the target biological object is a T regulatory cell and the first object surface marker or the second object surface marker is selected from the group consisting of CD4, CD25, and Foxp3;
- the target biological object is a Cytotoxic T cell and the first object surface marker or the second object surface marker is selected from the group consisting of CD45+, CD3+, and CD8+;
- the target biological object is a naïve T-cell and the first object surface marker or the second object surface marker is selected from the group consisting of CD45RA+ and CD3+;
- the target biological object is a B lymphocyte and the first object surface marker or the second object surface marker is selected from the group consisting of CD45+, CD19+ or CD45+, CD20+, CD24+, CD38, and CD22;
- the target biological object is a Thrombocyte and the first object surface marker or the second object surface marker is selected from the group consisting of CD45+ and CD61+; or
- the target biological object is a Natural killer cell and the first object surface marker or the second object surface marker is selected from the group consisting of CD16+, CD56+, CD3−, CD31, CD30, and CD38.

29. The method of claim 21, wherein:
the first target-specific agent comprises a first antibody specific for the first object surface marker; and
the second target-specific agent comprises a second antibody specific for the second object surface marker.

30. The method of claim 21, wherein:
the first target-specific agent comprises a first monoclonal antibody specific for the first object surface marker; and
the second target-specific agent comprises a second monoclonal antibody specific for the second object surface marker.

31. The method of claim 21, wherein the first object surface marker or the second object surface marker is selected from the group consisting of a Type 1 receptor, Type 2 G protein-coupled receptor, Type 3 kinase linked receptor, and Type 4 nuclear receptor.

32. The method of claim 21, wherein the first object surface marker or the second object surface marker is selected from the group consisting of an immune receptor, pattern recognition receptor, Toll-like receptor, killer activated receptor and killer inhibitor receptor, complement receptor, Fc receptor, B cell receptor, T cell receptor, cytokine receptor, ion channel linked receptor, nicotinic acetylcholine receptor, glycine receptor, GABA gamma-aminobutyric acid receptor, gamma-aminobutyric acid A receptor, gamma-aminobutyric acid C receptor, glutamate receptor, methyl-D-aspartate receptor, α amino-3-hydroxy-5-methyl-4-isoxazolepropionic acid receptor, Kainate receptor, 5-HT3 receptor, P2X receptor, cyclic nucleotide-gated ion channel, Inositol triphosphate receptor, intracellular ATP receptor, and ryanodine receptor.

33. The method of claim 21, wherein the first object surface marker or the second object surface marker is selected from the group consisting of a clathrin coat-associated marker, COPI coat-associated marker, COPII coat-associated marker, coatomer coat-associated marker, SNARE marker, v-SNARE, t-SNARE, Qa SNARE, Qb SNARE, Qc SNARE, and R SNARE.

34. The method of claim 21, wherein the first object surface marker or the second object surface marker is a small molecule selected from the group consisting of a steroid or nitro-phenol compound.

35. The method of claim 21, wherein the first oligonucleotide, the second oligonucleotide, the third oligonucleotide, the fourth oligonucleotide, the fifth oligonucleotide, the sixth oligonucleotide, or the seventh oligonucleotide comprise about 10 to about 100 nucleotides.

36. The method of claim 29, wherein the first oligonucleotide, the second oligonucleotide, the third oligonucleotide, the fourth oligonucleotide, the fifth oligonucleotide, the sixth oligonucleotide, or the seventh oligonucleotide comprise about 10, about 15, about 20, about 25, about 30, about 35, about 40, about 45, about 50, about 55, about 60, about 65, about 70, about 75, about 80, about 85, about 90, about 95, or about 100 nucleotides.

37. The method of claim 21, wherein more complementarity comprises about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45%, about 50%, about 55%, or about 60%.

38. The method of claim 21, wherein
a double strand complex comprises a pair of oligonucleotides having a difference in nucleotide number selected from the group consisting of about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, and about 25 nucleotides; and
the difference in nucleotide number creates a toe hold sufficient to drive a strand-displacement reaction.

39. The method of claim 2, wherein the target biological object is isolated according to at least one of flow cytometry, fluorescence-activated cell sorting, magnetic-activated cell sorting, Cytometric Bead Array, a magnetic nanoparticle coated with an anti-fluorochrome antibody, superparamagnetic spherical polymer particles, polymer beads coated with an anti-fluorochrome antibody, avidin, or streptavidin, or plasmapheresis.

* * * * *

UNITED STATES PATENT AND TRADEMARK OFFICE
CERTIFICATE OF CORRECTION

PATENT NO. : 10,338,068 B2
APPLICATION NO. : 14/931941
DATED : July 2, 2019
INVENTOR(S) : Millan N. Stojanovic et al.

Page 1 of 1

It is certified that error appears in the above-identified patent and that said Letters Patent is hereby corrected as shown below:

In the Specification

Column 1, Line 16 should read:
-- This invention was made with government support under CA147925 awarded by the National Institutes of Health. The government has certain rights in the invention. --

Signed and Sealed this
Fifth Day of November, 2019

Andrei Iancu
*Director of the United States Patent and Trademark Office*